US011992373B2

(12) United States Patent
Calloway et al.

(10) Patent No.: US 11,992,373 B2
(45) Date of Patent: May 28, 2024

(54) AUGMENTED REALITY HEADSET WITH VARIED OPACITY FOR NAVIGATED ROBOTIC SURGERY

(71) Applicant: GLOBUS MEDICAL, INC., Audubon, PA (US)

(72) Inventors: Thomas Calloway, Pelham, NH (US); Weston Healy, Cambridge, MA (US); Isaac Dulin, Somerville, MA (US); Dale Earle, Hudson, NH (US); Keiichi Matsuda, London (GB)

(73) Assignee: Globus Medical, Inc, Audubon, PA (US)

( * ) Notice: Subject to any disclaimer, the term of this patent is extended or adjusted under 35 U.S.C. 154(b) by 1175 days.

(21) Appl. No.: 16/708,937

(22) Filed: Dec. 10, 2019

(65) Prior Publication Data

US 2021/0169578 A1    Jun. 10, 2021

(51) Int. Cl.
*A61B 90/50*     (2016.01)
*A61B 34/00*     (2016.01)
(Continued)

(52) U.S. Cl.
CPC .............. *A61B 90/50* (2016.02); *A61B 34/20* (2016.02); *A61B 34/25* (2016.02); *A61B 90/361* (2016.02); *G02B 27/0172* (2013.01); *G06T 7/74* (2017.01); *G06V 20/20* (2022.01); *A61B 2034/2055* (2016.02); *A61B 2034/2065* (2016.02); *A61B 2090/365* (2016.02); *G06T 2215/16* (2013.01)

(58) Field of Classification Search
CPC ....... A61B 34/20; A61B 34/25; A61B 90/361; A61B 2034/2055; A61B 2034/2065; A61B 2090/365; G06T 7/74; G06T 2215/16; G02B 27/0172

USPC .......................................................... 345/80
See application file for complete search history.

(56) References Cited

U.S. PATENT DOCUMENTS

| 4,150,293 | A | 4/1979 | Franke |
| 4,722,056 | A | 1/1988 | Roberts et al. |
(Continued)

FOREIGN PATENT DOCUMENTS

| JP | 2013542462 A | 11/2013 |
| WO | 2018203304 A1 | 11/2018 |

OTHER PUBLICATIONS

US 8,231,638 B2, 07/2012, Swarup et al. (withdrawn)

*Primary Examiner* — Mark Edwards

(57) ABSTRACT

A surgical system includes an AR headset and a AR headset controller. The AR headset is configured to be worn by a user during a surgical procedure and has a see-through display screen configured to display an AR image and to allow at least a portion of a real-world scene to pass therethrough for viewing by the user. The AR headset also includes an opacity filter positioned between at least one of the user's eyes and the real-world scene when the see-through display screen is viewed by the user. The opacity filter provides opaqueness to light from the real-world scene. The AR headset controller communicates with a navigation controller to receive navigation information from the navigation controller which provides guidance to the user during the surgical procedure on an anatomical structure, and generates the AR image based on the navigation information for display on the see-through display screen.

20 Claims, 26 Drawing Sheets

(51) Int. Cl.
  *A61B 34/20* (2016.01)
  *A61B 90/00* (2016.01)
  *G02B 27/01* (2006.01)
  *G06T 7/73* (2017.01)
  *G06V 20/20* (2022.01)

(56) References Cited

U.S. PATENT DOCUMENTS

| | | |
|---|---|---|
| 5,246,010 A | 9/1993 | Gazzara et al. |
| 5,354,314 A | 10/1994 | Hardy et al. |
| 5,397,323 A | 3/1995 | Taylor et al. |
| 5,526,812 A | 6/1996 | Dumoulin et al. |
| 5,598,453 A | 1/1997 | Baba et al. |
| 5,740,802 A | 4/1998 | Nafis et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,961,456 A | 10/1999 | Gildenberg |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,226,548 B1 | 5/2001 | Foley et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,349,001 B1 | 2/2002 | Spitzer |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,503,195 B1 | 1/2003 | Keller et al. |
| 6,507,751 B2 | 1/2003 | Blume et al. |
| 6,535,756 B1 | 3/2003 | Simon et al. |
| 6,544,176 B2 | 4/2003 | Mikus et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,725,080 B2 | 4/2004 | Melkent et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,324 B2 | 2/2005 | Sauer et al. |
| 6,856,826 B2 | 2/2005 | Seeley et al. |
| 6,856,827 B2 | 2/2005 | Seeley et al. |
| 6,867,753 B2 | 3/2005 | Chinthammit et al. |
| 6,879,880 B2 | 4/2005 | Nowlin et al. |
| 6,892,090 B2 | 5/2005 | Verard et al. |
| 6,919,867 B2 | 7/2005 | Sauer |
| 6,920,347 B2 | 7/2005 | Simon et al. |
| 6,922,632 B2 | 7/2005 | Foxlin |
| 6,947,786 B2 | 9/2005 | Simon et al. |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,050,845 B2 | 5/2006 | Vilsmeier |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,176,936 B2 | 2/2007 | Sauer et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,480,402 B2 | 1/2009 | Bar-Zohar et al. |
| 7,493,153 B2 | 2/2009 | Ahmed et al. |
| 7,505,617 B2 | 3/2009 | Fu et al. |
| 7,533,892 B2 | 5/2009 | Schena et al. |

(56) References Cited

U.S. PATENT DOCUMENTS

| | | |
|---|---|---|
| 7,542,791 B2 | 6/2009 | Mire et al. |
| 7,555,331 B2 | 6/2009 | Viswanathan |
| 7,567,834 B2 | 7/2009 | Clayton et al. |
| 7,570,791 B2 | 8/2009 | Frank et al. |
| 7,594,912 B2 | 9/2009 | Cooper et al. |
| 7,599,730 B2 | 10/2009 | Hunter et al. |
| 7,605,826 B2 | 10/2009 | Sauer |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,774,044 B2 | 8/2010 | Sauer et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Mswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Akin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Arkin et al. |
| 7,935,130 B2 | 5/2011 | Williams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,987,001 B2 | 7/2011 | Teichman et al. |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,106,905 B2 | 1/2012 | Markowitz et al. |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban et al. |
| 8,208,708 B2 | 6/2012 | Homan et al. |
| 8,208,988 B2 | 6/2012 | Jenser |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Arkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,314,815 B2 | 11/2012 | Navab et al. |
| 8,320,991 B2 | 11/2012 | Jascob et al. |
| 8,325,873 B2 | 12/2012 | Helm et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |

(56) References Cited

U.S. PATENT DOCUMENTS

| | | |
|---|---|---|
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,427,527 B2 | 4/2013 | Visser et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,136 B1 | 8/2013 | Sun et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,509,503 B2 | 8/2013 | Nahum et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Issacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos De La Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,672,836 B2 | 3/2014 | Higgins et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,774,363 B2 | 7/2014 | Van Den Houten et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,784,443 B2 | 7/2014 | Tripathi |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,842,893 B2 | 9/2014 | Teichman et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,878,900 B2 | 11/2014 | Yang et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,891,847 B2 | 11/2014 | Helm et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,938,283 B2 | 1/2015 | Zentgraf et al. |
| 8,938,301 B2 | 1/2015 | Hagedorn |
| 8,945,140 B2 | 2/2015 | Hubschman et al. |
| 8,948,935 B1 | 2/2015 | Peeters |
| 8,964,934 B2 | 2/2015 | Ein-Gal |

(56) References Cited

U.S. PATENT DOCUMENTS

| | | |
|---|---|---|
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,095,252 B2 | 8/2015 | Popovic |
| 9,105,207 B2 | 8/2015 | Leung |
| 9,107,683 B2 | 8/2015 | Hourtash et al. |
| 9,119,670 B2 | 9/2015 | Yang et al. |
| 9,123,155 B2 | 9/2015 | Cunningham et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,232,982 B2 | 1/2016 | Soler et al. |
| 9,265,468 B2 | 2/2016 | Rai et al. |
| 9,289,267 B2 | 3/2016 | Sauer et al. |
| 9,295,435 B2 | 3/2016 | Florent et al. |
| 9,308,050 B2 | 4/2016 | Kostrzewski et al. |
| 9,333,361 B2 | 5/2016 | Li et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,436,993 B1 | 9/2016 | Stolka et al. |
| 9,439,556 B2 | 9/2016 | Pandya et al. |
| 9,492,235 B2 | 11/2016 | Hourtash et al. |
| 9,492,241 B2 | 11/2016 | Jaskowicz et al. |
| 9,498,132 B2 | 11/2016 | Maier-Hein et al. |
| 9,538,962 B1 | 1/2017 | Hannaford et al. |
| 9,547,940 B1 | 1/2017 | Sun et al. |
| 9,554,866 B2 | 1/2017 | Cunningham et al. |
| 9,563,266 B2 | 2/2017 | Banerjee et al. |
| 9,576,106 B2 | 2/2017 | Ahmad |
| 9,592,096 B2 | 3/2017 | Maillet et al. |
| 9,626,805 B2 | 4/2017 | Lampotang et al. |
| 9,645,379 B2 | 5/2017 | Ren et al. |
| 9,681,925 B2 | 6/2017 | Azar et al. |
| 9,707,400 B2 | 7/2017 | Grenz et al. |
| 9,750,465 B2 | 9/2017 | Engel et al. |
| 9,757,203 B2 | 9/2017 | Hourtash et al. |
| 9,767,608 B2 | 9/2017 | Lee et al. |
| 9,773,312 B2 | 9/2017 | Lee |
| 9,788,756 B2 | 10/2017 | Demmer |
| 9,795,282 B2 | 10/2017 | Sholev et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,833,254 B1 | 12/2017 | Barral et al. |
| 9,835,862 B1 | 12/2017 | Zhou et al. |
| 9,839,365 B1 | 12/2017 | Homyk et al. |
| 9,848,922 B2 | 12/2017 | Tohmeh et al. |
| 9,855,103 B2 | 1/2018 | Tsekos et al. |
| 9,892,564 B1 | 2/2018 | Cvetko et al. |
| 9,895,063 B1 | 2/2018 | Hannaford et al. |
| 9,898,662 B2 | 2/2018 | Tsuda et al. |
| 9,911,187 B2 | 3/2018 | Steinle et al. |
| 9,925,011 B2 | 3/2018 | Gombert et al. |
| 9,925,013 B2 | 3/2018 | Dell et al. |
| 9,928,629 B2 | 3/2018 | Benishti et al. |
| 9,931,025 B1 | 4/2018 | Graetzel et al. |
| 9,931,040 B2 | 4/2018 | Homyk et al. |
| 9,949,637 B1 | 4/2018 | Wong et al. |
| 9,970,955 B1 | 5/2018 | Homyk et al. |
| 9,980,698 B2 | 5/2018 | Bakker et al. |
| 10,010,373 B2 | 7/2018 | Canfield et al. |
| 10,010,379 B1 | 7/2018 | Gibby et al. |
| 10,013,808 B2 | 7/2018 | Jones et al. |
| 10,016,243 B2 | 7/2018 | Esterberg |
| 10,034,717 B2 | 7/2018 | Miller et al. |
| 10,052,170 B2 | 8/2018 | Saget et al. |
| 10,073,515 B2 | 9/2018 | Awdeh |
| 10,092,164 B2 | 10/2018 | Sholev et al. |
| 10,092,237 B2 | 10/2018 | Wong et al. |
| 10,092,361 B2 | 10/2018 | Ferro et al. |
| 10,105,187 B2 | 10/2018 | Corndorf et al. |
| 10,152,789 B2 | 12/2018 | Carnes et al. |
| 10,152,796 B2 | 12/2018 | Guo et al. |
| 10,154,239 B2 | 12/2018 | Casas |
| 10,163,252 B2 | 12/2018 | Yun et al. |
| 10,166,019 B2 | 1/2019 | Nawana et al. |
| 10,176,642 B2 | 1/2019 | Tran et al. |
| 10,191,615 B2 | 1/2019 | Helm et al. |
| 10,194,990 B2 | 2/2019 | Amanatullah et al. |
| 10,195,076 B2 | 2/2019 | Fateh |
| 10,197,803 B2 | 2/2019 | Badiali et al. |
| 10,197,816 B2 | 2/2019 | Waisman et al. |
| 10,226,298 B2 | 3/2019 | Ourselin et al. |
| 10,231,784 B2 | 3/2019 | Hettrick et al. |
| 10,235,737 B2 | 3/2019 | Cheatham, III et al. |
| 10,242,292 B2 | 3/2019 | Zisimopoulos et al. |
| 10,251,714 B2 | 4/2019 | Carnes et al. |
| 10,258,426 B2 | 4/2019 | Silva et al. |
| 10,265,138 B2 | 4/2019 | Choudhry et al. |
| 10,275,927 B2 | 4/2019 | Kuhn et al. |
| 10,278,726 B2 | 5/2019 | Barth et al. |
| 10,285,765 B2 | 5/2019 | Sachs et al. |
| 10,292,780 B2 | 5/2019 | Park |
| 10,360,730 B2 | 7/2019 | Hasegwa |
| 10,366,489 B2 | 7/2019 | Boettger et al. |
| 10,376,318 B2 | 8/2019 | Tsusaka et al. |
| 10,379,048 B2 | 8/2019 | Wang et al. |
| 10,383,654 B2 | 8/2019 | Yilmaz et al. |
| 10,390,780 B2 | 8/2019 | Han et al. |
| 10,390,890 B2 | 8/2019 | Jagga |
| 10,390,891 B2 | 8/2019 | Govari et al. |
| 10,398,514 B2 | 9/2019 | Ryan et al. |
| 10,405,927 B1 | 9/2019 | Lang |
| 10,412,377 B2 | 9/2019 | Forthmann et al. |
| 10,413,363 B2 | 9/2019 | Fahim et al. |
| 10,426,339 B2 | 10/2019 | Papac |
| 10,426,345 B2 | 10/2019 | Shekhar et al. |
| 10,426,554 B2 | 10/2019 | Siewerdsen et al. |
| 10,431,008 B2 | 10/2019 | Djajadiningrat et al. |
| 10,432,913 B2 | 10/2019 | Shokri et al. |
| 10,433,915 B2 | 10/2019 | Isaacs et al. |
| 10,448,003 B2 | 10/2019 | Gafenberg |
| 11,067,809 B1 * | 7/2021 | Sears .................. G02F 1/13475 |
| 2001/0036302 A1 | 11/2001 | Miller |
| 2002/0035321 A1 | 3/2002 | Bucholz et al. |
| 2003/0179308 A1 | 9/2003 | Zamorano et al. |
| 2003/0210812 A1 | 11/2003 | Khamene et al. |
| 2004/0068172 A1 | 4/2004 | Nowinski et al. |
| 2004/0076259 A1 | 4/2004 | Jensen et al. |
| 2004/0254454 A1 | 12/2004 | Kockro |
| 2005/0054910 A1 | 3/2005 | Tremblay et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2005/0215879 A1 | 9/2005 | Chuanggui |
| 2006/0100610 A1 | 5/2006 | Wallace et al. |
| 2006/0173329 A1 | 8/2006 | Marquart et al. |
| 2006/0176242 A1 | 8/2006 | Jaramaz et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2006/0293557 A1 | 12/2006 | Chuanggui et al. |
| 2007/0015987 A1 | 1/2007 | Benlloch Baviera et al. |
| 2007/0021738 A1 | 1/2007 | Hasset et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167702 A1 | 7/2007 | Hasser et al. |
| 2007/0167712 A1 | 7/2007 | Keglovich et al. |
| 2007/0233238 A1 | 10/2007 | Huynh et al. |
| 2007/0236514 A1 | 10/2007 | Agusanto et al. |
| 2007/0238981 A1 | 10/2007 | Zhu et al. |
| 2007/0248261 A1 | 10/2007 | Zhou et al. |
| 2008/0004523 A1 | 1/2008 | Jensen |
| 2008/0013809 A1 | 1/2008 | Zhu et al. |
| 2008/0033283 A1 | 2/2008 | Dellaca et al. |

(56) References Cited

U.S. PATENT DOCUMENTS

| | | |
|---|---|---|
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | von Jako |
| 2008/0109012 A1 | 5/2008 | Falco et al. |
| 2008/0123910 A1 | 5/2008 | Zhu |
| 2008/0144906 A1 | 6/2008 | Allred et al. |
| 2008/0161680 A1 | 7/2008 | von Jako et al. |
| 2008/0161682 A1 | 7/2008 | Kendrick et al. |
| 2008/0177203 A1 | 7/2008 | von Jako |
| 2008/0183068 A1 | 7/2008 | Carls et al. |
| 2008/0183074 A1 | 7/2008 | Carls et al. |
| 2008/0183188 A1 | 7/2008 | Carls et al. |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0243142 A1 | 10/2008 | Gildenberg |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0210902 A1 | 8/2010 | Navab et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Arkin et al. |
| 2011/0224686 A1 | 9/2011 | Arkin et al. |
| 2011/0224687 A1 | 9/2011 | Arkin et al. |
| 2011/0224688 A1 | 9/2011 | Arkin et al. |
| 2011/0224689 A1 | 9/2011 | Arkin et al. |
| 2011/0224825 A1 | 9/2011 | Arkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0059378 A1 | 3/2012 | Farrell |
| 2012/0068913 A1* | 3/2012 | Bar-Zeev ............... G09G 3/001 345/8 |
| 2012/0071753 A1 | 3/2012 | Hunter et al. |
| 2012/0092328 A1* | 4/2012 | Flaks ................... G06V 20/10 345/419 |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0203067 A1 | 8/2012 | Higgins et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2012/0302875 A1 | 11/2012 | Kohring |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0050432 A1 | 2/2013 | Perez et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211232 A1 | 8/2013 | Murphy et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0267838 A1 | 10/2013 | Fronk et al. |
| 2013/0272488 A1 | 10/2013 | Bailey et al. |
| 2013/0272489 A1 | 10/2013 | Dickman et al. |
| 2013/0274596 A1 | 10/2013 | Azizian et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0022283 A1 | 1/2014 | Chan et al. |
| 2014/0031664 A1 | 1/2014 | Kang et al. |
| 2014/0044333 A1 | 2/2014 | Barth, Jr. et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Avallee et al. |

(56) References Cited

U.S. PATENT DOCUMENTS

| | | |
|---|---|---|
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0139405 A1 | 5/2014 | Ribble et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0206994 A1 | 7/2014 | Jain et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0347353 A1 | 11/2014 | Popovic et al. |
| 2014/0364720 A1 | 12/2014 | Darrow et al. |
| 2014/0371577 A1 | 12/2014 | Maillet et al. |
| 2015/0031990 A1 | 1/2015 | Boctor et al. |
| 2015/0039034 A1 | 2/2015 | Frankel et al. |
| 2015/0073265 A1 | 3/2015 | Popovic et al. |
| 2015/0084990 A1 | 3/2015 | Laor |
| 2015/0085970 A1 | 3/2015 | Bouhnik et al. |
| 2015/0112126 A1 | 4/2015 | Popovic et al. |
| 2015/0146847 A1 | 5/2015 | Liu |
| 2015/0146946 A1 | 5/2015 | Elhawary et al. |
| 2015/0150524 A1 | 6/2015 | Yorkston et al. |
| 2015/0196261 A1 | 7/2015 | Funk |
| 2015/0201892 A1 | 7/2015 | Hummel et al. |
| 2015/0213633 A1 | 7/2015 | Chang et al. |
| 2015/0230689 A1 | 8/2015 | Blohm et al. |
| 2015/0238276 A1 | 8/2015 | Atarot et al. |
| 2015/0248793 A1 | 9/2015 | Abovitz et al. |
| 2015/0305828 A1 | 10/2015 | Park et al. |
| 2015/0335480 A1 | 11/2015 | Alvarez et al. |
| 2015/0342647 A1 | 12/2015 | Frankel et al. |
| 2015/0366628 A1 | 12/2015 | Ingmanson |
| 2016/0005194 A1 | 1/2016 | Schretter et al. |
| 2016/0015469 A1 | 1/2016 | Goshayesh et al. |
| 2016/0015470 A1 | 1/2016 | Border |
| 2016/0018640 A1 | 1/2016 | Haddick et al. |
| 2016/0018641 A1 | 1/2016 | Haddick et al. |
| 2016/0018642 A1 | 1/2016 | Haddick et al. |
| 2016/0019715 A1 | 1/2016 | Haddick et al. |
| 2016/0019716 A1 | 1/2016 | Huang et al. |
| 2016/0019719 A1 | 1/2016 | Osterhout et al. |
| 2016/0021304 A1 | 1/2016 | Osterhout |
| 2016/0022125 A1 | 1/2016 | Nicolau et al. |
| 2016/0086380 A1 | 3/2016 | Vayser et al. |
| 2016/0163105 A1 | 6/2016 | Hong et al. |
| 2016/0166329 A1 | 6/2016 | Langan et al. |
| 2016/0235480 A1 | 8/2016 | Scholl et al. |
| 2016/0249989 A1 | 9/2016 | Devam et al. |
| 2016/0249990 A1 | 9/2016 | Glozman et al. |
| 2016/0287337 A1 | 10/2016 | Aram et al. |
| 2016/0302871 A1 | 10/2016 | Gregerson et al. |
| 2016/0317119 A1 | 11/2016 | Tahmasebi Maraghoosh et al. |
| 2016/0320322 A1 | 11/2016 | Suzuki |
| 2016/0324598 A1 | 11/2016 | Bothorel et al. |
| 2016/0331335 A1 | 11/2016 | Gregerson et al. |
| 2016/0360117 A1 | 12/2016 | Elefteriu et al. |
| 2017/0007351 A1 | 1/2017 | Yu |
| 2017/0035517 A1 | 2/2017 | Geri et al. |
| 2017/0053437 A1 | 2/2017 | Ye et al. |
| 2017/0099479 A1 | 4/2017 | Browd et al. |
| 2017/0119471 A1 | 5/2017 | Winner et al. |
| 2017/0119474 A1 | 5/2017 | Kronman |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0151034 A1 | 6/2017 | Oda et al. |
| 2017/0156816 A1 | 6/2017 | Ibrahim |
| 2017/0172381 A1 | 6/2017 | Morimoto |
| 2017/0172663 A1 | 6/2017 | Popovic et al. |
| 2017/0202624 A1 | 7/2017 | Atarot et al. |
| 2017/0202629 A1 | 7/2017 | Maillet et al. |
| 2017/0202633 A1 | 7/2017 | Liu |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0224427 A1 | 8/2017 | Lavallee et al. |
| 2017/0231710 A1 | 8/2017 | Scholl et al. |
| 2017/0231714 A1 | 8/2017 | Kosmecki et al. |
| 2017/0251900 A1 | 9/2017 | Hansen et al. |
| 2017/0256095 A1* | 9/2017 | Bani-Hashemi ... G02B 27/0172 |
| 2017/0258426 A1 | 9/2017 | Risher-Kelly et al. |
| 2017/0273549 A1 | 9/2017 | Nazareth et al. |
| 2017/0273748 A1 | 9/2017 | Hourtash et al. |
| 2017/0296277 A1 | 10/2017 | Hourtash et al. |
| 2017/0296292 A1 | 10/2017 | Mahmood et al. |
| 2017/0315364 A1 | 11/2017 | Masumoto |
| 2017/0322410 A1 | 11/2017 | Watson et al. |
| 2017/0323062 A1 | 11/2017 | Djajadiningrat et al. |
| 2017/0323481 A1* | 11/2017 | Tran ............... H04N 23/611 |
| 2017/0336870 A1 | 11/2017 | Everett et al. |
| 2017/0360493 A1 | 12/2017 | Zucher et al. |
| 2017/0367766 A1 | 12/2017 | Mahfouz |
| 2017/0367771 A1 | 12/2017 | Tako et al. |
| 2018/0021099 A1 | 1/2018 | Warner et al. |
| 2018/0032130 A1 | 2/2018 | Meglan |
| 2018/0042692 A1 | 2/2018 | Kim et al. |
| 2018/0049809 A1 | 2/2018 | Marti et al. |
| 2018/0071032 A1 | 3/2018 | De Almeida Barreto |
| 2018/0078316 A1 | 3/2018 | Schaewe et al. |
| 2018/0082480 A1 | 3/2018 | White et al. |
| 2018/0092698 A1 | 4/2018 | Chopra et al. |
| 2018/0092706 A1 | 4/2018 | Anderson et al. |
| 2018/0116724 A1 | 5/2018 | Gmeiner et al. |
| 2018/0116732 A1 | 5/2018 | Lin et al. |
| 2018/0125586 A1 | 5/2018 | Sela et al. |
| 2018/0140362 A1 | 5/2018 | Cali et al. |
| 2018/0158201 A1 | 6/2018 | Thompson et al. |
| 2018/0161102 A1 | 6/2018 | Wei et al. |
| 2018/0168730 A1 | 6/2018 | Nazy |
| 2018/0168741 A1 | 6/2018 | Swayze |
| 2018/0168769 A1 | 6/2018 | Wood et al. |
| 2018/0185100 A1* | 7/2018 | Weinstein ............ A61B 34/20 |
| 2018/0220100 A1* | 8/2018 | Ovchinnikov ........ G06F 3/0484 |
| 2018/0228555 A1 | 8/2018 | Charron et al. |
| 2018/0232925 A1 | 8/2018 | Frakes et al. |
| 2018/0233222 A1 | 8/2018 | Daley et al. |

(56) References Cited

U.S. PATENT DOCUMENTS

| | | |
|---|---|---|
| 2018/0235739 A1 | 8/2018 | Jahn |
| 2018/0247449 A1 | 8/2018 | Park et al. |
| 2018/0249912 A1 | 9/2018 | Schneider et al. |
| 2018/0256256 A1 | 9/2018 | May et al. |
| 2018/0263698 A1 | 9/2018 | Wang et al. |
| 2018/0263727 A1 | 9/2018 | Pellerito |
| 2018/0289428 A1 | 10/2018 | Lee et al. |
| 2018/0289983 A1 | 10/2018 | Fishman |
| 2018/0299675 A1 | 10/2018 | Benz et al. |
| 2018/0303377 A1 | 10/2018 | West et al. |
| 2018/0303558 A1 | 10/2018 | Thomas |
| 2018/0303667 A1 | 10/2018 | Peyman |
| 2018/0310811 A1 | 11/2018 | Meglan et al. |
| 2018/0310831 A1 | 11/2018 | Cheng et al. |
| 2018/0310875 A1 | 11/2018 | Meglan et al. |
| 2018/0325604 A1 | 11/2018 | Atarot et al. |
| 2018/0325618 A1 | 11/2018 | Justin et al. |
| 2018/0333073 A1 | 11/2018 | Hill et al. |
| 2018/0333207 A1 | 11/2018 | Barrera |
| 2018/0333208 A1 | 11/2018 | Kotian et al. |
| 2018/0344266 A1 | 12/2018 | Altmann |
| 2018/0344408 A1 | 12/2018 | Rotilio et al. |
| 2018/0357825 A1 | 12/2018 | Hoffmann et al. |
| 2018/0360310 A1 | 12/2018 | Berlin |
| 2018/0368930 A1 | 12/2018 | Esterberg et al. |
| 2019/0000564 A1 | 1/2019 | Navab et al. |
| 2019/0000570 A1 | 1/2019 | Esterberg et al. |
| 2019/0008592 A1 | 1/2019 | Thienphrapa et al. |
| 2019/0011709 A1 | 1/2019 | Yadav et al. |
| 2019/0015162 A1 | 1/2019 | Abhari et al. |
| 2019/0015167 A1 | 1/2019 | Draelos et al. |
| 2019/0029757 A1 | 1/2019 | Roh et al. |
| 2019/0035156 A1 | 1/2019 | Wei et al. |
| 2019/0038362 A1 | 2/2019 | Nash et al. |
| 2019/0046276 A1 | 2/2019 | Inglese et al. |
| 2019/0050665 A1 | 2/2019 | Sakuragi |
| 2019/0053851 A1 | 2/2019 | Sieminonow et al. |
| 2019/0053855 A1 | 2/2019 | Sieminonow et al. |
| 2019/0053858 A1 | 2/2019 | Kapoo et al. |
| 2019/0054632 A1 | 2/2019 | Grafenberg et al. |
| 2019/0059773 A1 | 2/2019 | Laughlin et al. |
| 2019/0066260 A1 | 2/2019 | Suehling et al. |
| 2019/0066390 A1 | 2/2019 | Vogel et al. |
| 2019/0069962 A1 | 3/2019 | Tabandeh et al. |
| 2019/0076194 A1 | 3/2019 | Jang |
| 2019/0080515 A1 | 3/2019 | Geri et al. |
| 2019/0088162 A1 | 3/2019 | Meglan |
| 2019/0090955 A1 | 3/2019 | Singh et al. |
| 2019/0099221 A1 | 4/2019 | Schmidt et al. |
| 2019/0104919 A1 | 4/2019 | Shelton, IV et al. |
| 2019/0108654 A1 | 4/2019 | Lasserre et al. |
| 2019/0117190 A1 | 4/2019 | Djajadonongrat |
| 2019/0122443 A1 | 4/2019 | Stocker |
| 2019/0125361 A1 | 5/2019 | Shelton, IV et al. |
| 2019/0125454 A1 | 5/2019 | Shelton, IV et al. |
| 2019/0142520 A1 | 5/2019 | Vandyken |
| 2019/0159841 A1 | 5/2019 | Abhari et al. |
| 2019/0167148 A1 | 6/2019 | Durfee et al. |
| 2019/0175058 A1 | 6/2019 | Godwin et al. |
| 2019/0180441 A1 | 6/2019 | Peng et al. |
| 2019/0183576 A1 | 6/2019 | Fahim et al. |
| 2019/0183590 A1 | 6/2019 | Hladio et al. |
| 2019/0192230 A1 | 6/2019 | Siemionow et al. |
| 2019/0192232 A1 | 6/2019 | Altmann et al. |
| 2019/0200844 A1 | 7/2019 | Shelton, IV et al. |
| 2019/0200977 A1 | 7/2019 | Shelton, IV et al. |
| 2019/0201104 A1 | 7/2019 | Shelton, IV et al. |
| 2019/0201106 A1 | 7/2019 | Siemionow et al. |
| 2019/0201158 A1 | 7/2019 | Shelton, IV et al. |
| 2019/0206062 A1 | 7/2019 | Matsuoka et al. |
| 2019/0206134 A1 | 7/2019 | Devam et al. |
| 2019/0206565 A1 | 7/2019 | Shelton, IV |
| 2019/0209241 A1 | 7/2019 | Begg |
| 2019/0214126 A1 | 7/2019 | Goetz |
| 2019/0216572 A1 | 7/2019 | Wang et al. |
| 2019/0223746 A1 | 7/2019 | Intrator |
| 2019/0231220 A1 | 8/2019 | Refai et al. |
| 2019/0231443 A1 | 8/2019 | McGinley et al. |
| 2019/0239850 A1 | 8/2019 | Dalvin et al. |
| 2019/0254753 A1 | 8/2019 | Johnson et al. |
| 2019/0274762 A1 | 9/2019 | Kim et al. |
| 2019/0282099 A1 | 9/2019 | Themelis |
| 2019/0307516 A1 | 10/2019 | Schotzko et al. |
| 2021/0192759 A1* | 6/2021 | Lang ........................ G06T 3/40 |

\* cited by examiner

US 11,992,373 B2

AUGMENTED REALITY HEADSET WITH VARIED OPACITY FOR NAVIGATED ROBOTIC SURGERY

FIELD

The present disclosure relates to medical devices and systems, and more particularly, computer assisted navigation in surgery using robotic surgical systems.

BACKGROUND

Computer assisted navigation in surgery provides surgeons with enhanced visualization of surgical instruments with respect to radiographic images of the patient's anatomy. However, existing navigation systems have limitations on usability and ergonomics for the surgeon, including 1) necessitating that the surgeon turn his/her head away from the patient and surgical instrument to view navigation information, 2) imposing reliance on other personnel to operate software functions of various equipment in the operating room, and 3) intermittent pauses with providing navigation during surgery while personnel and/or objects obstruct the ability of a tracking component to track poses of the patient, the robot, and surgical instruments.

SUMMARY

Various embodiments disclosed herein are directed to improvements in computer assisted navigation during surgery. An augmented reality (AR) headset is operatively connected to the surgical system to provide an interactive environment through which a surgeon, assistant, and/or other personnel can view and manipulate patient images, view and manipulate computer generated navigation information, and/or control surgical equipment in an operating room.

Some embodiments of the present disclosure are directed to a surgical system that includes an AR headset and a AR headset controller. The AR headset is configured to be worn by a user during a surgical procedure and has a see-through display screen configured to display an AR image and to allow at least a portion of a real-world scene to pass therethrough for viewing by the user. The AR headset also includes an opacity filter positioned between at least one of the user's eyes and the real-world scene when the see-through display screen is viewed by the user. The opacity filter is configured to provide opaqueness to light from the real-world scene. The AR headset controller is configured to communicate with a navigation controller to receive navigation information from the navigation controller which provides guidance to the user during the surgical procedure on an anatomical structure, and configured to generate the AR image based on the navigation information for display on the see-through display screen.

Some embodiments of the present disclosure are more generally directed to an AR headset that includes a see-through display screen and an opacity filter. The see-through display screen is configured to display an AR image and to allow at least a portion of a real-world scene to pass therethrough for viewing by a user. The opacity filter is configured to be positioned between at least one of the user's eyes and the real-world scene while the user is wearing the AR headset to view the see-through display screen. The opacity filter is also configured to provide opaqueness to light from the real-world scene.

Other surgical systems, AR headsets, and corresponding methods and computer program products according to embodiments will be or become apparent to one with skill in the art upon review of the following drawings and detailed description. It is intended that all such surgical systems, AR headsets, and corresponding methods and computer program products be included within this description, be within the scope of the present disclosure, and be protected by the accompanying claims. Moreover, it is intended that all embodiments disclosed herein can be implemented separately or combined in any way and/or combination.

BRIEF DESCRIPTION OF THE DRAWINGS

The accompanying drawings, which are included to provide a further understanding of the disclosure and are incorporated in a constitute a part of this application, illustrate certain non-limiting embodiments of inventive concepts. In the drawings.

DETAILED DESCRIPTION

Inventive concepts will now be described more fully hereinafter with reference to the accompanying drawings, in which examples of embodiments of inventive concepts are shown. Inventive concepts may, however, be embodied in many different forms and should not be construed as limited to the embodiments set forth herein. Rather, these embodiments are provided so that this disclosure will be thorough and complete, and will fully convey the scope of various present inventive concepts to those skilled in the art. It should also be noted that these embodiments are not mutually exclusive. Components from one embodiment may be tacitly assumed to be present or used in another embodiment.

Various embodiments disclosed herein are directed to improvements in computer assisted navigation during surgery. An augmented reality (AR) headset is operatively connected to the surgical system and configured to provide an interactive environment through which a surgeon, assistant, and/or other personnel can view and select among patient images, view and select among computer generated surgery navigation information, and/or control surgical equipment in the operating room.

Figure 1:
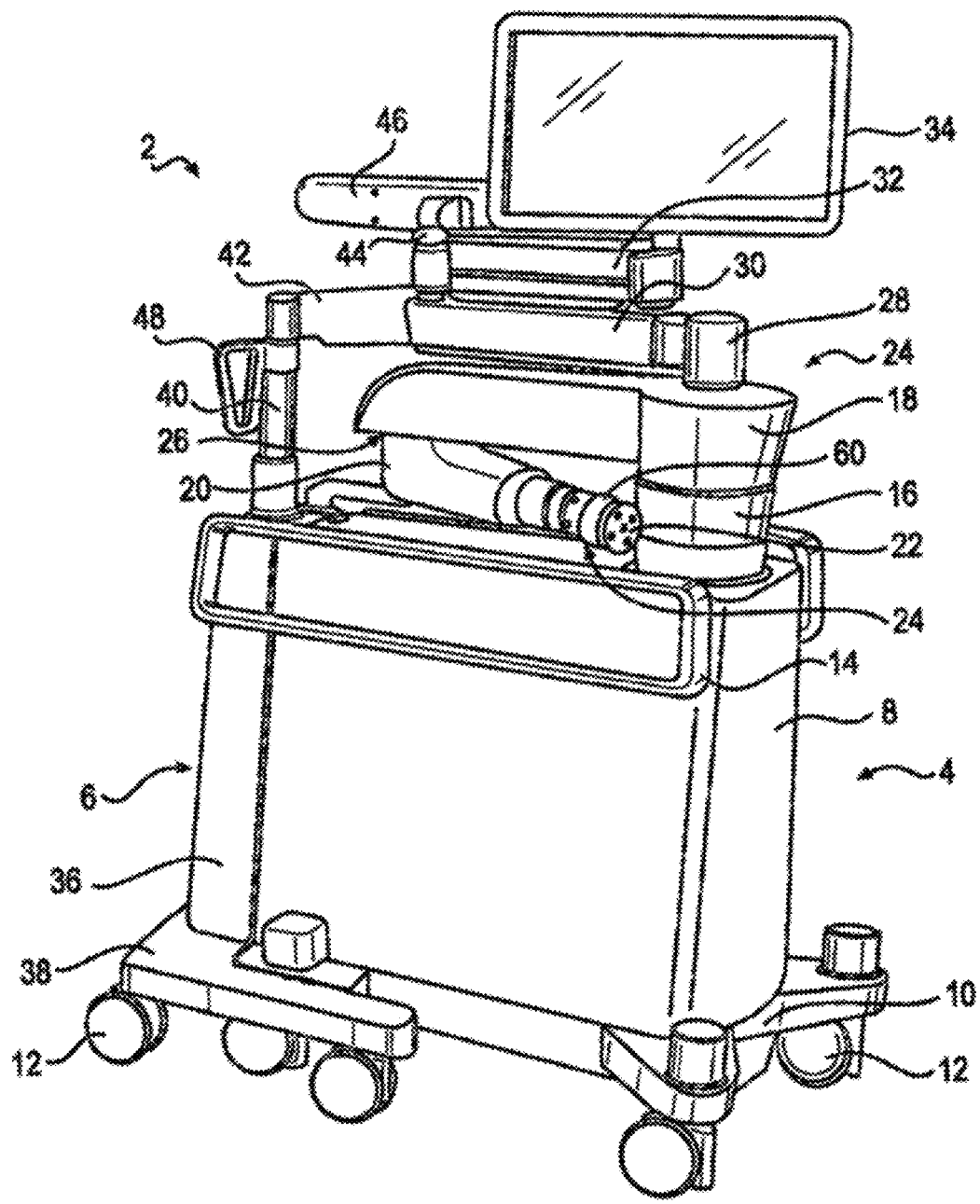
FIG. 1 illustrates an embodiment of a surgical system according to some embodiments of the present disclosure.

FIG. 1 illustrates an embodiment of a surgical system 2 according to some embodiments of the present disclosure. Prior to performance of an orthopedic or other surgical procedure, a three-dimensional ("3D") image scan may be taken of a planned surgical area of a patient using, e.g., the C-Arm imaging device 104 of FIG. 10 or O-Arm imaging device 106 of FIG. 11, or from another medical imaging device such as a computed tomography (CT) image or MRI. This scan can be taken pre-operatively (e.g. few weeks before procedure, most common) or intra-operatively. However, any known 3D or 2D image scan may be used in accordance with various embodiments of the surgical system 2. The image scan is sent to a computer platform in communication with the surgical system 2, such as the computer platform 910 of the surgical system 900 (FIG. 9) which may include the camera tracking system 6, the surgical robot 4 (e.g., robot 2 in FIG. 1), imaging devices (e.g., C-Arm 104, O-Arm 106, etc.), and an image database 950 for storing image scans of patients. A surgeon reviewing the image scan(s) on a display device of the computer platform 910 (FIG. 9) generates a surgical plan defining a target pose for a surgical tool to be used during a surgical procedure on an anatomical structure of the patient. Example surgical tools, also referred to as tools, can include, without limitation, drills, screw drivers, retractors, and implants such as a screws, spacers, interbody fusion devices, plates, rods, etc. In some embodiments, the surgical plan defining the target plane is planned on the 3D image scan displayed on a display device.

As used herein, the term "pose" refers to the position and/or the rotational angle of one object (e.g., dynamic reference array, end effector, surgical tool, anatomical structure, etc.) relative to another object and/or to a defined coordinate system. A pose may therefore be defined based on only the multidimensional position of one object relative to another object and/or to a defined coordinate system, only on the multidimensional rotational angles of the object relative to another object and/or to a defined coordinate system, or on a combination of the multidimensional position and the multidimensional rotational angles. The term "pose" therefore is used to refer to position, rotational angle, or combination thereof.

The surgical system 2 of FIG. 1 can assist surgeons during medical procedures by, for example, holding tools, aligning tools, using tools, guiding tools, and/or positioning tools for use. In some embodiments, surgical system 2 includes a surgical robot 4 and a camera tracking system 6. The ability to mechanically couple surgical robot 4 and camera tracking system 6 can allow for surgical system 2 to maneuver and move as a single unit, and allow surgical system 2 to have a small footprint in an area, allow easier movement through narrow passages and around turns, and allow storage within a smaller area.

A surgical procedure may begin with the surgical system 2 moving from medical storage to a medical procedure room. The surgical system 2 may be maneuvered through doorways, halls, and elevators to reach a medical procedure room. Within the room, the surgical system 2 may be physically separated into two separate and distinct systems, the surgical robot 4 and the camera tracking system 6. Surgical robot 4 may be positioned adjacent the patient at any suitable location to properly assist medical personnel. Camera tracking system 6 may be positioned at the base of the patient, at the patient shoulders, or any other location suitable to track the present pose and movement of the pose of tracks portions of the surgical robot 4 and the patient. Surgical robot 4 and camera tracking system 6 may be powered by an onboard power source and/or plugged into an external wall outlet.

Surgical robot 4 may be used to assist a surgeon by holding and/or using tools during a medical procedure. To properly utilize and hold tools, surgical robot 4 may rely on a plurality of motors, computers, and/or actuators to function properly. Illustrated in FIG. 1, robot body 8 may act as the structure in which the plurality of motors, computers, and/or actuators may be secured within surgical robot 4. Robot body 8 may also provide support for robot telescoping support arm 16. The size of robot body 8 may provide a solid platform supporting attached components, and may house, conceal, and protect the plurality of motors, computers, and/or actuators that may operate attached components.

Robot base 10 may act as a lower support for surgical robot 4. In some embodiments, robot base 10 may support robot body 8 and may attach robot body 8 to a plurality of powered wheels 12. This attachment to wheels may allow robot body 8 to move in space efficiently. Robot base 10 may run the length and width of robot body 8. Robot base 10 may be about two inches to about 10 inches tall. Robot base 10 may cover, protect, and support powered wheels 12.

In some embodiments, as illustrated in FIG. 1, at least one powered wheel 12 may be attached to robot base 10. Powered wheels 12 may attach to robot base 10 at any location. Each individual powered wheel 12 may rotate about a vertical axis in any direction. A motor may be disposed above, within, or adjacent to powered wheel 12. This motor may allow for surgical system 2 to maneuver into any location and stabilize and/or level surgical system 2. A rod, located within or adjacent to powered wheel 12, may be pressed into a surface by the motor. The rod, not pictured, may be made of any suitable metal to lift surgical system 2. The rod may lift powered wheel 10, which may lift surgical system 2, to any height required to level or otherwise fix the orientation of the surgical system 2 in relation to a patient. The weight of surgical system 2, supported through small contact areas by the rod on each wheel, prevents surgical system 2 from moving during a medical procedure. This rigid positioning may prevent objects and/or people from moving surgical system 2 by accident.

Moving surgical system 2 may be facilitated using robot railing 14. Robot railing 14 provides a person with the ability to move surgical system 2 without grasping robot body 8. As illustrated in FIG. 1, robot railing 14 may run the length of robot body 8, shorter than robot body 8, and/or may run longer the length of robot body 8. Robot railing 14 may further provide protection to robot body 8, preventing objects and or personnel from touching, hitting, or bumping into robot body 8.

Robot body 8 may provide support for a Selective Compliance Articulated Robot Arm, hereafter referred to as a "SCARA." A SCARA 24 may be beneficial to use within the surgical system 2 due to the repeatability and compactness of the robotic arm. The compactness of a SCARA may provide additional space within a medical procedure, which may allow medical professionals to perform medical procedures free of excess clutter and confining areas. SCARA 24 may comprise robot telescoping support 16, robot support arm 18, and/or robot arm 20. Robot telescoping support 16 may be disposed along robot body 8. As illustrated in FIG. 1, robot telescoping support 16 may provide support for the SCARA 24 and display 34. In some embodiments, robot telescoping support 16 may extend and contract in a vertical direction. The body of robot telescoping support 16 may be any width and/or height configured to support the stress and weight placed upon it.

In some embodiments, medical personnel may move SCARA 24 through a command submitted by the medical personnel. The command may originate from input received on display 34, a tablet, and/or an AR headset (e.g., headset 920 in FIG. 9) as will be explained in further detail below. The AR headset may eliminate the need for medical personnel to refer to any other display such as the display 34 or a tablet, which enables the SCARA 24 to be configured without the display 34 and/or the tablet. The command may be generated by the depression of a switch and/or the depression of a plurality of switches, and/or may be generated based on a hand gesture command and/or voice command that is sensed by the AR headset as will be explained in further detail below.

Figure 5:
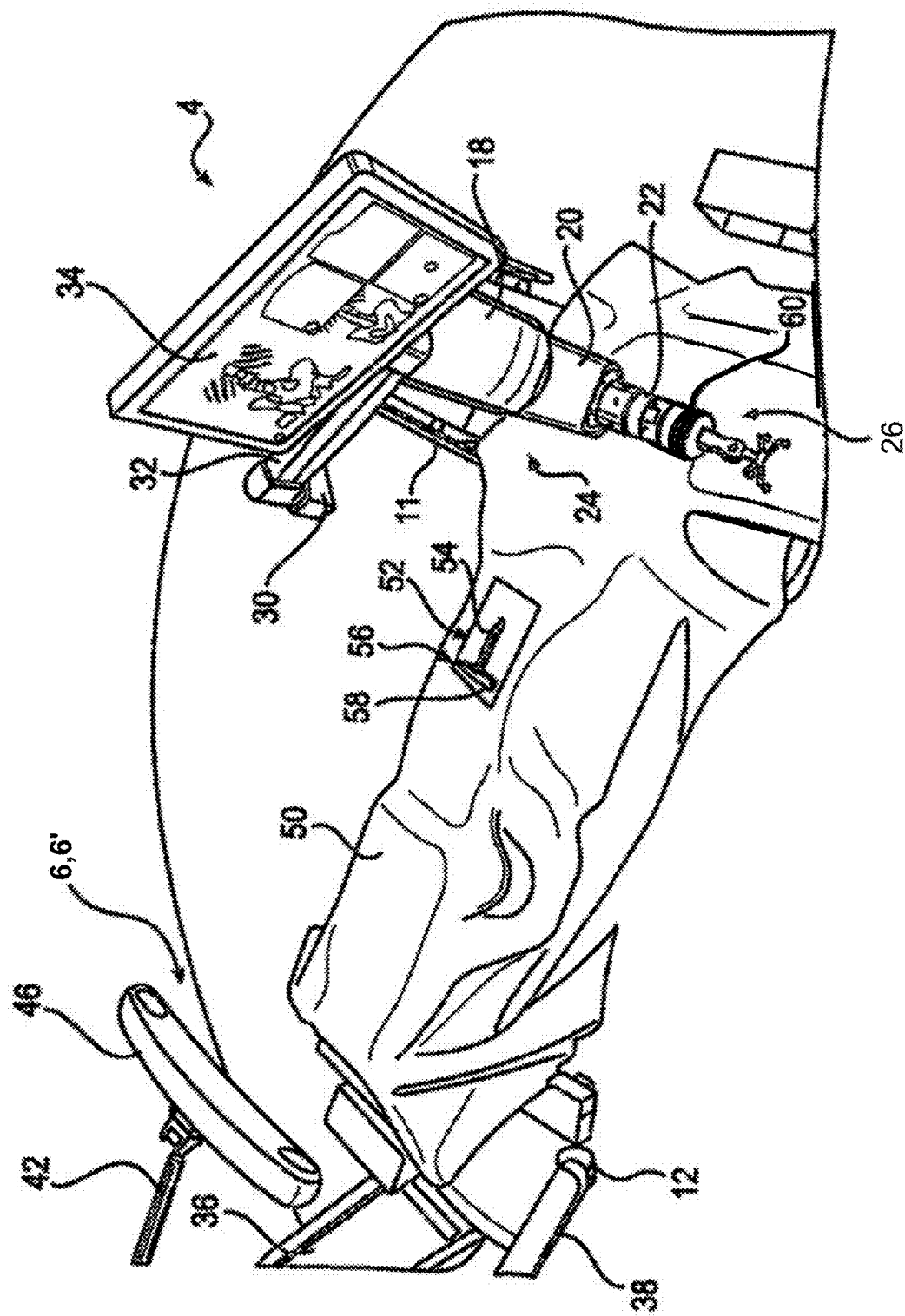
FIG. 5 illustrates a medical operation in which a surgical robot and a camera system are disposed around a patient.

As shown in FIG. 5, an activation assembly 60 may include a switch and/or a plurality of switches. The activation assembly 60 may be operable to transmit a move command to the SCARA 24 allowing an operator to manually manipulate the SCARA 24. When the switch, or plurality of switches, is depressed the medical personnel may have the ability to move SCARA 24 through applied hand movements. Alternatively or additionally, an operator may control movement of the SCARA 24 through hand gesture commands and/or voice commands that are sensed by the AR headset as will be explained in further detail below. Additionally, when the SCARA 24 is not receiving a command to move, the SCARA 24 may lock in place to prevent accidental movement by personnel and/or other objects. By locking in place, the SCARA 24 provides a solid platform through which the end effector 26 can guide a surgical tool during a medical procedure.

Robot support arm 18 can be connected to robot telescoping support 16 by various mechanisms. In some embodiments, best seen in FIGS. 1 and 2, robot support arm 18 rotates in any direction in regard to robot telescoping support 16. Robot support arm 18 may rotate three hundred and sixty degrees around robot telescoping support 16. Robot arm 20 may connect to robot support arm 18 at any suitable location and by various mechanisms that enable rotation in any direction relative to robot support arm 18. In one embodiment, the robot arm 20 can rotate three hundred and sixty degrees relative to the robot support arm 18. This free rotation allows an operator to position robot arm 20 according to a surgical plan.

Figure 4:
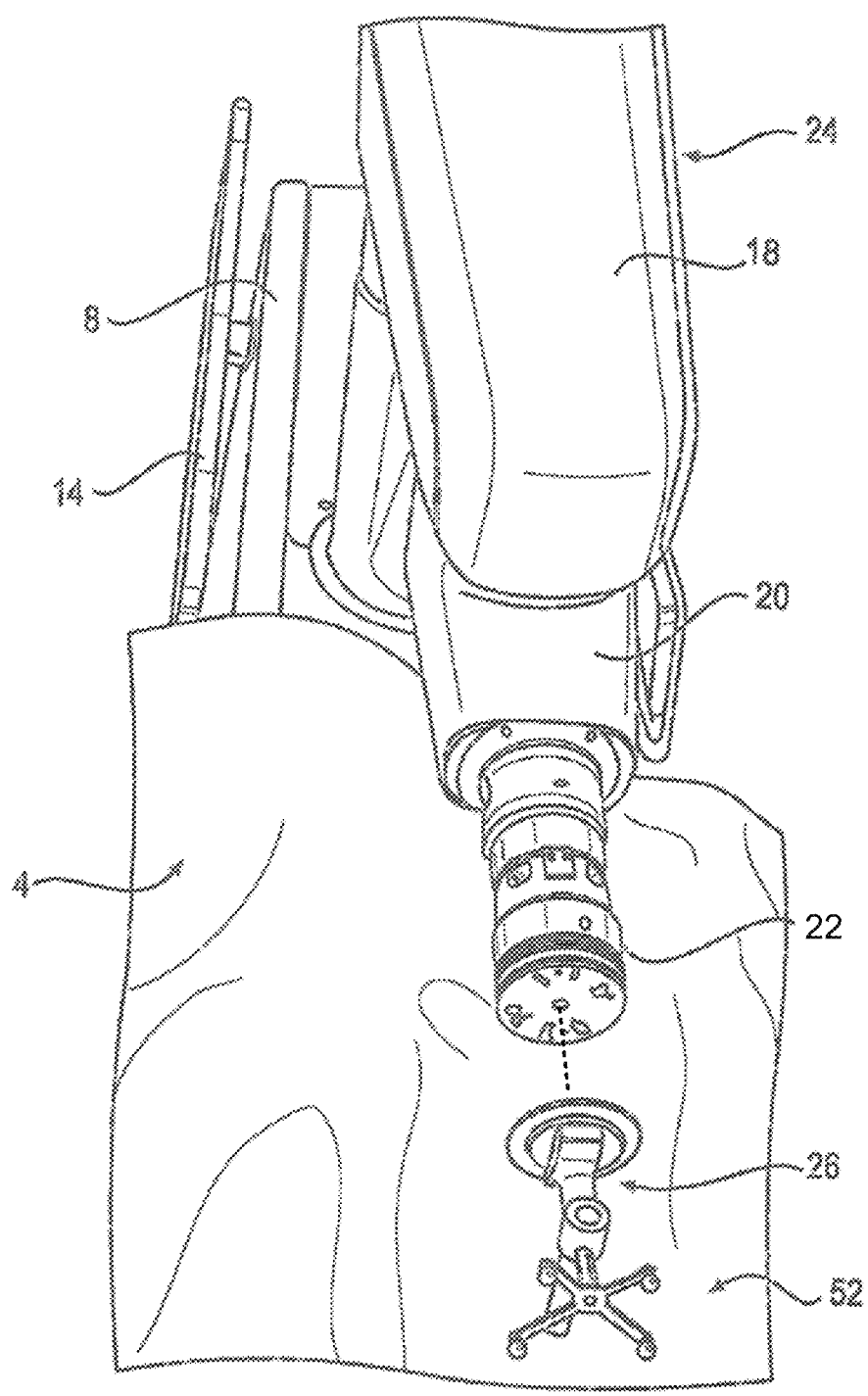
FIG. 4 illustrates an embodiment of an end effector that is connectable to a robot arm and configured according to some embodiments of the present disclosure.

The end effector 26 shown in FIGS. 4 and 5 may attach to robot arm 20 in any suitable location. The end effector 26 can be configured to attach to an end effector coupler 22 of the robot arm 20 positioned by the surgical robot 4. The example end effector 26 includes a tubular guide that guides movement of an inserted surgical tool relative to an anatomical structure on which a surgical procedure is to be performed.

In some embodiments, a dynamic reference array 52 is attached to the end effector 26. Dynamic reference arrays, also referred to as "DRAs" herein, are rigid bodies which may be disposed on an anatomical structure (e.g., bone) of a patient, one or more AR headsets being worn by personnel in the operating room, the end effector, the surgical robot, a surgical tool in a navigated surgical procedure. The computer platform 910 in combination with the camera tracking system 6 or other 3D localization system are configured to track in real-time the pose (e.g., positions and rotational orientations) of the DRA. The DRA can include fiducials, such as the illustrated arrangement of balls. This tracking of 3D coordinates of the DRA can allow the surgical system 2 to determine the pose of the DRA in any multidimensional space in relation to the target anatomical structure of the patient 50 in FIG. 5.

Figure 2:
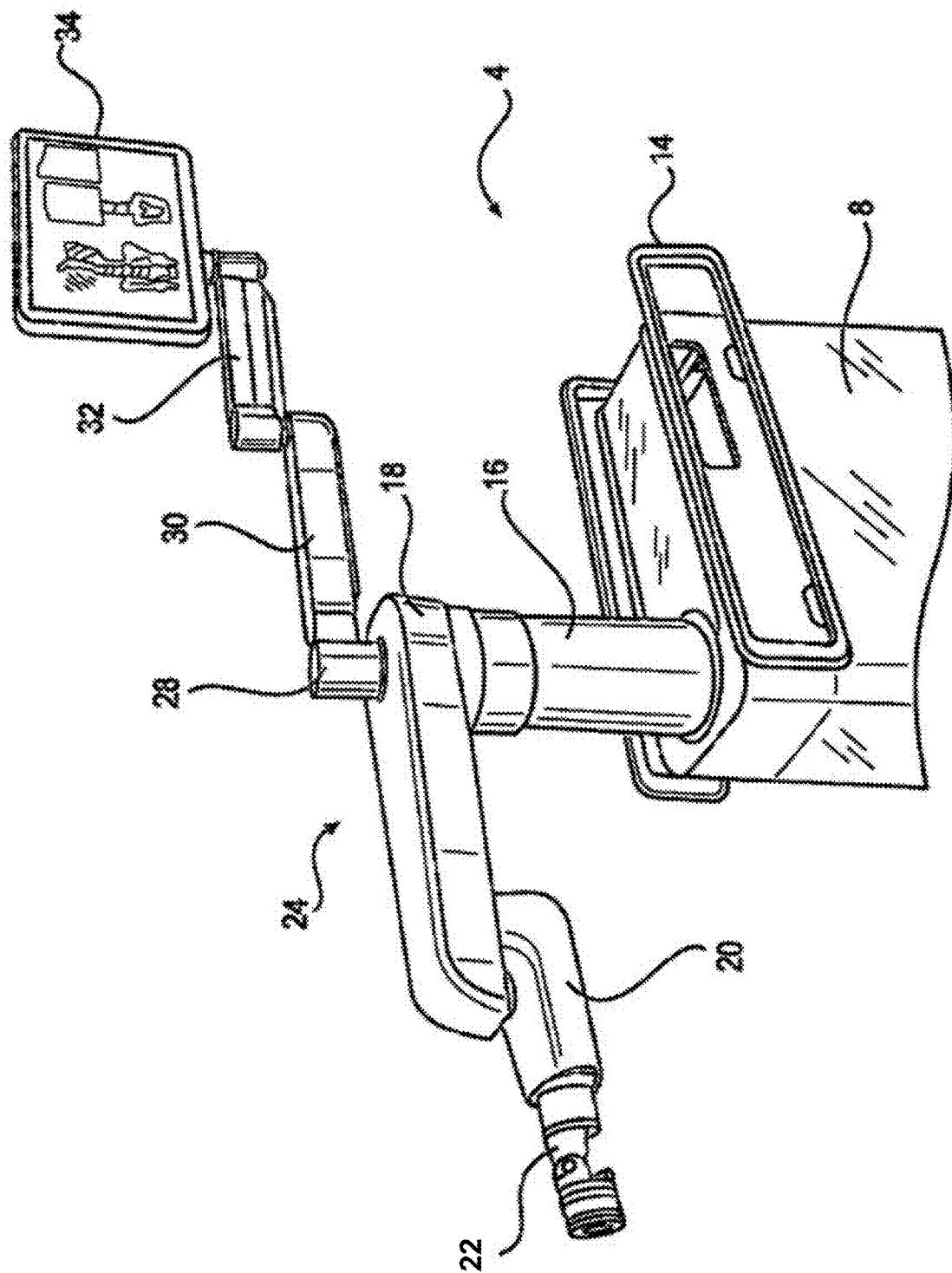
FIG. 2 illustrates a surgical robot component of the surgical system of FIG. 1 according to some embodiments of the present disclosure.

As illustrated in FIG. 1, a light indicator 28 may be positioned on top of the SCARA 24. Light indicator 28 may illuminate as any type of light to indicate "conditions" in which surgical system 2 is currently operating. In some embodiments, the light may be produced by LED bulbs, which may form a ring around light indicator 28. Light indicator 28 may comprise a fully permeable material that can let light shine through the entirety of light indicator 28. Light indicator 28 may be attached to lower display support 30. Lower display support 30, as illustrated in FIG. 2 may allow an operator to maneuver display 34 to any suitable location. Lower display support 30 may attach to light indicator 28 by any suitable mechanism. In some embodiments, lower display support 30 may rotate about light indicator 28 or be rigidly attached thereto. Upper display support 32 may attach to lower display support 30 by any suitable mechanism.

In some embodiments, a tablet may be used in conjunction with display 34 and/or without display 34. The tablet may be disposed on upper display support 32, in place of display 34, and may be removable from upper display support 32 during a medical operation. In addition the tablet may communicate with display 34. The tablet may be able to connect to surgical robot 4 by any suitable wireless and/or wired connection. In some embodiments, the tablet may be able to program and/or control surgical system 2 during a medical operation. When controlling surgical system 2 with the tablet, all input and output commands may be duplicated on display 34. The use of a tablet may allow an operator to manipulate surgical robot 4 without having to move around patient 50 and/or to surgical robot 4.

As will be explained below, in some embodiments a surgeon and/or other personnel can wear AR headsets that may be used in conjunction with display 34 and/or a tablet or the AR head(s) may eliminate the need for use of the display 34 and/or tablet.

Figure 3A:
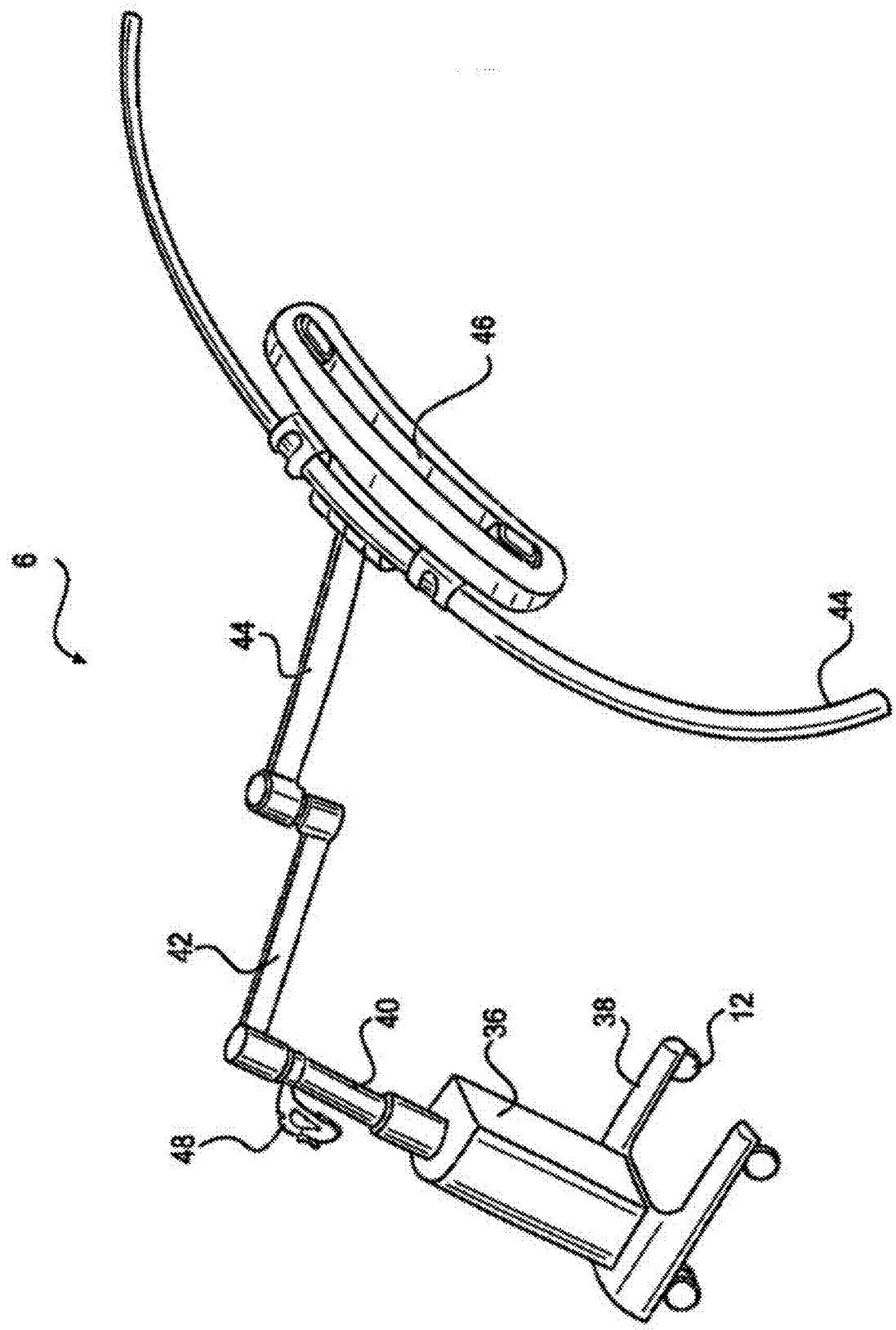
FIG. 3A illustrates a camera tracking system component of the surgical system of FIG. 1 according to some embodiments of the present disclosure.

As illustrated in FIGS. 3A and 5, camera tracking system 6 works in conjunction with surgical robot 4 through wired or wireless communication networks. Referring to FIGS. 1, 3 and 5, camera tracking system 6 can include some similar components to the surgical robot 4. For example, camera body 36 may provide the functionality found in robot body 8. Robot body 8 may provide the structure upon which camera 46 is mounted. The structure within robot body 8 may also provide support for the electronics, communication devices, and power supplies used to operate camera tracking system 6. Camera body 36 may be made of the same material as robot body 8. Camera tracking system 6 may communicate directly to an AR headset, tablet and/or display 34 by a wireless and/or wired network to enable the AR headset, tablet and/or display 34 to control the functions of camera tracking system 6.

Camera body 36 is supported by camera base 38. Camera base 38 may function as robot base 10. In the embodiment of FIG. 1, camera base 38 may be wider than robot base 10. The width of camera base 38 may allow for camera tracking system 6 to connect with surgical robot 4. As illustrated in FIG. 1, the width of camera base 38 may be large enough to fit outside robot base 10. When camera tracking system 6 and surgical robot 4 are connected, the additional width of camera base 38 may allow surgical system 2 additional maneuverability and support for surgical system 2.

As with robot base 10, a plurality of powered wheels 12 may attach to camera base 38. Powered wheel 12 may allow camera tracking system 6 to stabilize and level or set fixed orientation in regards to patient 50, similar to the operation of robot base 10 and powered wheels 12. This stabilization may prevent camera tracking system 6 from moving during a medical procedure and may keep camera 46 from losing track of a DRA connected to an AR headset and/or the surgical robot 4, and/or losing track of one or more DRAs 52 connected to an anatomical structure 54 and/or tool 58 within a designated area 56 as shown in FIGS. 3A and 5. This stability and maintenance of tracking enhances the ability of surgical robot 4 to operate effectively with camera tracking system 6. Additionally, the wide camera base 38 may provide additional support to camera tracking system 6. Specifically, a wide camera base 38 may prevent camera tracking system 6 from tipping over when camera 46 is disposed over a patient, as illustrated in FIGS. 3A and 5.

Camera telescoping support 40 may support camera 46. In some embodiments, telescoping support 40 moves camera 46 higher or lower in the vertical direction. Camera handle 48 may be attached to camera telescoping support 40 at any suitable location and configured to allow an operator to move camera tracking system 6 into a planned position before a medical operation. In some embodiments, camera handle 48 is used to lower and raise camera telescoping support 40. Camera handle 48 may perform the raising and lowering of camera telescoping support 40 through the depression of a button, switch, lever, and/or any combination thereof.

Lower camera support arm 42 may attach to camera telescoping support 40 at any suitable location, in embodiments, as illustrated in FIG. 1, lower camera support arm 42 may rotate three hundred and sixty degrees around telescoping support 40. This free rotation may allow an operator to position camera 46 in any suitable location. Lower camera support arm 42 may connect to telescoping support 40 by any suitable mechanism. Lower camera support arm 42 may be used to provide support for camera 46. Camera 46 may be attached to lower camera support arm 42 by any suitable mechanism. Camera 46 may pivot in any direction at the attachment area between camera 46 and lower camera support arm 42. In embodiments a curved rail 44 may be disposed on lower camera support arm 42.

Curved rail 44 may be disposed at any suitable location on lower camera support arm 42. As illustrated in FIG. 3A, curved rail 44 may attach to lower camera support arm 42 by any suitable mechanism. Curved rail 44 may be of any suitable shape, a suitable shape may be a crescent, circular, oval, elliptical, and/or any combination thereof. Camera 46 may be moveably disposed along curved rail 44. Camera 46 may attach to curved rail 44 by, for example, rollers, brackets, braces, motors, and/or any combination thereof. Motors and rollers, not illustrated, may be used to move camera 46 along curved rail 44. As illustrated in FIG. 3A, during a medical procedure, if an object prevents camera 46 from viewing one or more DRAs being tracked, the motors may responsively move camera 46 along curved rail 44. This motorized movement may allow camera 46 to move to a new position that is no longer obstructed by the object without moving camera tracking system 6. While camera 46 is obstructed from viewing one or more tracked DRAs, camera tracking system 6 may send a stop signal to an surgical robot 4, AR headset, display 34, and/or a tablet. The stop signal may prevent SCARA 24 from moving until camera 46 has reacquired tracked DRAs 52 and/or can warn an operator wearing the AR headset and/or viewing the display 34 and/or the tablet. This SCARA 24 can be configured to respond to receipt of a stop signal by stopping further movement of the base and/or end effector coupler 22 until the camera tracking system can resume tracking of DRAs.

Figure 3C:
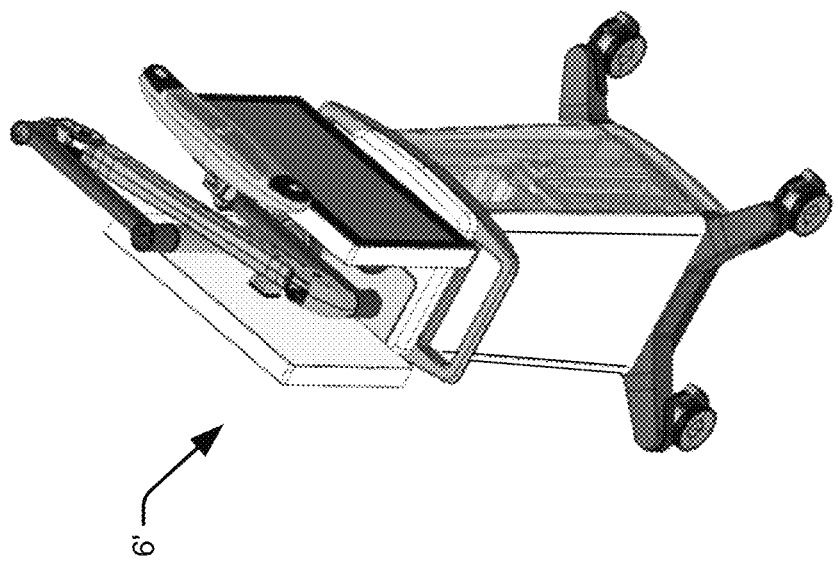
FIGS. 3B and 3C illustrate a front view and isometric view of another camera tracking system component which may be used with the surgical system of FIG. 1 according to some embodiments of the present disclosure.
Figure 3B:
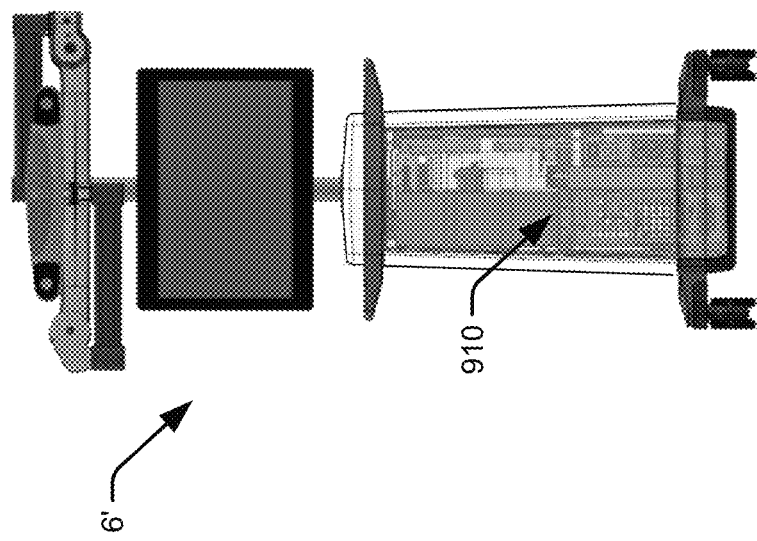

FIGS. 3B and 3C illustrate a front view and isometric view of another camera camera tracking system 6' which may be used with the surgical system of FIG. 1 or may be used independent of a surgical robot. For example, the camera tracking system 6' may be used for providing navigated surgery without use of robotic guidance. One of the differences between the camera tracking system 6' of FIGS. 3B and 3C and the camera tracking system 6 of FIG. 3A, is that the camera tracking system 6' of FIGS. 3B and 3C includes a housing that transports the computer platform 910. The computer platform 910 can be configured to perform camera tracking operations to track DRAs, perform navigated surgery operations that provide surgical navigation information to a display device, e.g., AR headset and/or other display device, and perform other computational operations disclosed herein.

Figure 6:
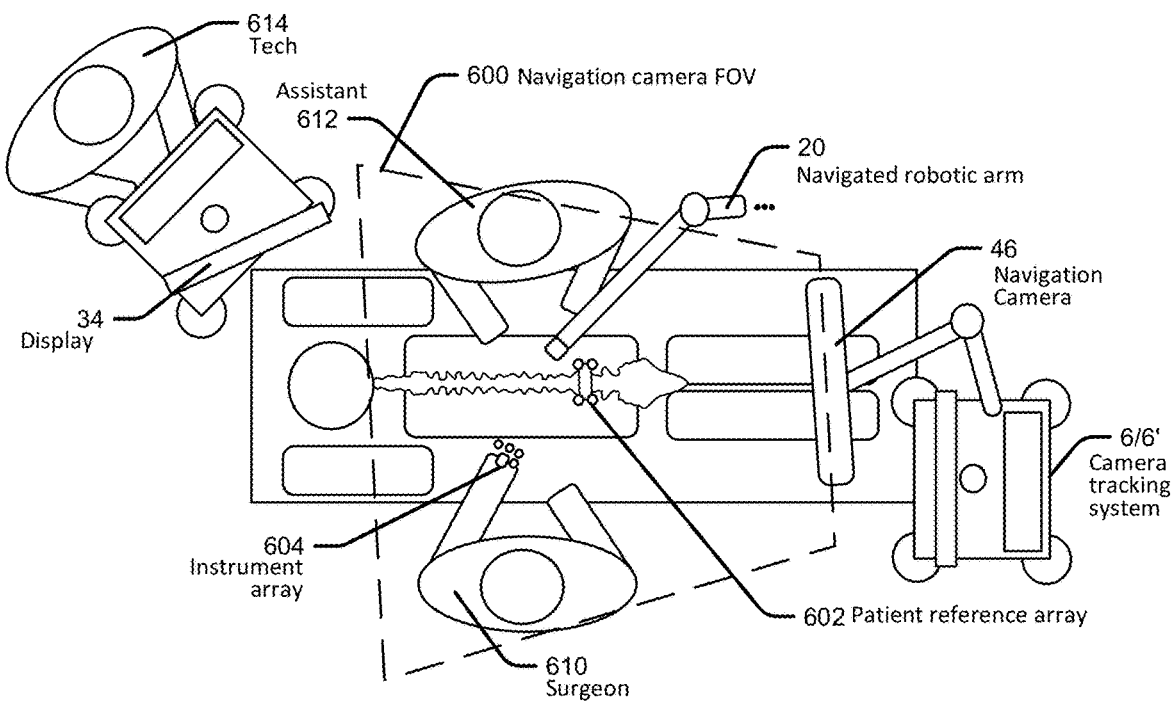
FIG. 6 illustrates a block diagram view of the components of the surgical system of FIG. 5 being used for the medical operation.

FIG. 6 illustrates a block diagram view of the components of the surgical system of FIG. 5 used for the medical operation. Referring to FIG. 6, the navigation camera 46 has a navigation field-of-view 600 in which the pose (e.g., position and orientation) of the reference array 602 attached to the patient, the reference array 604 attached to the surgical instrument, and the robot arm 20 are tracked. The navigation camera 46 may be part of the camera tracking system 6' of FIGS. 3B and 3C, which includes the computer platform 910 configured to perform the operations described below. The reference arrays enable tracking by reflecting light in known patterns, which are decoded to determine their respective poses by the tracking subsystem of the surgical robot 4. If the line-of-sight between the patient reference array 602 and the navigation camera 46 is blocked (for example, by a medical personnel, instrument, etc.), further navigation of the surgical instrument may not be able to be performed and a responsive notification may temporarily halt further movement of the robot arm 20 and surgical robot 4, display a warning on the display 34, and/or provide an audible warning to medical personnel. The display 34 is accessible to the surgeon 610 and assistant 612 but viewing requires a head to be turned away from the patient and for eye focus to be changed to a different distance and location. The navigation software may be controlled by a tech personnel 614 based on vocal instructions from the surgeon.

Figure 7:
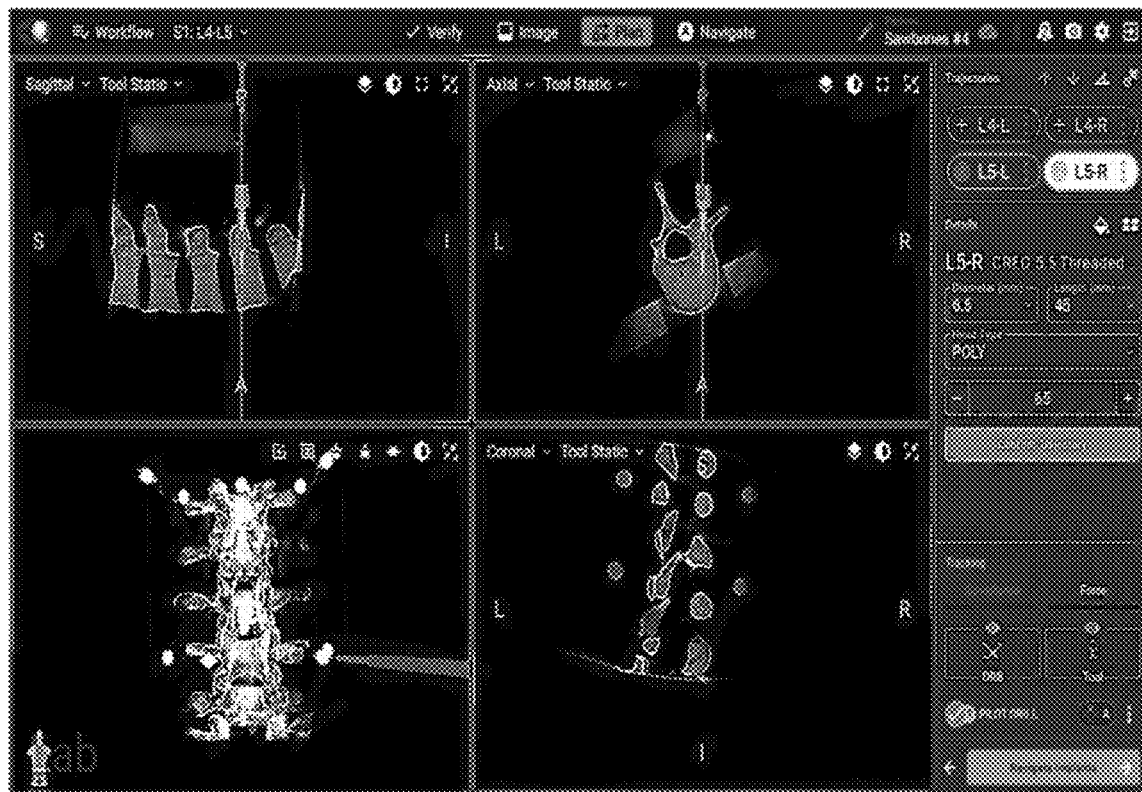
FIG. 7 illustrates various display screens that may be displayed on the display of FIGS. 5 and 6 when using a navigation function of the surgical system.

FIG. 7 illustrates various display screens that may be displayed on the display 34 of FIGS. 5 and 6 by the surgical robot 4 when using a navigation function of the surgical system 2. The display screens can include, without limitation, patient radiographs with overlaid graphical representations of models of instruments that are positioned in the display screens relative to the anatomical structure based on a developed surgical plan and/or based on poses of tracked reference arrays, various user selectable menus for controlling different stages of the surgical procedure and dimension parameters of a virtually projected implant (e.g. length, width, and/or diameter).

For navigated surgery, various processing components (e.g., computer platform 910) and associated software described below are provided that enable pre-operatively planning of a surgical procedure, e.g., implant placement, and electronic transfer of the plan to computer platform 910 to provide navigation information to one or more users during the planned surgical procedure.

For robotic navigation, various processing components (e.g., computer platform 910) and associated software described below are provided that enable pre-operatively planning of a surgical procedure, e.g., implant placement, and electronic transfer of the plan to the surgical robot 4. The surgical robot 4 uses the plan to guide the robot arm 20 and connected end effector 26 to provide a target pose for a surgical tool relative to a patient anatomical structure for a step of the planned surgical procedure.

Various embodiments below are directed to using one or more AR headsets that can be worn by the surgeon 610, the assistant 612, and/or other medical personnel to provide an improved user interface for receiving information from and/or providing control commands to the surgical robot, the camera tracking system 6/6', and/or other medical equipment in the operating room.

Figure 8:
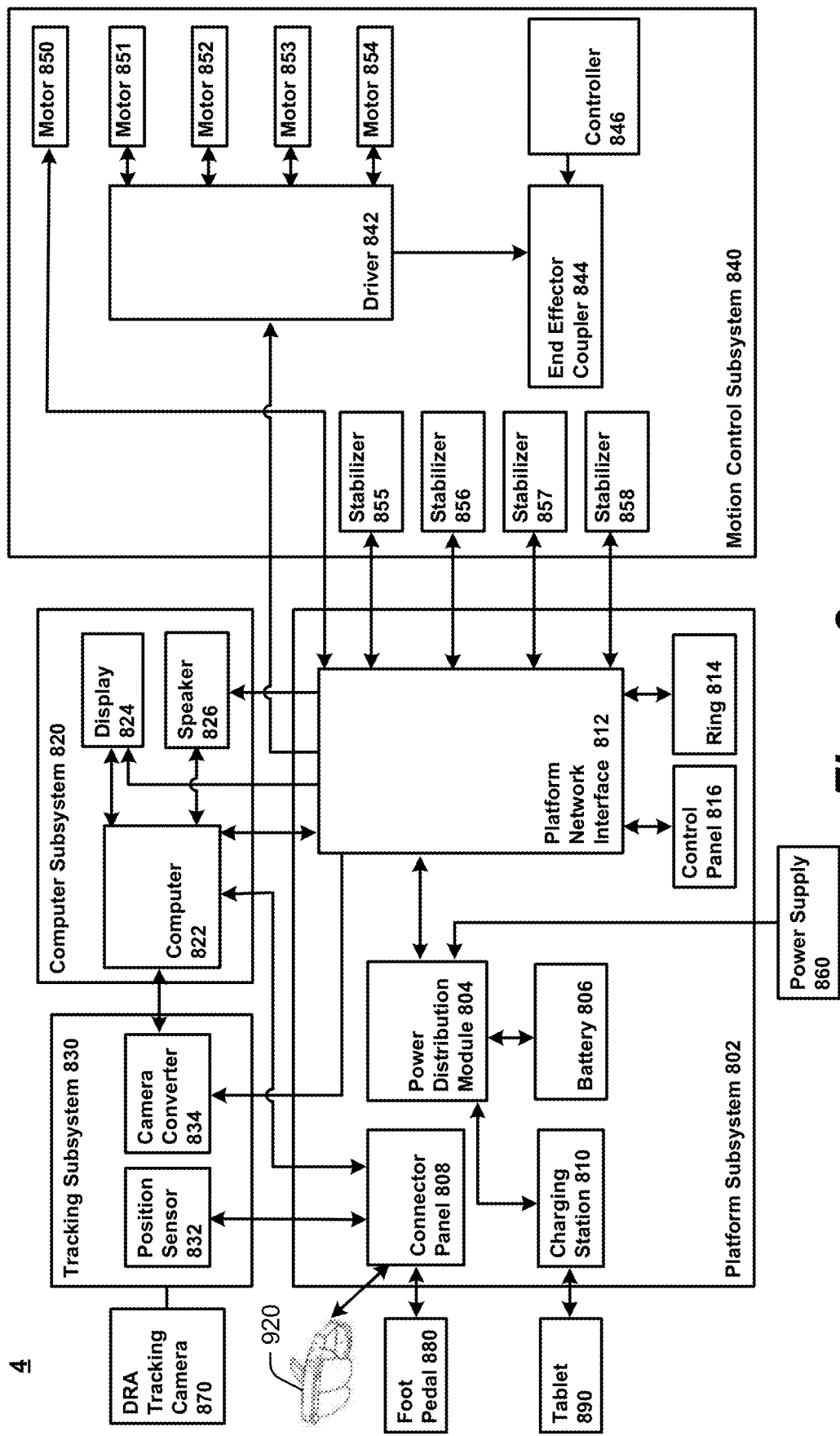
FIG. 8 illustrates a block diagram of some electrical components of a surgical robot according to some embodiments of the present disclosure.

FIG. 8 illustrates a block diagram of some electrical components of the surgical robot 4 according to some embodiments of the present disclosure. Referring to FIG. 8, a load cell (not shown) may be configured to track force applied to end effector coupler 22. In some embodiments the load cell may communicate with a plurality of motors 850, 851, 852, 853, and/or 854. As load cell senses force, information as to the amount of force applied may be distributed from a switch array and/or a plurality of switch arrays to a controller 846. Controller 846 may take the force information from load cell and process it with a switch algorithm. The switch algorithm is used by the controller 846 to control a motor driver 842. The motor driver 842 controls operation of one or more of the motors 850, 851, 852, 853, and 854. Motor driver 842 may direct a specific motor to produce, for example, an equal amount of force measured by load cell through the motor. In some embodiments, the force produced may come from a plurality of motors, e.g., 850-854, as directed by controller 846. Additionally, motor driver 842 may receive input from controller 846. Controller 846 may receive information from load cell as to the direction of force sensed by load cell. Controller 846 may process this information using a motion controller algorithm. The algorithm may be used to provide information to specific motor drivers 842. To replicate the direction of force, controller 846 may activate and/or deactivate certain motor drivers 842. Controller 846 may control one or more motors, e.g. one or more of 850-854, to induce motion of end effector 26 in the direction of force sensed by load cell. This force-controlled motion may allow an operator to move SCARA 24 and end effector 26 effortlessly and/or with very little resistance. Movement of end effector 26 can be performed to position end effector 26 in any suitable pose (i.e., location and angular orientation relative to defined three-dimensional (3D) orthogonal reference axes) for use by medical personnel.

Activation assembly 60, best illustrated in FIG. 5, may form of a bracelet that wraps around end effector coupler 22. The activation assembly 60 may be located on any part of SCARA 24, any part of end effector coupler 22, may be worn by medical personnel (and communicate wirelessly), and/or any combination thereof. Activation assembly 60 may comprise of a primary button and a secondary button.

Depressing primary button may allow an operator to move SCARA 24 and end effector coupler 22. According to one embodiment, once set in place, SCARA 24 and end effector coupler 22 may not move until an operator programs surgical robot 4 to move SCARA 24 and end effector coupler 22, or is moved using primary button. In some examples, it may require the depression of at least two non-adjacent primary activation switches before SCARA 24 and end effector coupler 22 will respond to operator commands. Depression of at least two primary activation switches may prevent the accidental movement of SCARA 24 and end effector coupler 22 during a medical procedure.

Activated by primary button, load cell may measure the force magnitude and/or direction exerted upon end effector coupler 22 by an operator, i.e. medical personnel. This information may be transferred to one or more motors, e.g. one or more of 850-854, within SCARA 24 that may be used to move SCARA 24 and end effector coupler 22. Information as to the magnitude and direction of force measured by load cell may cause the one or more motors, e.g. one or more of 850-854, to move SCARA 24 and end effector coupler 22 in the same direction as sensed by the load cell. This force-controlled movement may allow the operator to move SCARA 24 and end effector coupler 22 easily and without large amounts of exertion due to the motors moving SCARA 24 and end effector coupler 22 at the same time the operator is moving SCARA 24 and end effector coupler 22.

In some examples, a secondary button may be used by an operator as a "selection" device. During a medical operation, surgical robot 4 may notify medical personnel to certain conditions by the AR headset(s) 920, display 34 and/or light indicator 28. The AR headset(s) 920 are each configured to display images on a see-through display screen to form an augmented reality image that is overlaid on real-world objects viewable through the see-through display screen. Medical personnel may be prompted by surgical robot 4 to select a function, mode, and/or assess the condition of surgical system 2. Depressing secondary button a single time may activate certain functions, modes, and/or acknowledge information communicated to medical personnel through the AR headset(s) 920, display 34 and/or light indicator 28. Additionally, depressing the secondary button multiple times in rapid succession may activate additional functions, modes, and/or select information communicated to medical personnel through the AR headset(s) 920, display 34 and/or light indicator 28.

With further reference to FIG. 8, electrical components of the surgical robot 4 include platform subsystem 802, computer subsystem 820, motion control subsystem 840, and tracking subsystem 830. Platform subsystem 802 includes battery 806, power distribution module 804, connector panel 808, and charging station 810. Computer subsystem 820 includes computer 822, display 824, and speaker 826. Motion control subsystem 840 includes driver circuit 842, motors 850, 851, 852, 853, 854, stabilizers 855, 856, 857, 858, end effector connector 844, and controller 846. Tracking subsystem 830 includes position sensor 832 and camera converter 834. Surgical robot 4 may also include a removable foot pedal 880 and removable tablet computer 890.

Input power is supplied to surgical robot 4 via a power source which may be provided to power distribution module 804. Power distribution module 804 receives input power and is configured to generate different power supply voltages that are provided to other modules, components, and subsystems of surgical robot 4. Power distribution module 804 may be configured to provide different voltage supplies to connector panel 808, which may be provided to other components such as computer 822, display 824, speaker 826, driver 842 to, for example, power motors 850-854 and end effector coupler 844, and provided to camera converter 834 and other components for surgical robot 4. Power distribution module 804 may also be connected to battery 806, which serves as temporary power source in the event that power distribution module 804 does not receive power from an input power. At other times, power distribution module 804 may serve to charge battery 806.

Connector panel 808 may serve to connect different devices and components to surgical robot 4 and/or associated components and modules. Connector panel 808 may contain one or more ports that receive lines or connections from different components. For example, connector panel 808 may have a ground terminal port that may ground surgical robot 4 to other equipment, a port to connect foot pedal 880, a port to connect to tracking subsystem 830, which may include position sensor 832, camera converter 834, and DRA tracking cameras 870. Connector panel 808 may also include other ports to allow USB, Ethernet, HDMI communications to other components, such as computer 822. In accordance with some embodiments, the connector panel 808 can include a wired and/or wireless interface for operatively connecting one or more AR headsets 920 to the tracking subsystem 830 and/or the computer subsystem 820.

Control panel 816 may provide various buttons or indicators that control operation of surgical robot 4 and/or provide information from surgical robot 4 for observation by an operator. For example, control panel 816 may include buttons to power on or off surgical robot 4, lift or lower vertical column 16, and lift or lower stabilizers 855-858 that may be designed to engage casters 12 to lock surgical robot 4 from physically moving. Other buttons may stop surgical robot 4 in the event of an emergency, which may remove all motor power and apply mechanical brakes to stop all motion from occurring. Control panel 816 may also have indicators notifying the operator of certain system conditions such as a line power indicator or status of charge for battery 806. In accordance with some embodiments, one or more AR headsets 920 may communicate, e.g. via the connector panel 808, to control operation of the surgical robot 4 and/or to received and display information generated by surgical robot 4 for observation by persons wearing the AR headsets 920.

Computer 822 of computer subsystem 820 includes an operating system and software to operate assigned functions of surgical robot 4. Computer 822 may receive and process information from other components (for example, tracking subsystem 830, platform subsystem 802, and/or motion control subsystem 840) in order to display information to the operator. Further, computer subsystem 820 may provide output through the speaker 826 for the operator. The speaker may be part of the surgical robot, part of an AR headset 920, or within another component of the surgical system 2. The display 824 may correspond to the display 34 shown in FIGS. 1 and 2.

Tracking subsystem 830 may include position sensor 832 and camera converter 834. Tracking subsystem 830 may correspond to the camera tracking system 6 of FIG. 3. The DRA tracking cameras 870 operate with the position sensor 832 to determine the pose of DRAs 52. This tracking may be conducted in a manner consistent with the present disclosure including the use of infrared or visible light technology that tracks the location of active or passive elements of DRAs 52, such as LEDs or reflective markers, respectively.

Functional operations of the tracking subsystem 830 and the computer subsystem 820 can be included in the computer platform 910, which can be transported by the camera tracking system 6' of FIGS. 3A and 3B. The tracking subsystem 830 can be configured to determine the poses, e.g., location and angular orientation of the tracked DRAs. The computer platform 910 can also include a navigation controller that is configured to use the determined poses to provide navigation information to users that guides their movement of tracked tools relative to position-registered patient images and/or tracked anatomical structures during a planned surgical procedure. The computer platform 910 can display information on the display of FIGS. 3B and 3C and/or to one or more AR headsets 920. The computer platform 910, when used with a surgical robot, can be configured to communicate with the computer subsystem 820 and other subsystems of FIG. 8 to control movement of the end effector 26. For example, as will be explained below the computer platform 910 can generate a graphical representation of a patient's anatomical structure, surgical tool, user's hand, etc. with a displayed size, shape, color, and/or pose that is controlled based on the determined pose(s) of one or more the tracked DRAs, and which the graphical representation that is displayed can be dynamically modified to track changes in the determined poses over time.

Motion control subsystem 840 may be configured to physically move vertical column 16, upper arm 18, lower arm 20, or rotate end effector coupler 22. The physical movement may be conducted through the use of one or more motors 850-854. For example, motor 850 may be configured to vertically lift or lower vertical column 16. Motor 851 may be configured to laterally move upper arm 18 around a point of engagement with vertical column 16 as shown in FIG. 2. Motor 852 may be configured to laterally move lower arm 20 around a point of engagement with upper arm 18 as shown in FIG. 2. Motors 853 and 854 may be configured to move end effector coupler 22 to provide translational movement and rotation along in about three-dimensional axes. The computer platform 910 shown in FIG. 9 can provide control input to the controller 846 that guides movement of the end effector coupler 22 to position a passive end effector, which is connected thereto, with a planned pose (i.e., location and angular orientation relative to defined 3D orthogonal reference axes) relative to an anatomical structure that is to be operated on during a planned surgical procedure. Motion control subsystem 840 may be configured to measure position of the end effector coupler 22 and/or the end effector 26 using integrated position sensors (e.g. encoders).

Figure 9:
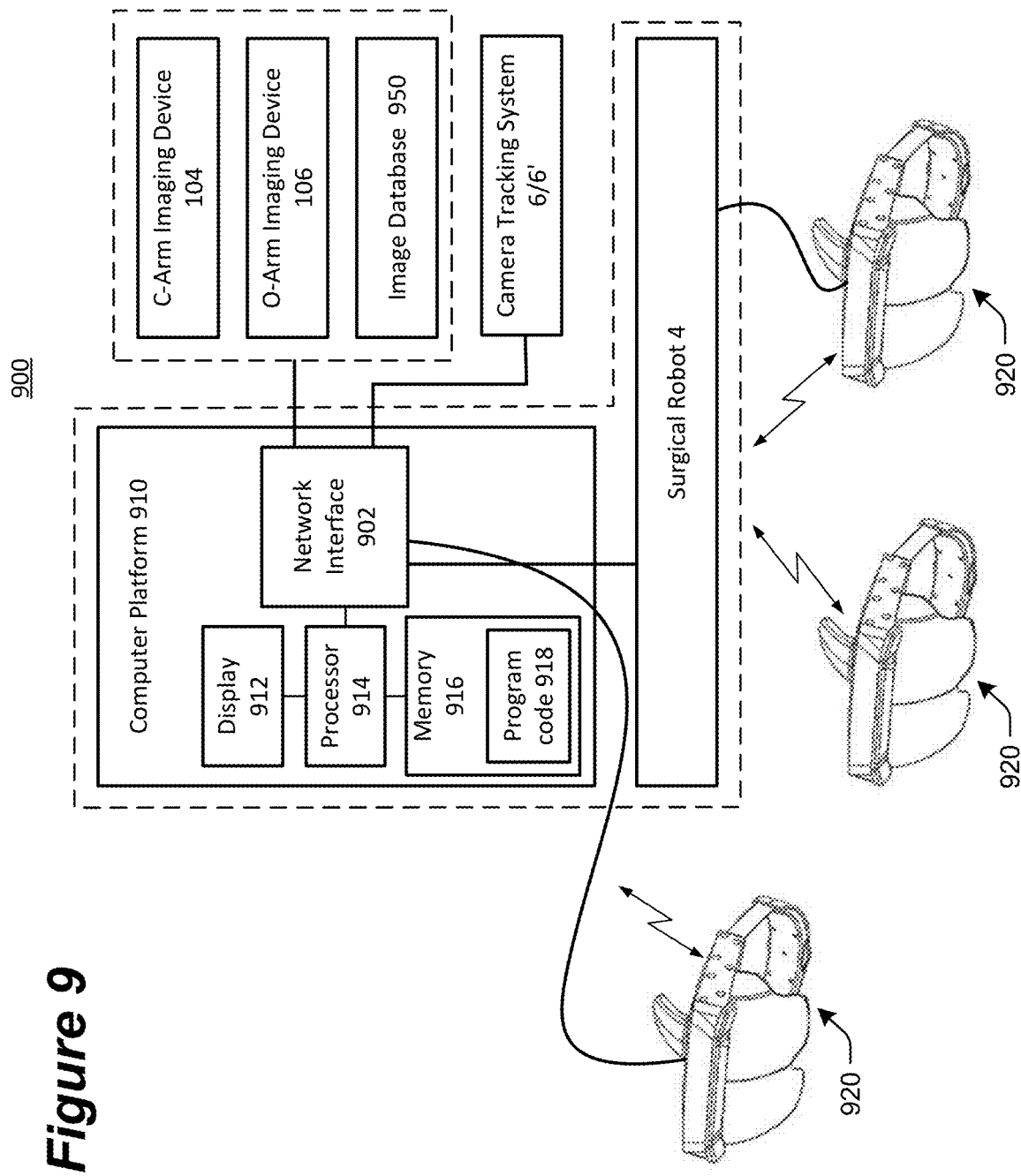
FIG. 9 illustrates a block diagram of components of a surgical system that includes imaging devices connected to a computer platform which can be operationally connected to a camera tracking system and/or surgical robot according to some embodiments of the present disclosure.

FIG. 9 illustrates a block diagram of components of a surgical system that includes imaging devices (e.g., C-Arm 104, O-Arm 106, etc.) connected to a computer platform 910 which can be operationally connected to a camera tracking system 6 (FIG. 3A) or 6' (FIGS. 3B, 3C) and/or to surgical robot 4 according to some embodiments of the present disclosure. Alternatively, at least some operations disclosed herein as being performed by the computer platform 910 may additionally or alternatively be performed by components of a surgical system.

Referring to FIG. 9, the computer platform 910 includes a display 912, at least one processor circuit 914 (also referred to as a processor for brevity), at least one memory circuit 916 (also referred to as a memory for brevity) containing computer readable program code 918, and at least one network interface 902 (also referred to as a network interface for brevity). The display 912 may be part of an AR headset 920 in accordance with some embodiments of the present disclosure. The network interface 902 can be configured to connect to a C-Arm imaging device 104 in FIG. 10, an O-Arm imaging device 106 in FIG. 11, another medical imaging device, an image database 950 containing patient medical images, components of the surgical robot 4, and/or other electronic equipment.

When used with a surgical robot 4, the display 912 may correspond to the display 34 of FIG. 2 and/or the tablet 890 of FIG. 8 and/or the AR headset 920 that is operatively connected to the surgical robot 4, the network interface 902 may correspond to the platform network interface 812 of FIG. 8, and the processor 914 may correspond to the computer 822 of FIG. 8. The network interface 902 of the AR headset 920 may be configured to communicate through a wired network, e.g., thin wire ethernet, and/or through wireless RF transceiver link according to one or more wireless communication protocols, e.g., WLAN, 3GPP 4G and/or 5G (New Radio) cellular communication standards, etc.

The processor 914 may include one or more data processing circuits, such as a general purpose and/or special purpose processor, e.g., microprocessor and/or digital signal processor. The processor 914 is configured to execute the computer readable program code 918 in the memory 916 to perform operations, which may include some or all of the operations described herein as being performed for surgery planning, navigated surgery, and/or robotic surgery.

The computer platform 910 can be configured to provide surgery planning functionality. The processor 914 can operate to display on the display device 912 and/or on the AR headset 920 an image of an anatomical structure, e.g., vertebra, that is received from one of the imaging devices 104 and 106 and/or from the image database 950 through the network interface 920. The processor 914 receives an operator's definition of where the anatomical structure shown in one or more images is to have a surgical procedure, e.g., screw placement, such as by the operator touch selecting locations on the display 912 for planned procedures or using a mouse-based cursor to define locations for planned procedures. When the image is displayed in the AR headset 920, the AR headset can be configured to sense in gesture-based commands formed by the wearer and/or sense voice based commands spoken by the wearer, which can be used to control selection among menu items and/or control how objects are displayed on the AR headset 920 as will be explained in further detail below.

The computer platform 910 can be configured to enable anatomy measurement, which can be particularly useful for knee surgery, like measurement of various angles determining center of hip, center of angles, natural landmarks (e.g. transepicondylar line, Whitesides line, posterior condylar line), etc. Some measurements can be automatic while some others can involve human input or assistance. The computer platform 910 may be configured to allow an operator to input a choice of the correct implant for a patient, including choice of size and alignment. The computer platform 910 may be configured to perform automatic or semi-automatic (involving human input) segmentation (image processing) for CT images or other medical images. The surgical plan for a patient may be stored in a cloud-based server, which may correspond to database 950, for retrieval by the surgical robot 4.

During orthopedic surgery, for example, a surgeon may choose which cut to make (e.g. posterior femur, proximal tibia etc.) using a computer screen (e.g. touchscreen) or augmented reality interaction (e.g., hand gesture based commands and/or voice based commands) via, e.g., the AR headset 920. The computer platform 910 can generate navigation information which provides visual guidance to the surgeon for performing the surgical procedure. When used with the surgical robot 4, the computer platform 910 can provide guidance that allows the surgical robot 4 to automatically move the end effector 26 to a target pose so that the surgical tool is aligned with a target location to perform the surgical procedure on an anatomical structure.

In some embodiments, the surgical system 900 can use two DRAs to track patient anatomy position, such as one connected to patient tibia and one connected to patient femur. The system 900 may use standard navigated instruments for the registration and checks (e.g. a pointer similar to the one used in Globus ExcelsiusGPS system for spine surgery).

A particularly challenging task in navigated surgery is how to plan the position of an implant in spine, knee, and other anatomical structures where surgeons struggle to perform the task on a computer screen which is a 2D representation of the 3D anatomical structure. The system 900 could address this problem by using the AR headset 920 to display a three-dimensional (3D) computer generated representations of the anatomical structure and a candidate implant device. The computer generated representations are scaled and posed relative to each other on the display screen under guidance of the computer platform 910 and which can be manipulated by a surgeon while viewed through the AR headset 920. A surgeon may, for example, manipulate the displayed computer-generated representations of the anatomical structure, the implant, a surgical tool, etc., using hand gesture based commands and/or voice based commands that are sensed by the AR headset 920.

For example, a surgeon can view a displayed virtual handle on a virtual implant, and can manipulate (e.g., grab and move) the virtual handle to move the virtual implant to a desired pose and adjust a planned implant placement relative to a graphical representation of an anatomical structure. Afterward, during surgery, the computer platform 910 could display navigation information through the AR headset 920 that facilitates the surgeon's ability to more accurately follow the surgical plan to insert the implant and/or to perform another surgical procedure on the anatomical structure. When the surgical procedure involves bone removal, the progress of bone removal, e.g., depth of cut, can be displayed in real-time through the AR headset 920. Other features that may be displayed through the AR headset 920 can include, without limitation, gap or ligament balance along a range of joint motion, contact line on the implant along the range of joint motion, ligament tension and/or laxity through color or other graphical renderings, etc.

The computer platform 910, in some embodiments, can allow planning for use of standard surgical tools and/or implants, e.g., posterior stabilized implants and cruciate retaining implants, cemented and cementless implants, revision systems for surgeries related to, for example, total or partial knee and/or hip replacement and/or trauma.

Figure 10:
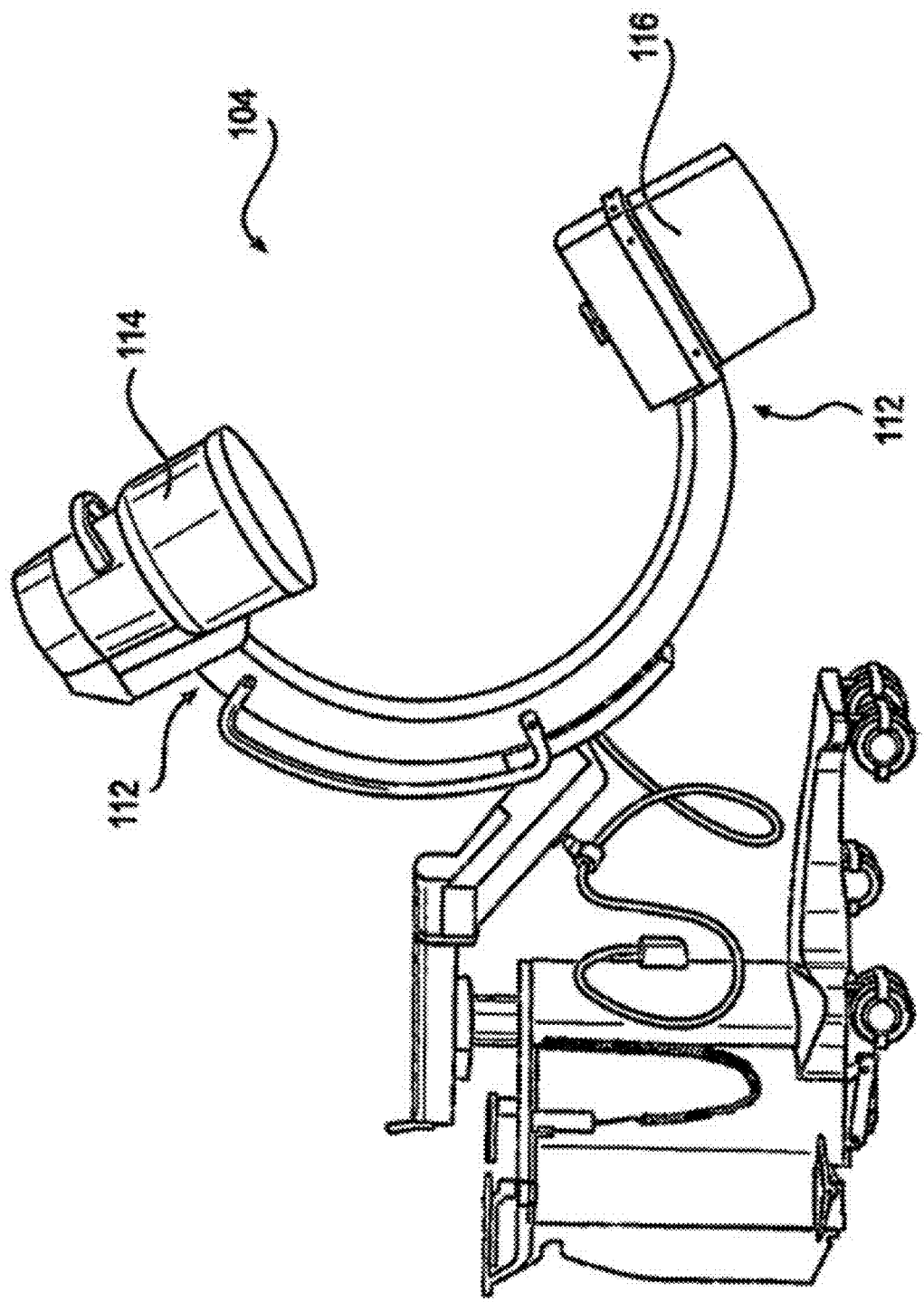
FIG. 10 illustrates an embodiment of a C-Arm imaging device that can be used in combination with the surgical robot in accordance with some embodiments of the present disclosure.
Figure 11:
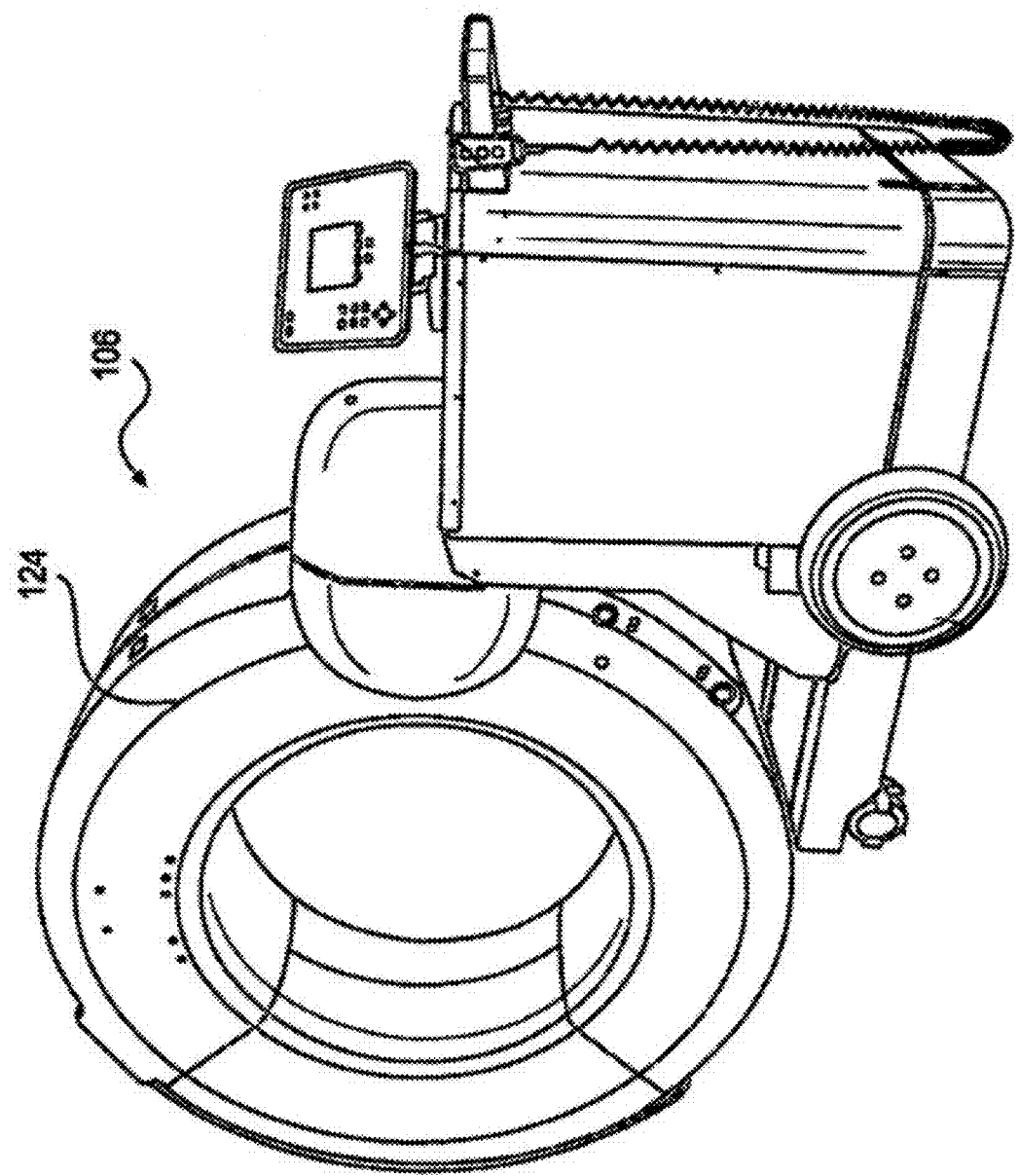
FIG. 11 illustrates an embodiment of an O-Arm imaging device that can be used in combination with the surgical robot in accordance with some embodiments of the present disclosure.

An automated imaging system can be used in conjunction with the computer platform 910 to acquire pre-operative, intra-operative, post-operative, and/or real-time image data of an anatomical structure. Example automated imaging systems are illustrated in FIGS. 10 and 11. In some embodiments, the automated imaging system is a C-arm 104 (FIG. 10) imaging device or an O-arm® 106 (FIG. 11). (O-arm® is copyrighted by Medtronic Navigation, Inc. having a place of business in Louisville, Colo., USA) It may be desirable to take x-rays of a patient from a number of different positions, without the need for frequent manual repositioning of the patient which may be required in an x-ray system. C-arm 104 x-ray diagnostic equipment may solve the problems of frequent manual repositioning and may be well known in the medical art of surgical and other interventional procedures. As illustrated in FIG. 10, a C-arm includes an elongated C-shaped member terminating in opposing distal ends 112 of the "C" shape. C-shaped member is attached to an x-ray source 114 and an image receptor 116. The space within C-arm 104 of the arm provides room for the physician to attend to the patient substantially free of interference from the x-ray support structure.

The C-arm is mounted to enable rotational movement of the arm in two degrees of freedom, (i.e. about two perpendicular axes in a spherical motion). C-arm is slidably mounted to an x-ray support structure, which allows orbiting rotational movement of the C-arm about its center of curvature, which may permit selective orientation of x-ray source 114 and image receptor 116 vertically and/or horizontally. The C-arm may also be laterally rotatable, (i.e. in a perpendicular direction relative to the orbiting direction to enable selectively adjustable positioning of x-ray source 114 and image receptor 116 relative to both the width and length of the patient). Spherically rotational aspects of the C-arm apparatus allow physicians to take x-rays of the patient at an optimal angle as determined with respect to the particular anatomical condition being imaged.

The O-arm® 106 illustrated in FIG. 11 includes a gantry housing 124 which may enclose an image capturing portion, not illustrated. The image capturing portion includes an x-ray source and/or emission portion and an x-ray receiving and/or image receiving portion, which may be disposed about one hundred and eighty degrees from each other and mounted on a rotor (not illustrated) relative to a track of the image capturing portion. The image capturing portion may be operable to rotate three hundred and sixty degrees during image acquisition. The image capturing portion may rotate around a central point and/or axis, allowing image data of the patient to be acquired from multiple directions or in multiple planes.

The O-arm® 106 with the gantry housing 124 has a central opening for positioning around an object to be imaged, a source of radiation that is rotatable around the interior of gantry housing 124, which may be adapted to project radiation from a plurality of different projection angles. A detector system is adapted to detect the radiation at each projection angle to acquire object images from multiple projection planes in a quasi-simultaneous manner. The gantry may be attached to a support structure O-arm® support structure, such as a wheeled mobile cart with wheels, in a cantilevered fashion. A positioning unit translates and/or tilts the gantry to a planned position and orientation, preferably under control of a computerized motion control system. The gantry may include a source and detector disposed opposite one another on the gantry. The source and detector may be secured to a motorized rotor, which may rotate the source and detector around the interior of the gantry in coordination with one another. The source may be pulsed at multiple positions and orientations over a partial and/or full three hundred and sixty degree rotation for multi-planar imaging of a targeted object located inside the gantry. The gantry may further comprise a rail and bearing system for guiding the rotor as it rotates, which may carry the source and detector. Both and/or either O-arm® 106 and C-arm 104 may be used as automated imaging system to scan a patient and send information to the surgical system 2.

Images captured by an imaging system can be displayed on the AR headset 920 and/or another display device of the computer platform 910, the surgical robot 4, and/or another component of the surgical system 900. The AR headset 920 may be connected to one or more of the imaging devices 104 and/or 106 and/or to the image database 950, e.g., via the computer platform 910, to display images therefrom. A user may provide control inputs through the AR headset 920, e.g., gesture and/or voice based commands, to control operation of one or more of the imaging devices 104 and/or 106 and/or the image database 950.

Figure 12:
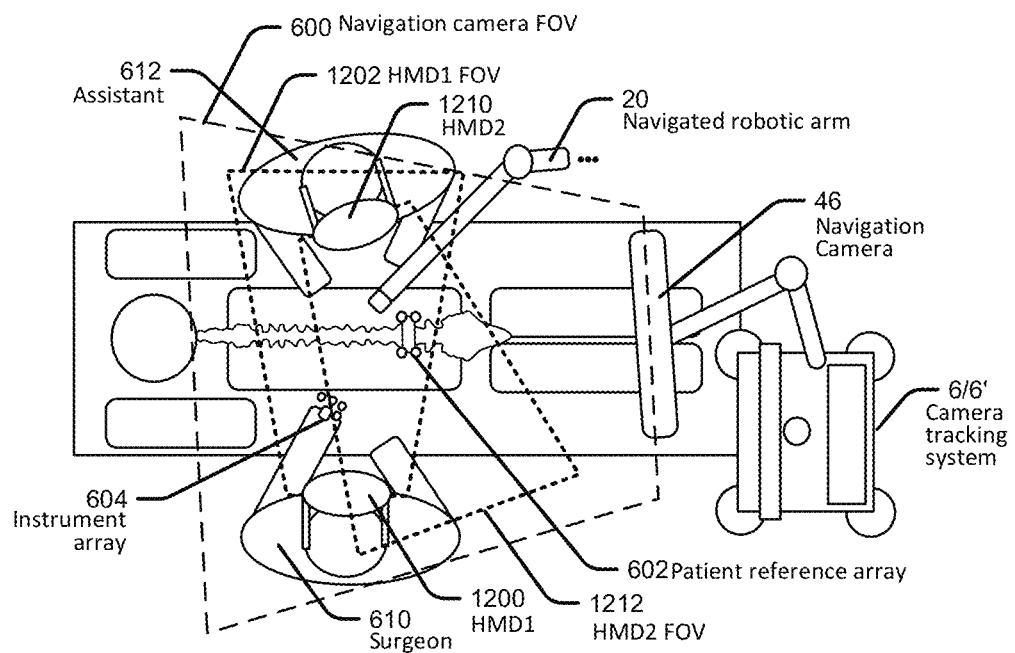
FIG. 12 illustrates a block diagram view of the components of a surgical system that includes a pair of AR headsets operating in accordance with some embodiments of the present disclosure.
Figure 13:
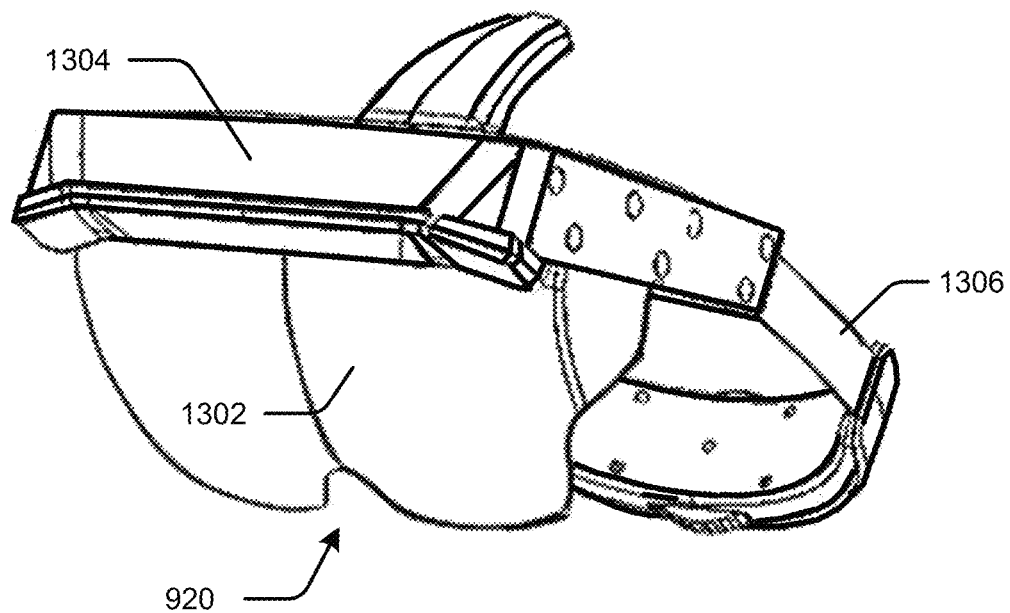
FIG. 13 illustrates an AR headset which is configured in accordance with some embodiments of the present disclosure.

FIG. 12 illustrates a block diagram view of the components of a surgical system that include a pair of AR headsets 1200 and 1210 (head-mounted displays HMD1 and HMD2), which may correspond to the AR headset 920 shown in FIG. 13 and operate in accordance with some embodiments of the present disclosure.

Referring to the example scenario of FIG. 12, the assistant 612 and surgeon 610 are both wearing the AR headsets 1210 and 1210, respectively. It is optional for the assistant 612 to wear the AR headset 1210. The AR headsets 1200 and 1210 are configured to provide an interactive environment through which the wearers can view and interact with information related to a surgical procedure as will be described further below. This interactive AR based environment may eliminate a need for the tech 614 to be present in the operating room and may eliminate a need for use of the display 34 shown in FIG. 6. Each AR headset 1200 and 1210 can include one or more cameras that are be configured to provide an additional source of tracking of DRAs or other reference arrays attached to instruments, an anatomical structure, the end effector 26, and/or other equipment. In the example of FIG. 12, AR headset 1200 has a field-of-view (FOV) 1202 for tracking DRAs and other objects, AR headset 1210 has a FOV 1212 partially overlapping FOV 1202 for tracking DRAs and other objects, and the navigation camera 46 has another FOV 600 partially overlapping FOVs 1202 and 1212 for tracking DRAs and other objects.

If one or more cameras is obstructed from viewing a DRA attached to a tracked object, e.g., a surgical instrument, but the DRA is in view of one or more other cameras the tracking subsystem 830 and/or navigation controller 828 can continue to track the object seamlessly without loss of navigation. Additionally, if there is partial occlusion of the DRA from the perspective of one camera, but the entire DRA is visible via multiple camera sources, the tracking inputs of the cameras can be merged to continue navigation of the DRA. One of the AR headsets and/or the navigation camera 46 may view and track the DRA on another one of the AR headsets to enable the computer platform 910 (FIGS. 9 and 14), the tracking subsystem 830, and/or another computing component to determine the pose of the AR headset.

The AR headsets 1200 and 1210 can be operatively connected to view video, pictures, and/or other information received from and/or to provide commands that control various equipment in the surgical room, including but not limited to neuromonitoring, microscopes, video cameras, and anesthesia systems. Data from the various equipment may be processed and displayed within the headset, for example the display of patient vitals or the microscope feed.

Example AR Headset Components and Integration to Surgical Robot and Other Equipment FIG. 13 illustrates an AR headset 920 which is configured in accordance with some embodiments of the present disclosure. The AR headset includes a headband 1306 configured to secure the AR headset to a wearer's head, and includes a display screen 1302 and an electronic component enclosure 1304 supported by the headband 1306. The display screen 1302 may be a see-through LCD display device or a semi-reflective lens that reflects images projected by a display device toward the wearer's eyes.

Figure 14:
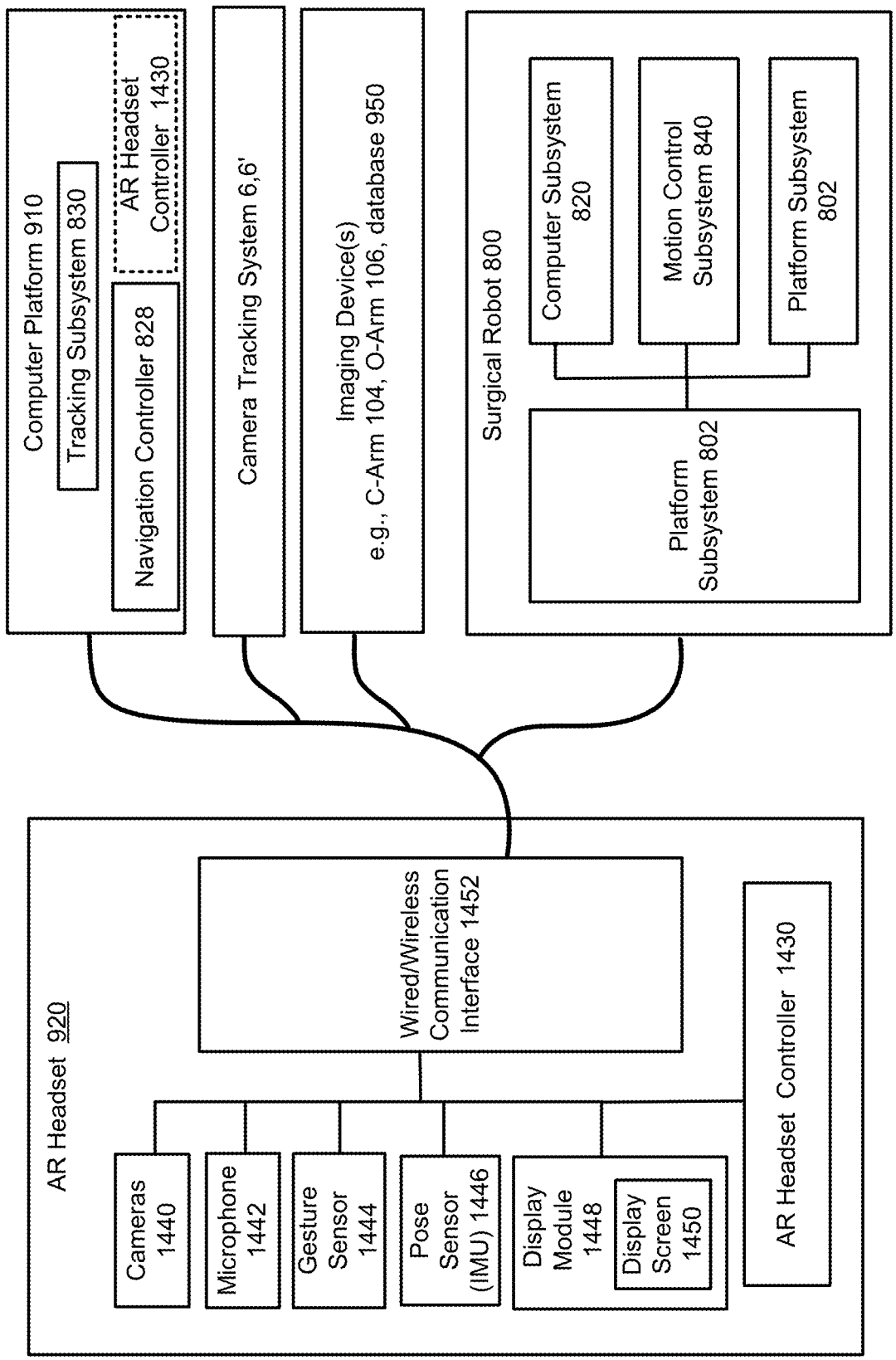
FIG. 14 illustrates electrical components of the AR headset that can be operatively connected to a computer platform, imaging device(s), and/or a surgical robot in accordance with some embodiments of the present disclosure.

FIG. 14 illustrates electrical components of the AR headset 920 that can be operatively connected to the computer platform 910, to one or more of the imaging devices, such as the C-arm imaging device 104, the O-arm imaging device 106, and/or the image database 950, and/or to the surgical robot 800 in accordance with some embodiments of the present disclosure.

The AR headset 920 provides an improved human interface for performing navigated surgical procedures. The AR headset 920 can be configured to provide functionalities, e.g., via the computer platform 910, that include without limitation any one or more of: identification of hand gesture based commands and/or voice based commands, display AR graphical objects as an overlay which may be anchored to particular real-world objects viewed through the display screen 1450 and associated optics, display images in various defined display regions, display video feeds from cameras mounted to one or more AR headsets 920 and other cameras, and control surgical light (in-built or otherwise connectable), etc.

Electrical components of the AR headset 920 can include one or more cameras 1440, a microphone 1442, a gesture sensor 1444, a pose sensor (e.g., inertial measurement unit (IMU)) 1446, a display module 1448, and a display screen 1450 configured to display images for viewing by the wearer and to allow at least some ambient light to pass therethrough for viewing by the wearer. The one or more cameras 1440 may be configured operate as the gesture sensor 1444 by enabling identification of user hand gestures performed within the field of view of the camera(s) 1440. Alternatively the gesture sensor 1444 may be a proximity sensor and/or a touch sensor that senses hand gestures performed proximately to the gesture sensor 1444 and/or senses physical contact, e.g. tapping on the sensor or the enclosure 1304. The pose sensor 1446, e.g., IMU, may include a multiaxis accelerometer, a tilt sensor, and/or another sensor that can sense rotation and/or acceleration of the AR headset 920 along one or more defined coordinate axes. Some or all of these electrical components may be contained in the component enclosure 1304 or may be contained in another enclosure configured to be worn elsewhere, such as on the hip or shoulder.

As explained above, the surgical system 2 includes a tracking system, e.g., 6/6' in FIG. 12 and tracking subsystem 830 in FIG. 8 and/or computer platform 910, and a surgical robot 4. The tracking system is configured to determine a pose of an anatomical structure and a pose of an end effector and/or a surgical tool. The surgical robot 4 includes one or more navigation controllers e.g., 828 in FIG. 14, that are configured to determine a target pose for the surgical tool based on a surgical plan, e.g., from a surgical planning function performed by the computer platform 910 of FIG. 9, defining where a surgical procedure is to be performed using the surgical tool on the anatomical structure and based on the pose of the anatomical structure. The one or more navigation controllers are further configured to generate steering information based on the target pose for the surgical tool, the pose of the anatomical structure, and the pose of the surgical tool and/or the end effector, the steering information indicating where the surgical tool and/or the end effector need to be moved under control of the at least one motor.

The electrical components of AR headset 920 can be operatively connected to the electrical components of the computer platform 910 through a wired/wireless interface 1452. The electrical components of AR headset 920 may be operatively connected, e.g., through the computer platform 910 or directly, to various imaging devices, e.g., the C-arm imaging device 104, the I/O-arm imaging device 106, the image database 950, and/or to other medical equipment through the wired/wireless interface 1452.

The surgical system 2 further includes at least one AR headset controller 1430 (also referred to as "AR headset controller" for brevity) that is may reside in the AR headset 920 and/or in the computer platform 910. The AR headset controller 1430 is configured to receive navigation information from the navigation controller 828 which provides guidance to the user during the surgical procedure on an anatomical structure, and is configured to generate an AR image based on the navigation information for display on the see-through display screen 1450.

The see-through display screen (also referred to as "display screen") 1450 is configured to display objects through an optical system in a manner such that when the wearer looks therethrough, the object appears to be displayed in the real world. The optical system can be positioned by the headband 1306 directly placed in front of the wearer's eyes. Various functionality is provided by software executed by the AR headset controller 1430 which can reside in the AR headset 920 and/or in an external component connected via wired cables and/or wireless communication links.

The AR headset controller 1430 can be within a housing that is configured to be worn on a user's head or elsewhere on the user's body while viewing the display screen 1450 or may be remotely located from the user viewing the display screen while being communicatively connected to the display screen 1450. The AR headset controller 1430 can be configured to operationally process signaling from the cameras 1440, the microphone 142, and/or the pose sensor 1446, and is connected to display AR images on the display screen 1450, e.g., via the display module 1448. Thus, the AR headset controller 1430 illustrated as a block within the AR headset 920 is to be understood as being operationally connected to other illustrated components of the AR headset 920 but not necessarily residing within a common housing or being transportable by a user. For example, the AR headset controller 1430 may reside within the computer platform 910 which, in turn, may reside with the housing of the computer tracking system 6' shown in FIGS. 3B and 3C.

Example Wearer Views Through the AR Headset

FIGS. 15-25 illustrate example views provided to the wearer through the display screen 1450 of the AR headset 920 in accordance with some embodiments of the present disclosure.

One potential drawback of using an AR headset in an operating room is the potential for bright ambient lighting to "wash-out" or reduce the contrast of displayed objects. These potential drawbacks can be reduced or eliminated by some embodiments described below where the display screen 1450 is configured to have horizontal bands of differing light transmissivity (opaqueness) and/or where attachable components of varying size adjust opacity of the user's view through the display screen 1450. These darkened band(s) of the optical system can function to increase the contrast of displayed objects to, for example, enable a surgeon to more accurately view medical radiographs.

In one illustrative embodiment, the see-through display screen 1450 is configured with at least two laterally extending bands, where an upper one of the at least two laterally extending bands has a lower light transmissivity, e.g., darker, (more opaqueness) than a lower one of the at least two laterally extending bands which constrain incident ambient light passing therethrough for viewing by the user. The at least one AR headset controller 1430 can be configured to display two dimensional images in the upper one of the at least two laterally extending bands and to display a three dimensional model of the anatomical structure provided by the at least one navigation controller 1430.

The AR headset user interface further enables sterile software control and salient display of information features that address limitations of current navigation technology. Additionally, as described below, operational functionality is provided that enables wearers to virtually interact with navigation elements using hands, surgical instruments, and/or other objects.

The AR headset operations can display both 2D images and 3D models in the different bands. The 2D images may preferably be displayed in a more opaque band (upper band of the display screen optics) and the 3D model may be more preferably displayed in the more transparent band, otherwise known as the environmental region (bottom band of the display screen optics). Below this band where the display screen optics end, the wearer has an unobstructed view of the patient. It is noted that the separate bands are fluidic. It is possible that the 3D content moves to the opaque band depending on the position of the headset relative to the content, and 2D content can be placed in the transparent band and stabilized to the real world. Additionally, the entire display screen optics can be darkened to convert the headset into virtual reality for surgical planning or completely transparent during the operation. Any of the controls can be found in any of the band depending on the wearer's preference.

Figure 15:
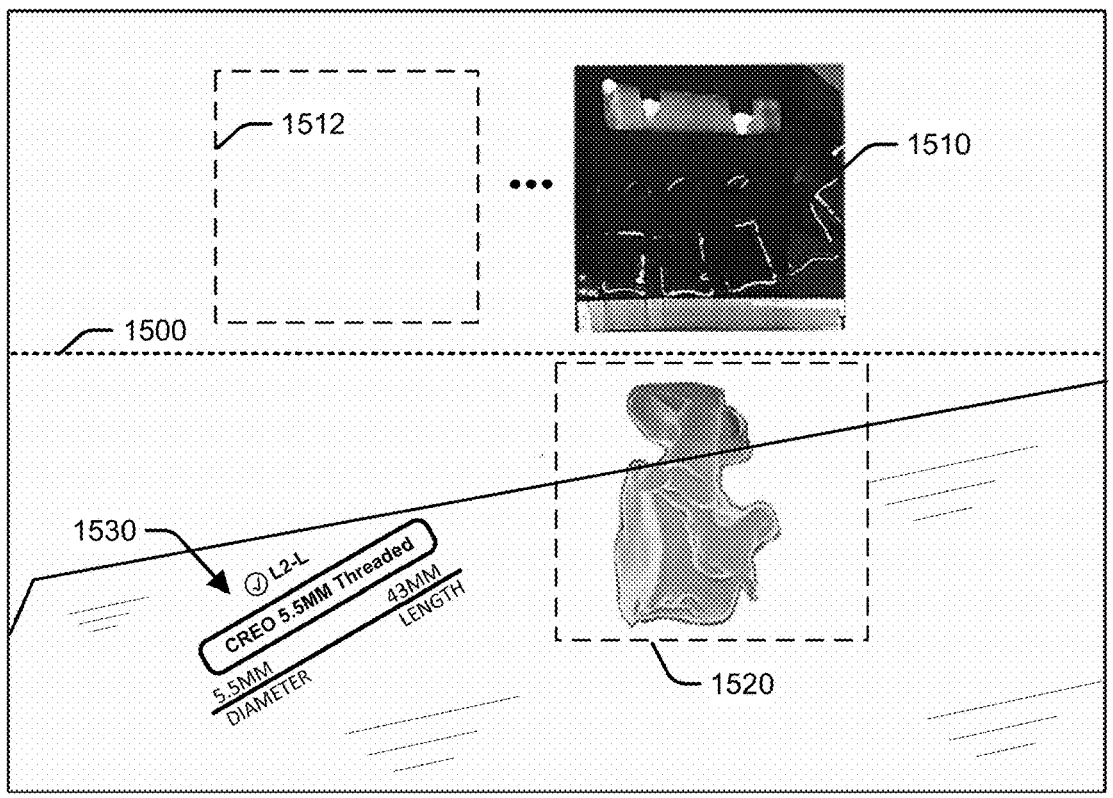
FIGS. 15-25 illustrate example views through the display screen of an AR headset in accordance with some embodiments of the present disclosure.

FIG. 15 illustrates two laterally extending bands across the display screen 1450 that are divided along dashed line 1500. Although not illustrated by shading in FIG. 15, it is to be understood that the upper one of the at least two laterally extending bands has a lower light transmissivity (e.g., darker shading) than a lower one of the at least two laterally extending bands to reduce the amount of incident ambient light passing therethrough for viewing by the user. The at least one AR headset controller 1430 has displayed a plurality of two dimensional images in screen areas 1510 and 1512 within the upper one of the at least two laterally extending bands. The at least one AR headset controller 1430 has also displayed a three dimensional model of the anatomical structure in another screen area 1520 in the lower one of the at least two laterally extending bands, and displayed implant information 1530 identifying characteristics of a planned implant that is to be used in a surgical procedure. Displayed implant information 1530 identifies that a CEO threaded screw having diameter 5.5 mm and length 43 mm is planned to be implanted in spine location L2-L.

FIGS. 16-19 illustrate example operations for a wearer to interact with various objects that are displayed on the display screen 1450 of the AR headset 920.

The AR headset 920 can be configured to provide hand-tracking which enables the wearer to naturally and in a sterile-fashion interact with software functionality of the surgical system 2. These operations may be provided through processing of the video streams from the camera(s) 1440 of AR headset 920. The AR headset controller 1430 can be configured to identify and respond to a plurality of different hand based gestures, including but not limited to pinching, pushing, hand-signals, pre-defined motions (hand flipping).

The wearer can access different menus and sub-menus and perform specific functions, such as menu selection, menu manipulation/re-positioning, image manipulation/re-positioning, and virtual projection manipulation/re-positioning. An example recognizable hand gesture can be pinching, which can be formed by the thumb and index finger connected with the other three fingers raised (shown in FIG. 16). Specifying a specific hand gesture reduces the chance of false-positives when interacting with the gesture recognition functional software, especially in the operating room where a user will need to occasionally rest hands in the field-of-view of the camera(s) 1440. Hand gestures can be performed with either hand or both hands. Hand-tracking functionality may be displayed to the surgeon by augmenting different hand models over the hands (glove, mesh, ball-and-stick model).

In one embodiment, the gesture sensor 1444, which can include the camera(s) 1440, is configured to output to the AR headset controller 1430 an indication of a hand gesture formed by the user. The AR headset controller 1430 is configured to control graphical objects displayed on the display screen 1450 responsive to recognition of the hand gesture.

As explained above, the gesture sensor 1444 can include the camera(s) 1440 mounted to face away from the user to output a video stream of the user's hand while positioned in front of the AR headset 920 within a field-of-view of the camera(s) 1440. The AR headset controller 1430 can be configured to associate different recognizable hand gestures to different ones of a plurality of operations that control the graphical objects displayed on the display screen 1450. The plurality of operations may include at least one of the following: user command to expand a menu item 1530 in that is displayed on the display screen into a list of sub-menu items that are then displayed on the display screen; user command to select a menu item and/or one of a plurality of sub-menu item that is displayed on the display screen; and user command to operationally control size, location, and/or orientation of one of the graphical objects that is displayed on the display screen.

The AR headset controller 1430 can be configured to display a computer generated hand model on the display screen with a pose that is dynamically updated to track a present pose of the user's hand identified in the video stream from the camera.

In a further embodiment, the AR headset controller 1430 is configured to associate a recognizable hand gesture to a command to select a surgical implant from among a set of surgical implants that can be used for implantation into the anatomical structure, and to display a graphical representation of the surgical implant that is select on the display screen 1450. In another embodiment, the AR headset controller 1430 is configured to associate different recognizable hand gestures to different ones of a plurality of operations by the surgical system, where the plurality of operations includes at least one of the following: command to control imaging of the anatomical structure by an imaging system; command to control which of a plurality of images of the anatomical structure is displayed on the display screen; and command to control movement of the robot arm of the surgical robot relative to the anatomical structure.

Figure 16:
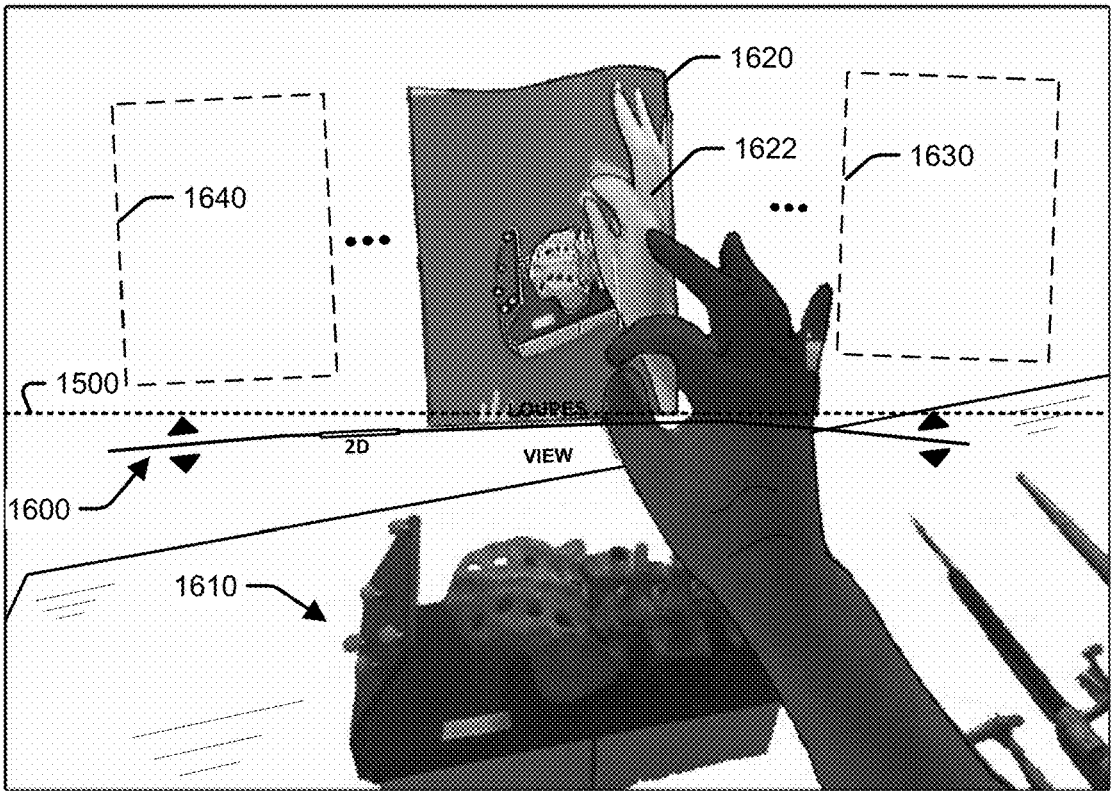

In FIG. 16, the AR headset controller 1430 has displayed a plurality of images in screen areas 1620, 1630, and 1640. In screen area 1620 the AR headset controller 1430 has rendered a computer generated hand model 1622 of the user's hand forming a pinch gesture displayed as a graphical overlay on video of a real-world object 1610, e.g., anatomical structure that resides on a table and viewed by the camera(s) 1440. The recognized pension gesture may be used to select among user selectable indicia display along a navigation bar 1600 under control location, size, and/or other characteristics of the screen areas 1620, 1630, and 1640.

Typically, surgeons also wear helmets with attached surgical headlights to improve visualization of the patient. In one variant, the headlight can be part of the AR headset 920 or connected thereto. The AR headset 920 may be configured to control the brightness setting of the light via an external control or through AR controls that include gesture-based command recognition and/or voice based command recognition.

The AR headset wearer may use gesture-based commands and/or voice based commands, which are identifiable by the AR headset controller 1430, to change characteristics of a surgical tool and/or an implant device. For example, a surgeon may say "Change screw length to 6.5" to cause the screw length that is displayed in the display screen 1450 to be changed to indicate a size, shape, and/or pose that correspond to the requested screw length.

Augmented Navigation Operations

The AR headset user interface further enables sterile software control and salient display of information features that address limitations of current navigation technology. Additionally, as described below, operational functionality is provided that enables wearers to virtually interact with navigation elements using hands and surgical instruments.

Figure 17:
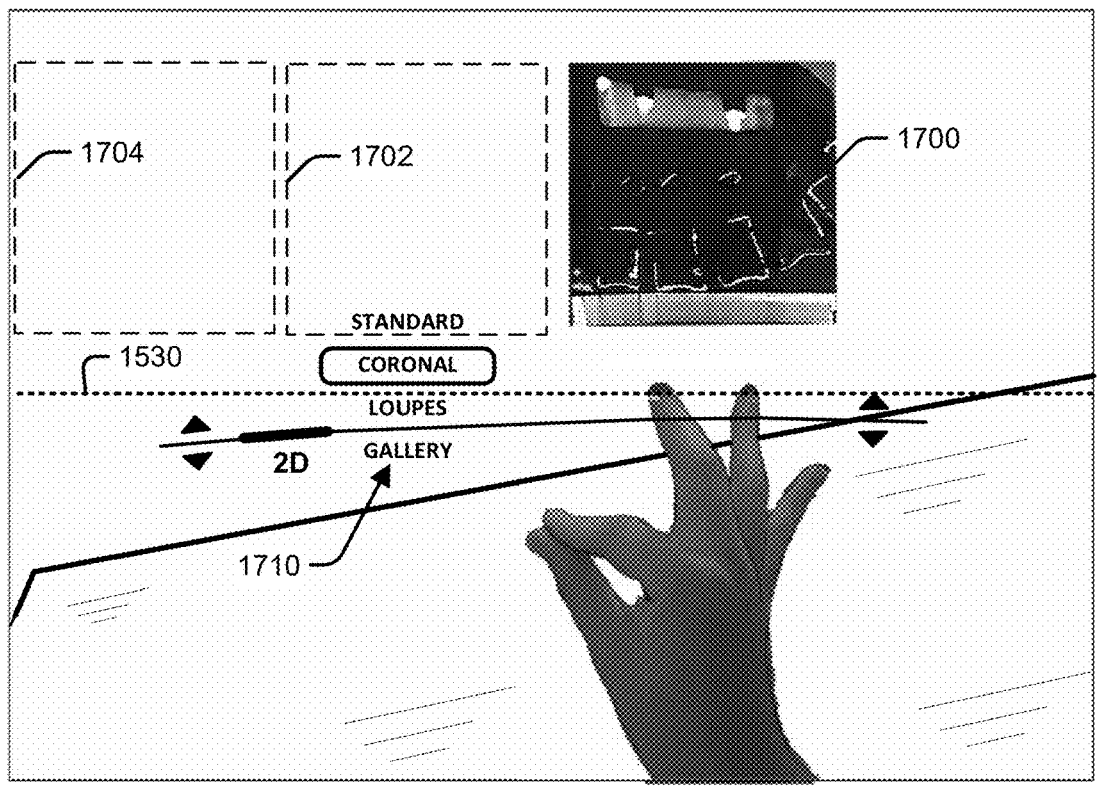

FIG. 17 depicts what a wearer may see through the display screen 1430. In the upper band, which can be more opaque than the lower band, the software displays images for navigation, the standard being axial and sagittal views for spine navigation, but any and multiple 2D planes can be shown, such as the coronal plane (depicted in FIG. 16). These images could be modified based on the needs of different procedures, such as arthroplasty. The images can be zoomed into and panned by the use of hand gestures. Additional views can be accessed through a displayed dropdown list 1710 via hand gestures. The wearer can select the digital loupes view as well as an image gallery from among the list 1710. In this gallery, the wearer is able to view images and manipulate images associated with the patient. For three dimensional (3D) images such as MRI/CT scans, the wearer can scroll through the slices using hand gestures. By selecting the two dimensional (2D) tab, the 2D images appear/disappear. By selecting the 3D tab, the 3D reconstructed model appears/disappears.

In the example of FIG. 17, the controller 1430 has displayed a plurality of images in screen areas 1700, 1702, and 1704. The user is using a pinch gesture to select a menu item (e.g., coronal image view) from among a plurality of many items 1710 (listing of available image views including standard, coronal, loupes, and gallery) being displayed on the display screen 1450.

Figure 18:
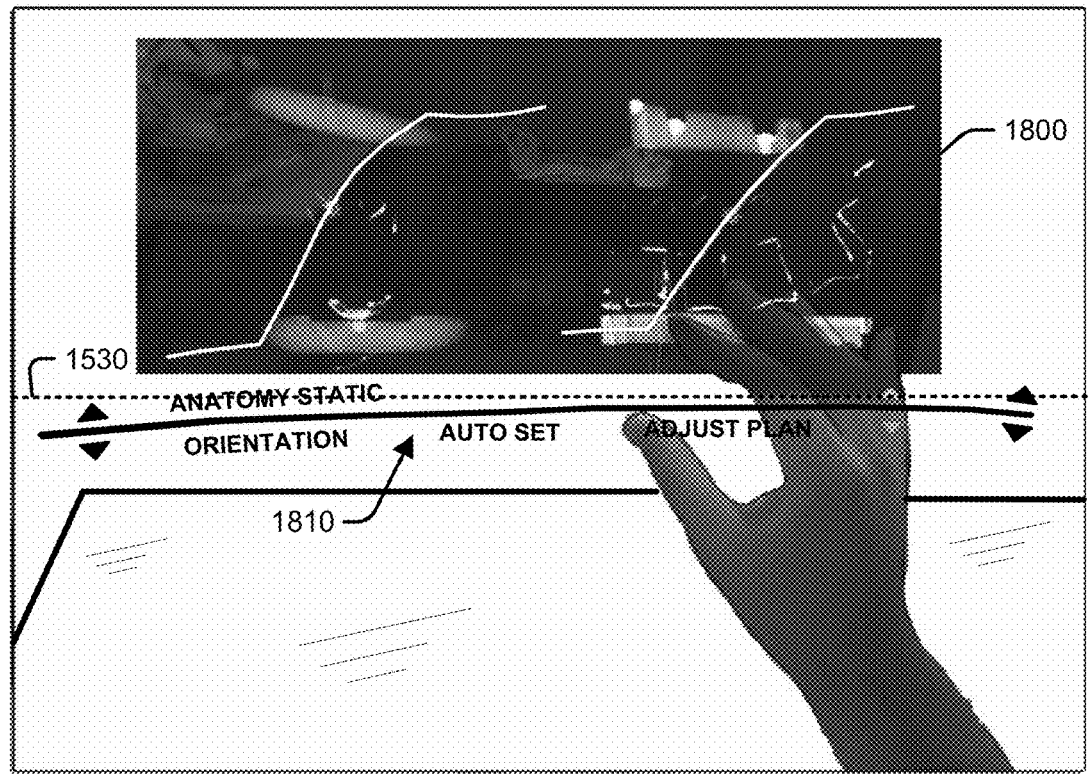

Referring to FIG. 18, the AR headset operations also allow the wearer to modify image properties within the display area 1800, such as window/level and the slicing type (orientation). The wearer can perform these modifications through selectable settings indicia 1810 illustrated in the example view of FIG. 18.

Figure 19:
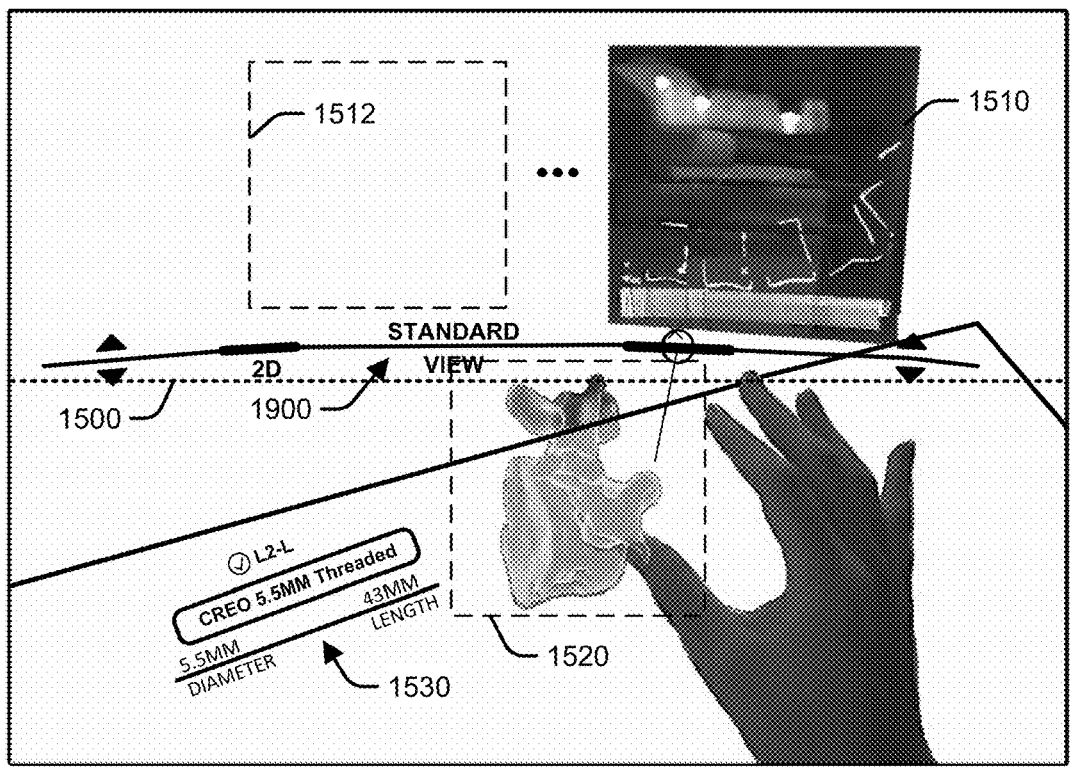

Referring to FIG. 19, when 3D is enabled, a 3D graphical representation of the spine is obtained (which is based on imaging scans) and displayed on the display screen 1450 above the patient. This graphical representation may be configured by the AR headset controller 1430 to be the same size and oriented to have the same pose as the patient's actual anatomy or may be configured to be larger-to-scale, such as 2:1 for enhanced visualization. The graphical representation may be anchored to a location as determined based on a particular navigated reference array, in this case the patient reference array. This anchoring, or world/environment-stabilization may be performed through a combination of both inside-in and outside-in tracking.

An IMU 1446 of the AR headset 920 can be configured to measure the relative orientation of the AR headset 920 (inside-out tracking). The navigation camera 46 of the camera tracking system 6 can be used to track a reference array on the AR headset 920 to measure pose, position and angular orientation, (outside-in tracking). This data can be used to update the projection of the display 3D graphical representation as the wearer's head moves, providing the perception to the wearer that the graphical representation has remained stationary. This type of effect may also be achieved through simultaneous localization and mapping (SLAM) techniques.

In one embodiment, a plurality of the cameras 1440 are spaced apart and mounted to face away from the user. The tracking system 830 is operatively connected to process video streams from the plurality of cameras 1440 and configured to determine a pose of the anatomical structure and a pose of the end effector and/or the surgical tool. The tracking system 830 can be further configured to process the video streams from the plurality of cameras 1440 to determine pose of a reference array connected to the anatomical structure and pose of a reference array connected to the end effector and/or the surgical tool.

In still a further embodiment, the tracking system 830 processes a video stream from the tracking camera(s), e.g., 46 in FIG. 3A and DRA tracking camera 870 in FIG. 8, to determine pose of a reference array connected to the AR headset 920. The AR headset controller 1430 can be configured to control a pose and scale of a three dimensional model of the anatomical structure that is displayed on the display screen 1450 based on the pose of the reference array connected to the anatomical structure and the pose of the reference array connected to the AR headset. The pose sensor 1446 of the AR headset 920 can be configured to output a sensed pose of the AR headset 920, and the AR headset controller 1430 can be operatively connected to the pose sensor 1446 and further configured to control a pose of a three dimensional model of the anatomical structure that is displayed on the display screen 1450 based on the pose of the reference array connected to the anatomical structure and the sensed pose of the AR headset 920.

This allows the wearer's head to move to look at different perspectives of the anatomy. The location and orientation of the graphical representation relative to the anchor can be moved dependent on the wearer's preference and can even be overlaid over patient anatomy. Additionally, in this particular example, the graphical representation is illustrated as being a solid surface, offering enhanced visualization of the surface. In different variants, the graphical representation may be a mesh to allow visualization of inside the anatomical structure, e.g, bone. This 3D graphical representation ultimately provides a more intuitive navigation setup for the wearer instead of on 2D images that burden the wearer to attempt to mentally visualize the 3D anatomical structure.

Figure 20:
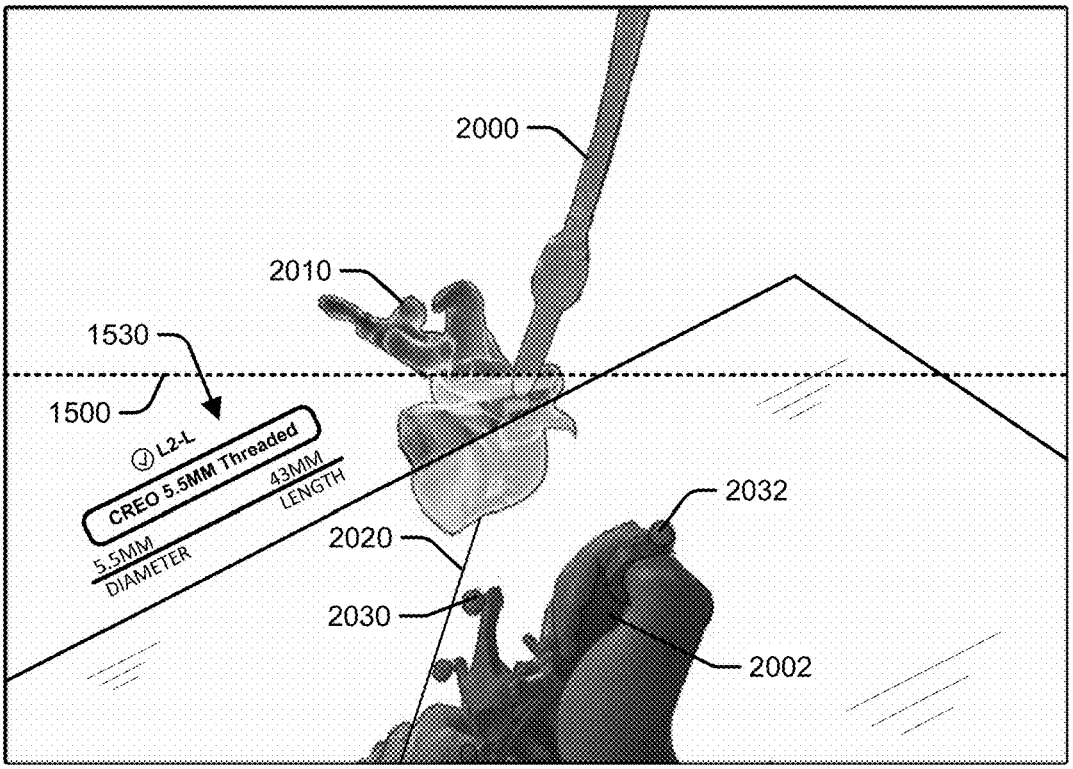

Referring to FIG. 20, when a surgical tool 2002 is brought in vicinity of a tracked anatomical structure and within the field of view of the cameras 1440 (FIG. 14) and 46 (FIG. 6) tracking a reference array 2030 and 2032 connected to the surgical tool 2002, a graphical representation 2000 of the tool can be displayed in 2D and/or 3D images in relation to a graphical representation 2010 of the anatomical structure. A wearer can use the viewed graphical representations to adjust a trajectory 2020, which can be illustrated as extending from the graphical representation 2000 of the tool through the graphical representation 2010 of the anatomical structure. This operation may be performed through the displayed or through a control command, e.g. button, on the instrument. Note that this can be done with the instrument interfacing the patient or the instrument interfacing with the 3D model itself.

Figure 21:
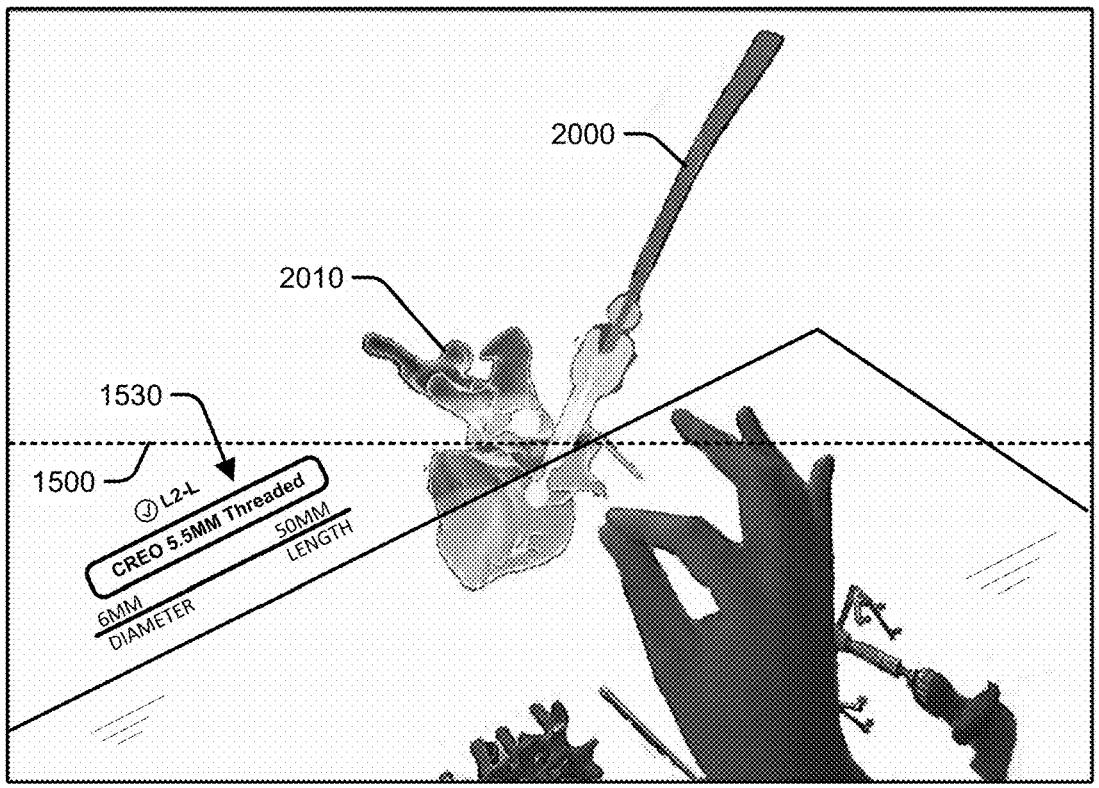
Figure 22:
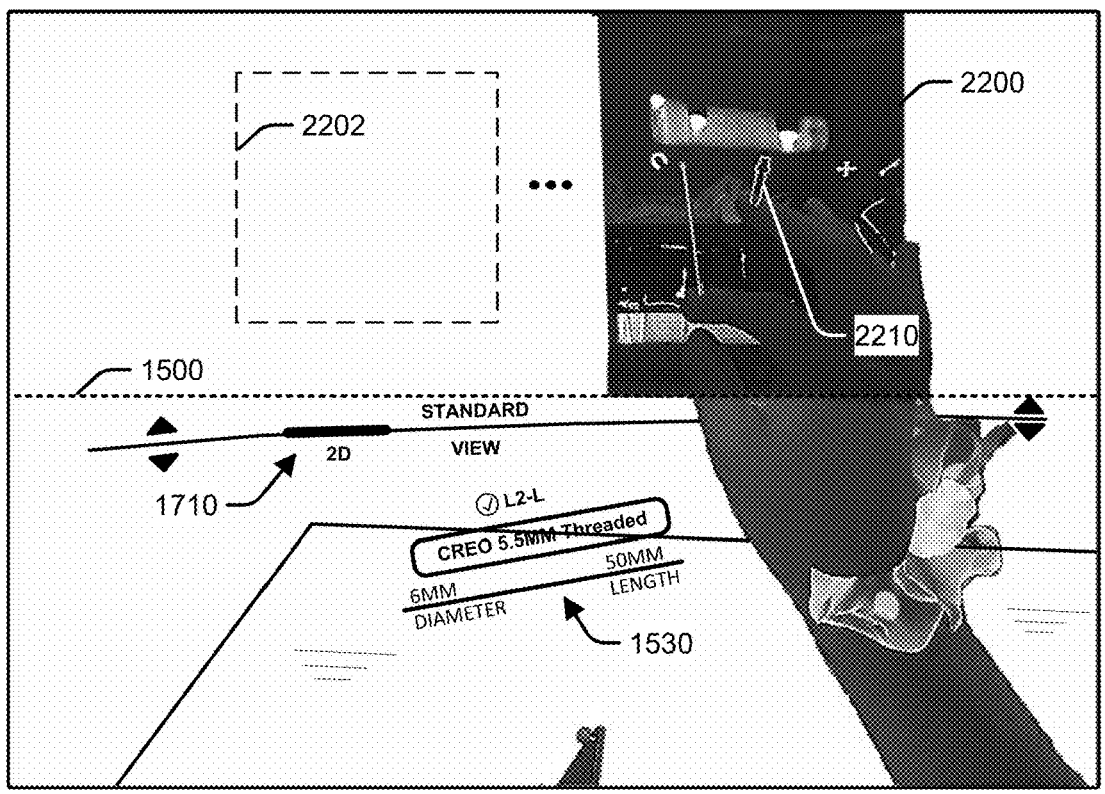

Once a screw trajectory is set, its dimensions (length, width), orientation, and depth can be modified using hand gestures, such as the pinch gesture shown in FIGS. 20 and 21. The trajectory can also be adjusted in the 2D images as well, as shown in FIG. 22. For example, in FIG. 22 a wearer has formed a hand gesture, e.g., pinch, that is interpreted as a command to select a smaller size type (e.g., smaller diameter and/or length) of screw which is then updated in the graphical representation 2210 of the screw shown as an overlay on the medical image 2200 and/or displayed in another graphical area 2202. Note that in these examples, a screw is used as the implant, but the implant can alternatively include, but not limited to, spacers, rods, and prostheses.

Figure 23:
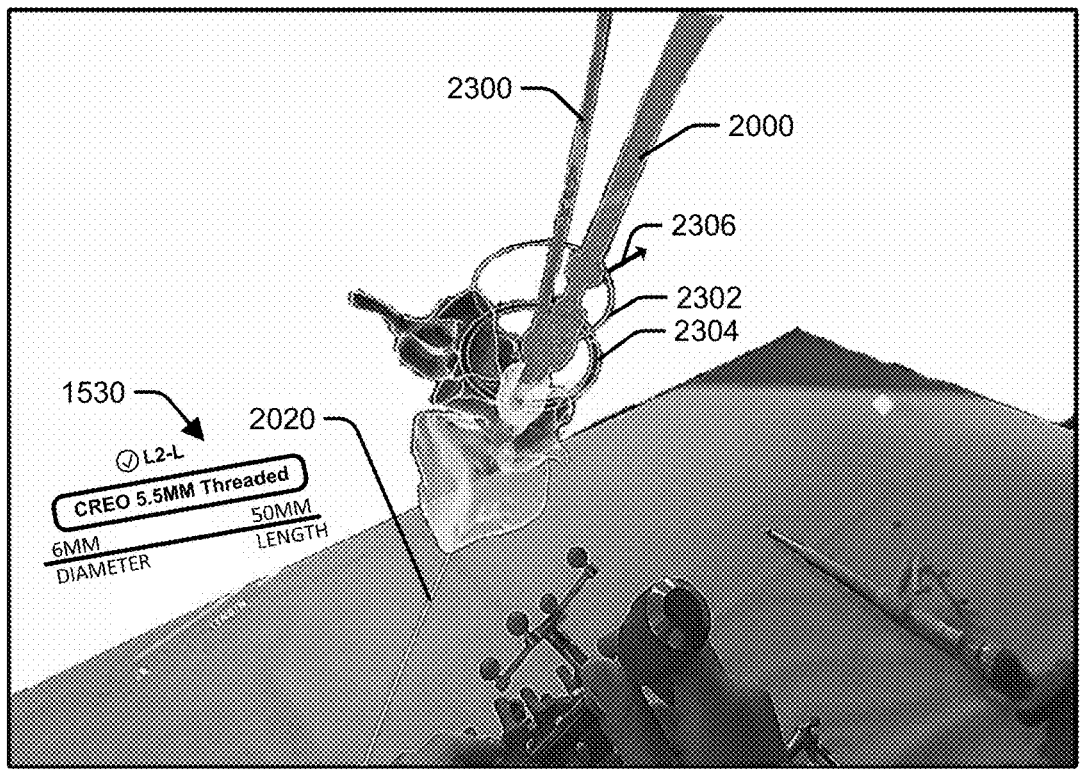

Referring to FIG. 23, once the trajectory is set, when another navigated tool 2300 comes within vicinity of the planned trajectory 2020 of the tool 2002 (illustrated as object 2000), an augmented trajectory guidance interface is displayed to help the wearer position the tool 2300 to the same trajectory 2020. In a particular example of FIG. 23, a graphical indicator 2306 appears instructing which direction to move the instrument 2300 until the outer circle 2302 aligns with the inner circle 2304. Once these circles 2302 and 2304 are aligned, the wearer can then be instructed to push the instrument 2300 down into the patient until the circles 2302 and 2304 are aligned (e.g., become concentric), thus indicating the target depth is reached. There are other possible approaches to this trajectory guidance, including but not limited to arrows pointing towards the desired trajectory and color gradients. Once the implant is placed, the wearer can select and move to a next step of the operation procedure.

Figure 24:
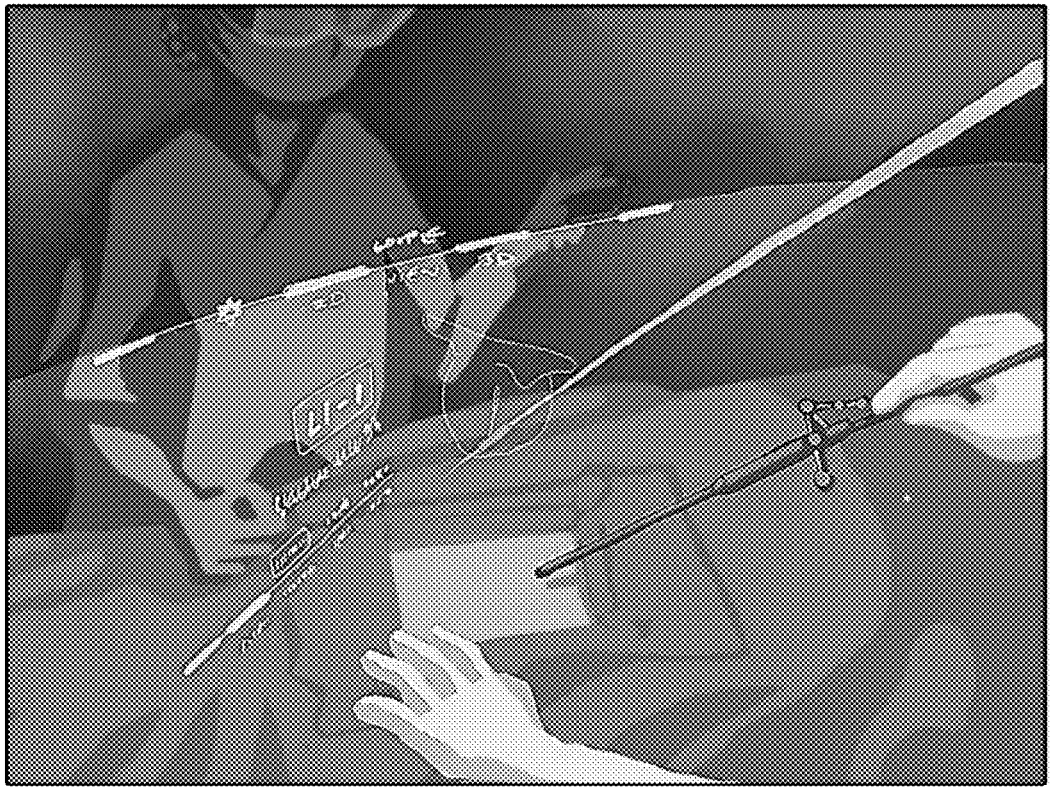

Referring to FIG. 24, the system operational functionality can enable a plurality of the AR headsets to be used in defined combined operational modes, including any one or more of: a collaboration mode, a teaching mode, and an independent mode. In a collaboration mode, a secondary wearer wearing a second AR headset has the ability to interface through the second AR headset to the control the display interface of a first AR headset worn by a primary wearer. As shown in FIG. 24, the secondary wearer sees the same 3D model and relevant controls stabilized to the environment that is second by the primary wearer, the only difference being the content is flipped to be legible from his/her perspective. The secondary wearer can perform all trajectory modification actions as described previously which will update the primary wearer's view through the first AR headset. In teaching mode, the primary wearer can change his/her view that is provided through the first AR headset to the second AR headset for viewing by the secondary user, such as to enable the second AR headset to display the images/scans from the perspective of the secondary wearer, and vice-versa. In independent mode, the views provided by the first and second AR headsets are controlled independent of each other, which enables the two wearers to perform independent navigation simultaneously.

For example, in one embodiment the surgical system 2 includes first and second AR headsets. At least one AR headset controller, one of which may reside in or be connected to the first AR headset, is operatively connected to receive a first video stream from the camera of the first AR headset and configured to selective route the first video stream to the display device of the first AR headset and/or to the display device of the second AR headset responsive to electronic commands obtained from a user wearing the first AR headset. The least one AR headset controller, one of which may reside in or be connected to the second AR headset, is operatively connected to receive a second video stream from the camera of the second AR headset and configured to selective route the second video stream to the display device of the first AR headset and/or to the display device of the second AR headset responsive to electronic commands obtained from a user wearing the second AR headset.

Figure 25:
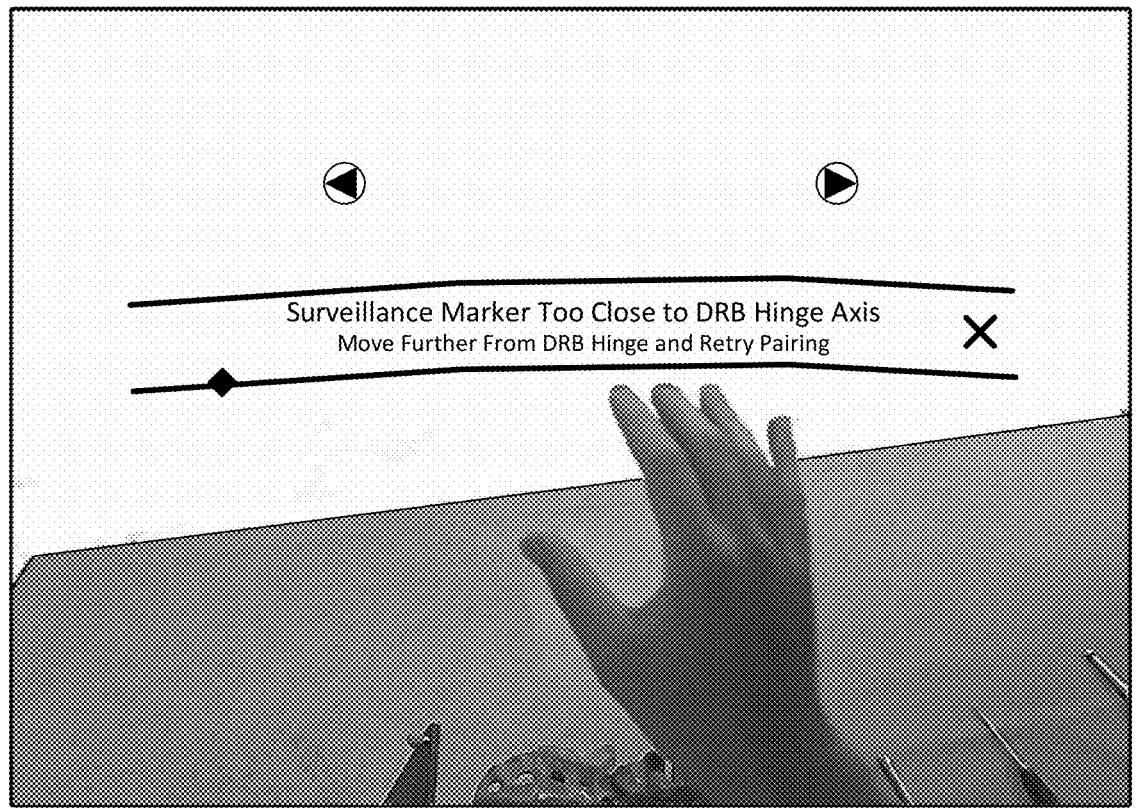

Referring to FIG. 25, the at least one AR headset controller can be configured to display notifications and warnings to the wearer within his/her field-of-view. Such warnings can inform, for example, that the patient reference array has moved, navigation integrity is lost, one or more reference arrays cannot be seen, potential for robot collision is predicted, etc. These notifications may be displayed on the display screen 1450 with or without affecting the operation of the user interface provided through the AR headset 920.

As explained above, the AR headset 920 and associated operations not only support navigated procedures, but also can be performed in conjunction with robotically assisted procedures. In the latter case, the pre-operative plan is loaded from the computer platform 910. The software shows the wearer the entire plan in 3D with the planned implants. The wearer can select the screw or provide adjustment to a surgical plan. Once the plan is finalized, the wearer through either the AR interface, foot-pedal, or other controls moves the robot onto the planned trajectory to guide placement of additional tools.

Surgical Tool Navigation Operations Using AR Headset

Various operations that can be performed by the surgical system 2 to provide navigation assistance through AR headset for a surgical tool during a medical procedure are now described with reference to the example embodiments of FIGS. 26-31.

Some embodiments may enable an AR headset wearer to accurately navigate a surgical tool to a target vector location within the reference space using AR overlaid 3D navigation objects, also referred to as an iron sight. The overlaid 3D navigation objects can provide amplified visual feedback to enable a wearer to correct tool depth, angle, and tip position relative to the operative navigation trajectory.

A surgeon can plan a trajectory, e.g., via a surgical procedure planning function of the computer platform 910, that defines a specific vector position on a patient anatomical image. The image is localized to a patient static reference array which carries over the position of the vector. The patient static reference array is tracked by the cameras and compared to another tracked array connected to a surgical tool.

Figure 26:
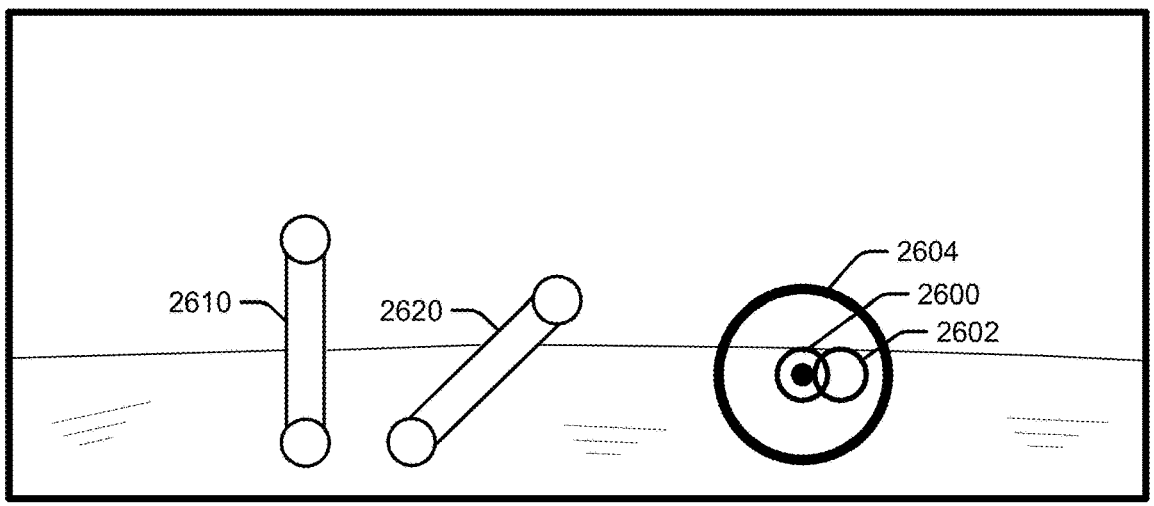
FIGS. 26-31 illustrate example views through the display screen of an AR headset for providing navigation assistance for a surgical tool during a medical procedure in accordance with some embodiments of the present disclosure.
Figure 27:
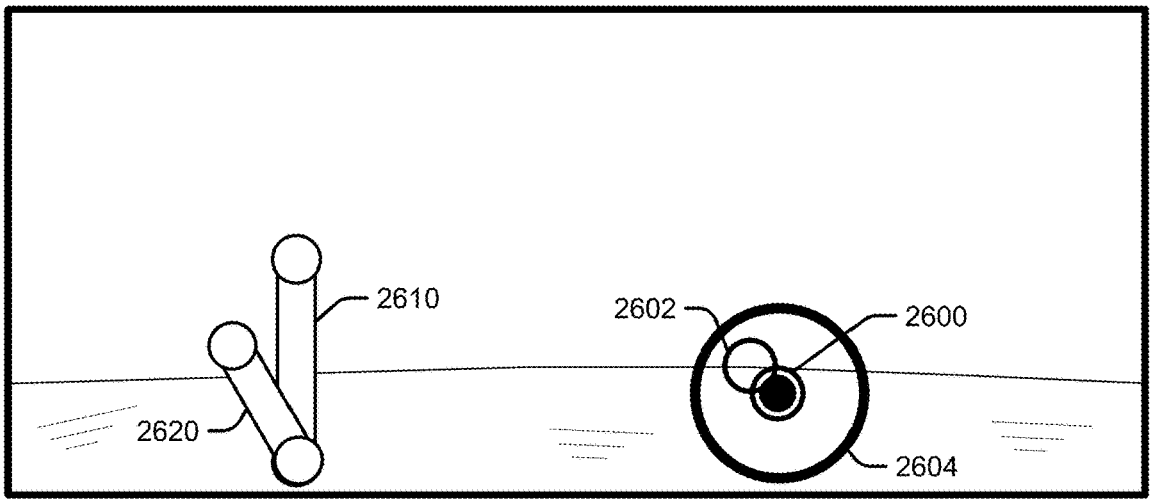
Figure 28:
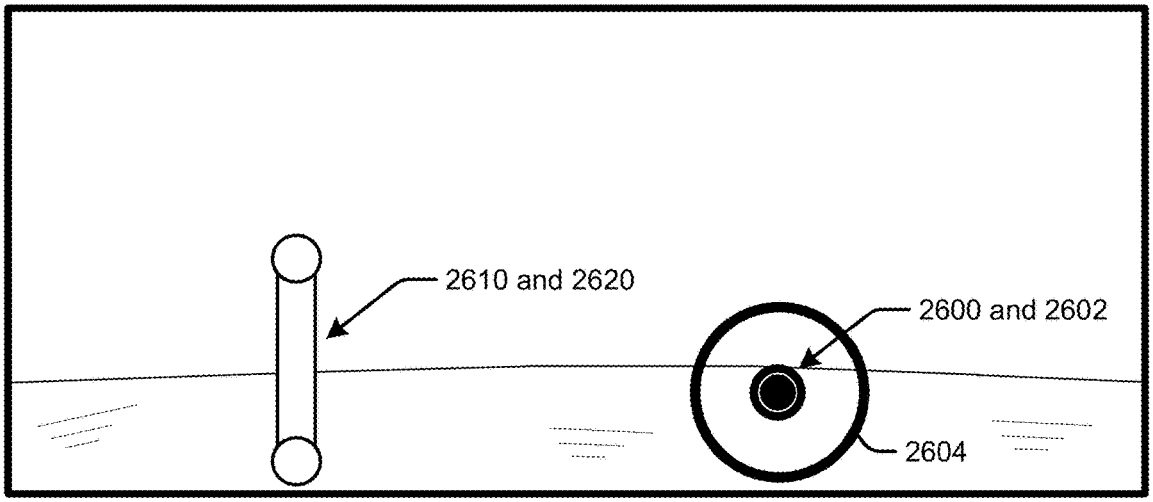

FIGS. 26-28 illustrate graphical objects that can be displayed on the display screen of the AR headset to provide navigation assistance for positioning a surgical tool. The graphical objects include elongated objects, lines, circles, text, and other indicia that are displayed in relative positions that indicate planned versus present poses (e.g., position and angular orientation) of the surgical tool. Various embodiments can guide a user's positioning of the surgical tool relative to a planned location on the anatomical structure and guide the user's movement of the surgical tool along a planned trajectory.

As shown in FIG. 26, the depiction of the present tool position is not aligned properly in terms of trajectory with the planned position, such that the distal end of the tool is off trajectory from the planned position. The circles on the right side of the image provide the following indications. A small circle 2600 indicates the planned tool tip position, and is surrounded by a medium-size circle 2604 indicating the overall tool trajectory and position of the distal end of the tool. The circle 2602 to the right indicates the present position of the tool, which illustrates that the proximal end of the tool is closer in proximity to the planned position while the distal end of the tool is off axis or off trajectory.

Corresponding operations by the AR headset controller 1430 can include to display on the display screen 1450 a graphical representation of the target pose for the surgical tool and display on the display screen 1450 a graphical representation of the pose of the surgical tool. The AR headset controller 1430 can be configured to determine a trajectory offset distance between where a planned trajectory of the target pose for the surgical tool intersects a target location on the anatomical structure and where a trajectory of the pose of the surgical tool intersects the target location on the anatomical structure.

The AR headset controller 1430 can be configured to display each of the graphical representations of the target pose for the surgical tool and the pose of the surgical tool as elongated objects 2610 and 2620 (e.g., rectangular lines) each having a major axis extending between opposite ends, and control spacing between where one end of the elongated objects are displayed on the display screen responsive to the trajectory offset distance. For example, as shown in FIG. 26, object 2610 can indicate a planned pose of the surgical tool and object 2620 can indicate a present pose of the surgical tool.

In one embodiment, the AR headset controller 1430 is configured to control an angle of incline between the elongated objects 2610 and 2620 displayed on the display screen responsive to an angle between the planned trajectory of the target pose for the surgical tool and the trajectory of the pose of the surgical tool.

In another embodiment, the AR headset controller 1430 is configured to display each of the graphical representations of the target pose for the surgical tool and the pose of the surgical tool as circular objects 2602-2604 and control spacing between centers of the circular objects displayed on the display screen responsive to the trajectory offset distance.

In another embodiment, the AR headset controller 1430 is configured to display the graphical representations of the target pose for the surgical tool and the pose of the surgical tool as objects that are spaced apart by a distance indicating an offset from a tip of the surgical tool to the target location on the anatomical structure.

FIG. 27 illustrates that the proximal tips of the planned and present locations of the surgical tool overlap, while the present pose 2620 of the surgical tool is inclined relative to the planned pose 2610.

Using the visual navigation information, the wearer moves the tool toward the planned pose, and as the present pose converges toward the planned pose, the convergence causes the displayed circles to converge become concentric with each other. As the circles overlay, the circles correspondingly become more filled, such as shown in FIG. 28. FIG. 28 further illustrates that the proximal tips of the planned and present locations of the surgical tool overlap, and that the present pose of the surgical tool is coincident with the planned pose, such that the present pose of the surgical tool is accurately aligned with the planned pose.

In some additional or alternative embodiments, the AR headset controller 1430 is configured to display the graphical representations of the target pose for the surgical tool and the pose of the surgical tool relative to three orthogonal axes representing a three dimensional space. The AR headset controller 1430 controls spacing between where the graphical representations are displayed along a first one of the three orthogonal axes responsive to a depth offset distance between a tip of the surgical tool and the target location on the anatomical structure. The AR headset controller 1430 also controls spacing between where the graphical representations are displayed along a plane formed by a second and third one of the three orthogonal axes responsive to the trajectory offset distance between where a planned trajectory of the target pose for the surgical tool intersects a target location on the anatomical structure and where a trajectory of the pose of the surgical tool intersects the target location on the anatomical structure.

This embodiment uses more data from the camera(s) tracking reference arrays to include depth tracking of the surgical tool in addition to general spatial data. This allows for greater accuracy of navigation to be provided to the wearer as the surgical tool is moved to the planned pose for the surgical procedure. An example flow of operations can include taking the position and angle data from one or more cameras, and projecting the data for display through the display screen 1450. In the illustrated example of FIG. 29, a planned tool trajectory line 2900 is displayed along with three depth circles 2910, 2912, and 2914. Depth circle 2910 indicates a present depth of a reference array 2930 connected to a surgical tool 2932, relative to the depth circle 2912 indicating a present depth of a tip of the surgical tool 2932, and relative to the depth circle 2914 indicating a planned maximum insertion depth of the tip of the tool 2932. Offset circles 2920 and 2922 are displayed which indicate an offset between a reference array 2930 attach to a surgical tool 2932 and the planned tool trajectory line 2900.

An objective of the illustrated navigation operation is to visually amplify the depth, angle, and tooltip position correction so that the wearer can more accurately lineup the tool to the planned trajectory 2900 and then navigate the tool downward to the planned maximum insertion depth within the anatomical structure. The displayed offset circles 2920 and 2922 are dynamically modified to indicate that the offset between the tool tip and tool of the tool relative to the trajectory 2900 is decreasing as the tool is moved closer to the planned trajectory 2900. After the tool become sufficiently aligned with the planned trajectory 2900, the wearer then moves the tool downward along the trajectory 2900 until the depth circles 2912 and 2914 converge at the planned maximum insertion depth.

Figure 29:
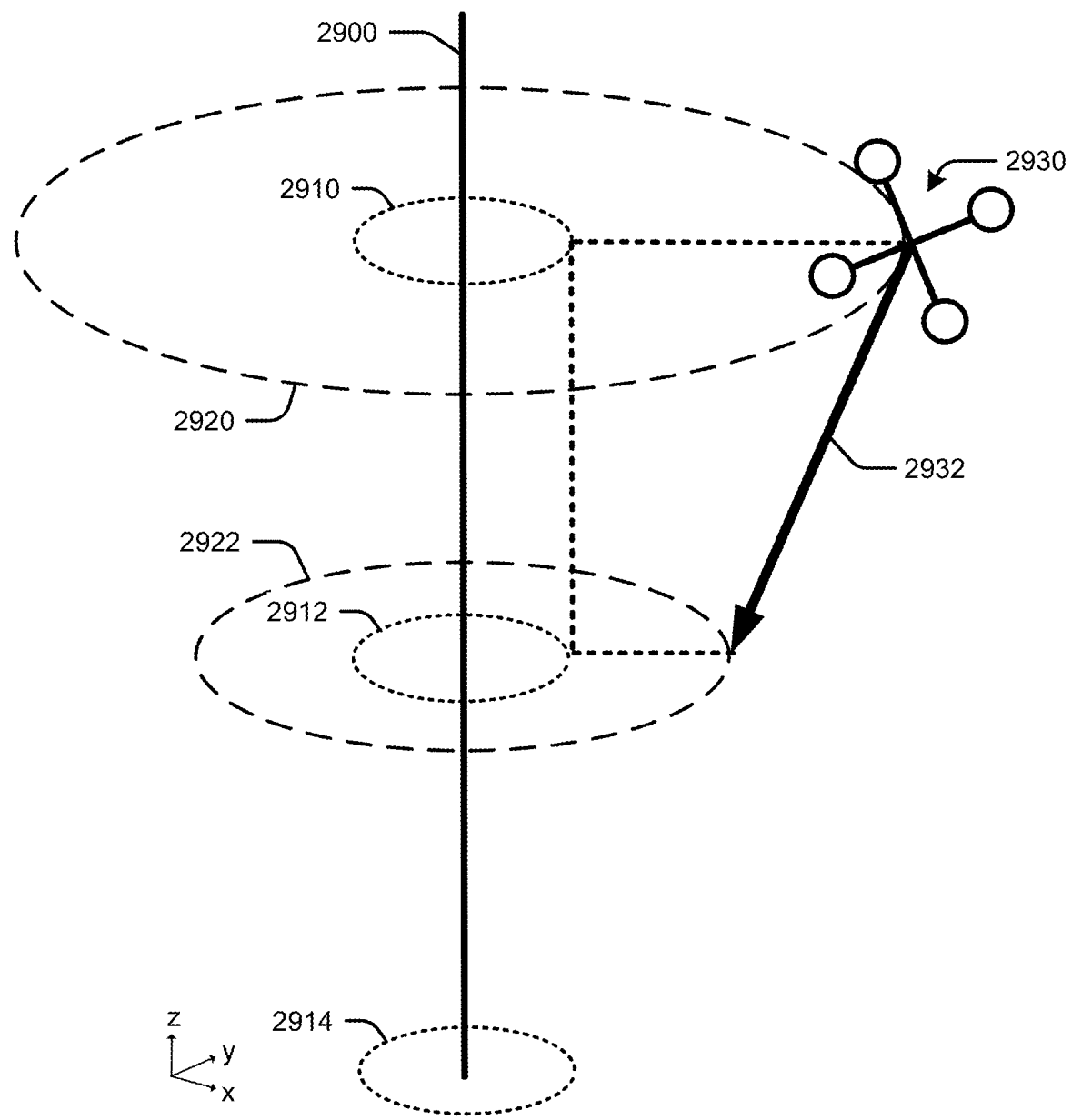
Figure 30:
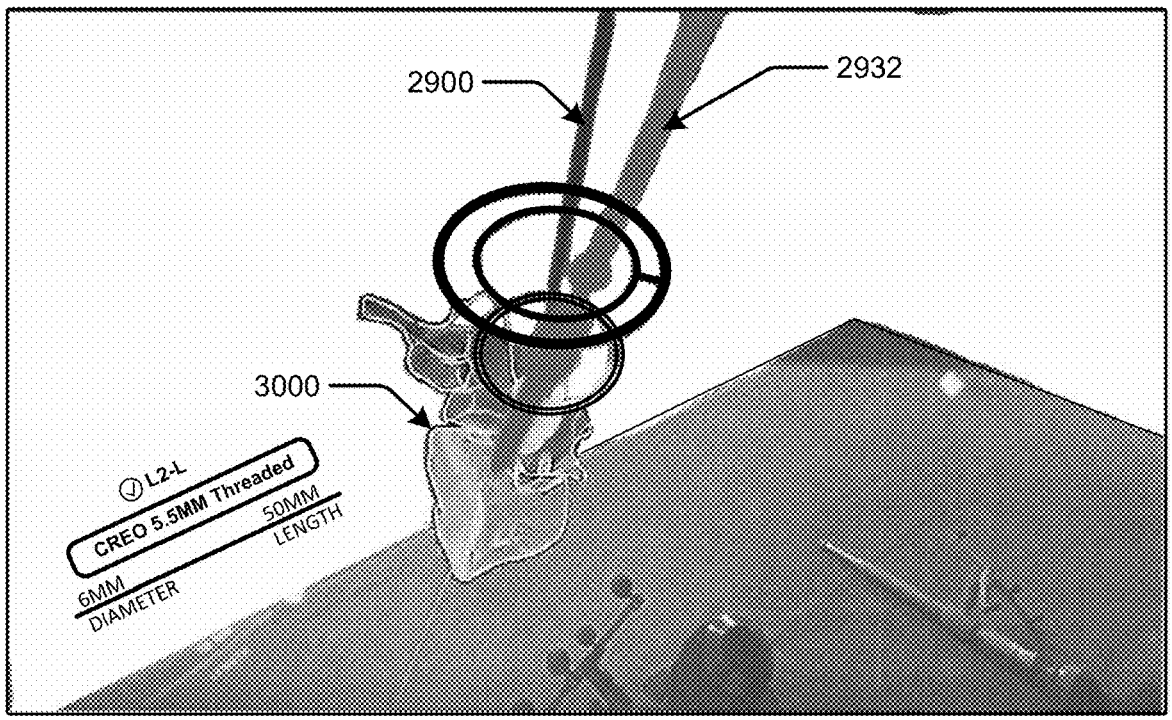

FIG. 30 illustrates a graphic representation of an anatomical structure 3000, e.g., spinal vertebra, and the present position of a tool 2932 relative to a planned tool trajectory 2900. The offset circles, 2920 and 2922 and depth circles 2912 and 2914 of FIG. 29, are also illustrated in FIG. 30 providing navigation guidance to the wearer for moving the tool 2932 to become aligned with the planned tool trajectory 2900. The present tool tip position is illustrated as coinciding with the planned tool trajectory 2900, i.e., the tip location or lower depth rings can be seen to be in the correct position whereas the upper rings are shown to be offset.

Figure 31:
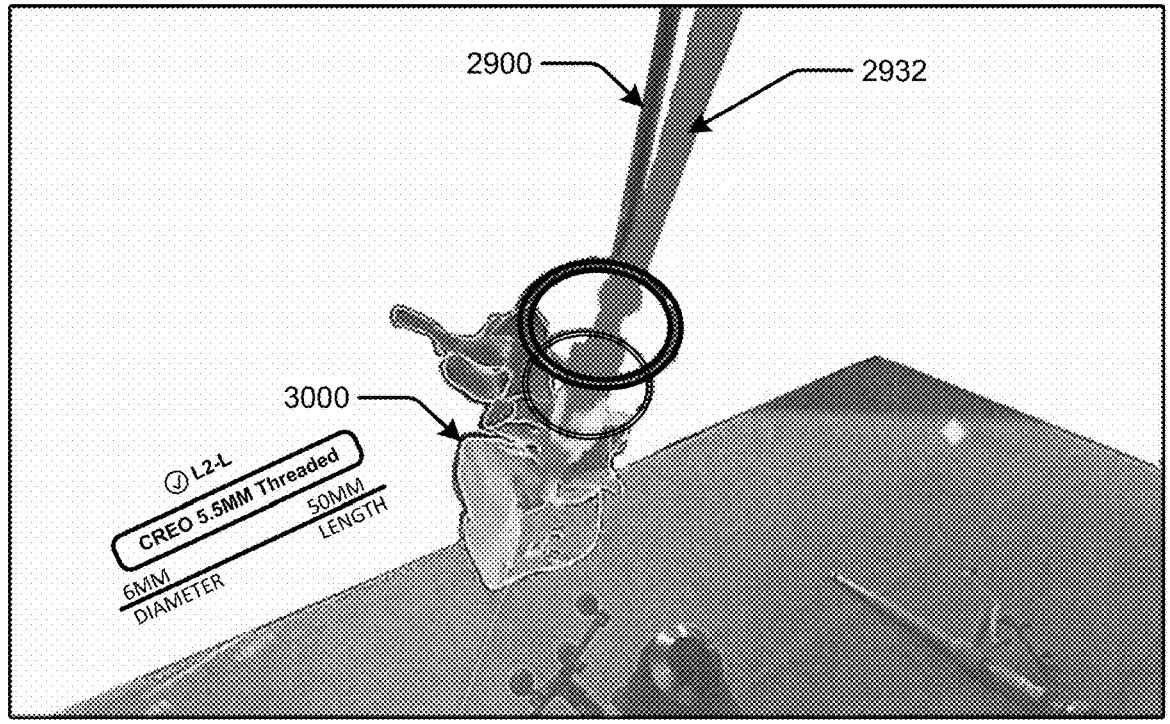

FIG. 31 illustrates a subsequent view of the graphic representation of the anatomical structure 3000 after the wearer has moved the tool 2932 to become aligned with the planned tool trajectory 2900, such that offset circles of FIG. 29 have become concentric. The surgeon can then move the tool 2932 downward along the planned tool trajectory 2900 until the depth circles of FIG. 29 are aligned.

The offset circles and/or depth circles may be rendered using color coding, e.g. changing from red to green, as they become aligned with proper positioning.

Cross-Platform Integration of Medical Devices Using AR Headset(s)

Various further embodiments are directed to providing cross-platform integration of medical devices using one or more AR headsets. These operations may avoid a medical personnel feeling the need to remove the AR headset in order to perform certain actions with one or more medical devices and the operating room, such when navigating an imaging system to capture a desired patient image. Such intermittent removal of AR headset for interacting with a patient or an imaging system interface can raise issues with sterility and great undesirable interruptions between surgical procedure stages, such as while the personnel performs operations to recalibrate the AR headset.

Various embodiments use custom mapped controls that are performed through the AR headset which are configured to navigate user interfaces of imaging systems and other medical devices during a surgical procedure. For example, a wearer can interact with the AR headset using hand gesture commands and/or voice commands to control positioning of an imaging system, to plan an imaging shot on the imaging system, to initiate the imaging shot, and/or to use an obtained imaging shot to plan trajectories for one or more medical implants and associated surgical tools.

Various previously known medical devices, such as various surgical robots and imaging systems are known to provide only a physical user interface for manipulation during planning of a surgical procedure and during implementation performance of the surgical procedure. If the surgeon were wearing an AR headset, the surgeon may feel the need to remove the AR headset in order to travel to and freely control the physical user interface of various medical devices in the operating room.

In accordance with various embodiments herein, the AR headset enables the wearer to enter information and control operation of medical devices which are operatively connected (wired/wireless communication connections) to the AR headset, through hand gesture commands, voice commands, and/or other commands that can be sensed by and/or input to the AR headset. The AR headset thereby enables the wearer to maintain focus on the surgical procedure as it is occurring in front of the wearer and maintain sterility and control of the surgical workflow.

In one embodiment, the AR headset is operatively connected to an imaging system and configured to provide information and/or commands to the imaging system based on identification of hand gesture commands, voice commands, and/or other commands that are sensed by and/or input to the AR headset. Navigation control of the imaging system can be mapped to the virtual space of the AR headset. The AR headset can be used to control movement of the imaging system into a desired position relative to the patient, adjust an imaging shot position, select scan settings for the imaging shot (e.g., patient information, type of scan, etc., and initiate the imaging shot spin through the use of virtual controls that can include hand gestures performed relative to virtual menus displayed on the display screen 1450 and/or voice commands. By using virtual controls, physical contact between the wearer's hands and the imaging system is avoided. For improved safety, a dead-man switch, e.g. a fail-safe switch which prevents movement of the imaging system when released, can be included in the form of a foot pedal for use by the AR headset wearer.

The AR headset can be configured to provide an unencumbered view of the typical field of view in front of the wearer, which can be clear until menus items are initiated responsive to an identified and gesture command, voice command, and/or another command that is sensed by and/or input to the AR headset. When a C-arm imaging device captures multiple images for a surgical procedure, the images can be stored in the image database 950. Perspectives and other views for the procedure unique to each imaging system provide the wearer multiple ways to ensure accuracy of the planned tool trajectory, as well as selection of the correct tool and implant for use during the surgical procedure.

In some other embodiments, the AR headset is operatively connected to control transfer of surgical plan workflows and/or other information, e.g., images, from the computer platform 910 to the surgical robot 4, between two surgical robots 4, and/or between the surgical robot 4 and other medical devices.

In one embodiment, the AR headset is operatively connected to control cross-platform integration between one or more imaging systems, e.g., the C-arm imaging device 104 and/or the O-arm imaging device 106, and the computer platform 910. A wearer can manipulate control menus mapped in the virtual space of the AR headset to allow separate control of the imaging system and the computer platform 910. The wearer may navigate through control menus provided by the AR headset to plan and conduct imaging spins by the imaging system, and then rapidly conduct trajectory planning and tool selection through the computer platform 910 using the obtained images.

In a further embodiment, as the sight line of the AR headset wearer becomes directed towards a surgical robot 4, a graphical indicator can be displayed as an overlay that indicates that the wearer can now interface through the AR headset to control various operational functions of the surgical robot 4.

In another further embodiment, as the sight line of the AR headset wearer becomes directed towards a rod bender device, e.g., used for spinal alignment procedures, a graphical indicator can be displayed as an overlay that indicates that the wearer can now interface through the AR headset to control various operational functions of the rod bender, such as to shape rod implants based on present data from the computer platform 910 that is generated through planning of screw placement relative to one or more of the obtained medical image.

These and other related cross-platform operations that integrate an AR headset with various medical devices can reduce unnecessary downtime between stages of a surgical planning and execution procedure. By allowing the areas processes and workflows to transmit information between the various devices, more than one of the devices can be simultaneously working on the same workflow. These operations can avoid typical pauses that occur during a surgical procedure in the operating room while surgeons sequentially move through stages to obtain spinal images, plan screw placement within a spine using the spinal images, and shape a rod for connection to the spine.

An example workflow according to present embodiments can include, using the AR headset for navigation the wearer guides the C-arm imaging device 104 into position in order to take an imaging scan of the patient. Once in position, the wearer can use the AR headset display screen 1452 to find operational preferences for the imaging spin and to perform the imaging spin. The imaging spin generates a static image upon which the wearer uses to plan screw trajectories through the computer platform 910. Once the screw trajectories are planned, the wearer transfers the surgical plan to the surgical robot 4 to obtain navigated assistance during screw placement into the spine. Simultaneously, upon completion of trajectory planning, the wearer can send the completed trajectory plan to the rod bender device which begins bending of the spinal correction rod. While the rod bender device is bending the spinal correction rod using the completed trajectory plan, the wearer can use the AR headset to aid in screw placement through operation of the surgical robot 4. Once the screws are successfully in place in the patient's spine, the wearer can use a virtual model of the spinal correction rod generated from the cross-platform integration between the surgical robot 4 and rod bender device to ensure accuracy of the rod fitment to the screw trajectory before rod placement is performed.

Thus, in some further embodiments, the AR headset controller is configured to associate a set of defined hand gestures and/or a set of defined voice commands with a set of control commands for at least one external medical device, and identify occurrence of one of the defined hand gestures in a camera video stream and/or occurrence of one of the defined voice commands in an audio stream. The AR headset controller is configured to select a control command from among the set of control commands responsive to the identified occurrence of the one of the defined hand gestures and/or defined voice commands, and to communicate the selected control command to the external medical device.

In one embodiment, the set of control commands for the external medical device includes a command that controls at least one of movement of an imaging system, adjustment a region that is to be captured by the imaging system in an image, and initiate capture of the image by the imaging system.

In one embodiment, the set of control commands for the external medical device includes a command that controls at least one of transfer of a trajectory plan for a spinal correction rod to a rod bender device, initiating bending of the spinal correction rod by the rod bender device, and transfer of operational status information from the rod bender device to the AR headset for display.

AR Headset with Opacity Filter

Figure 32:
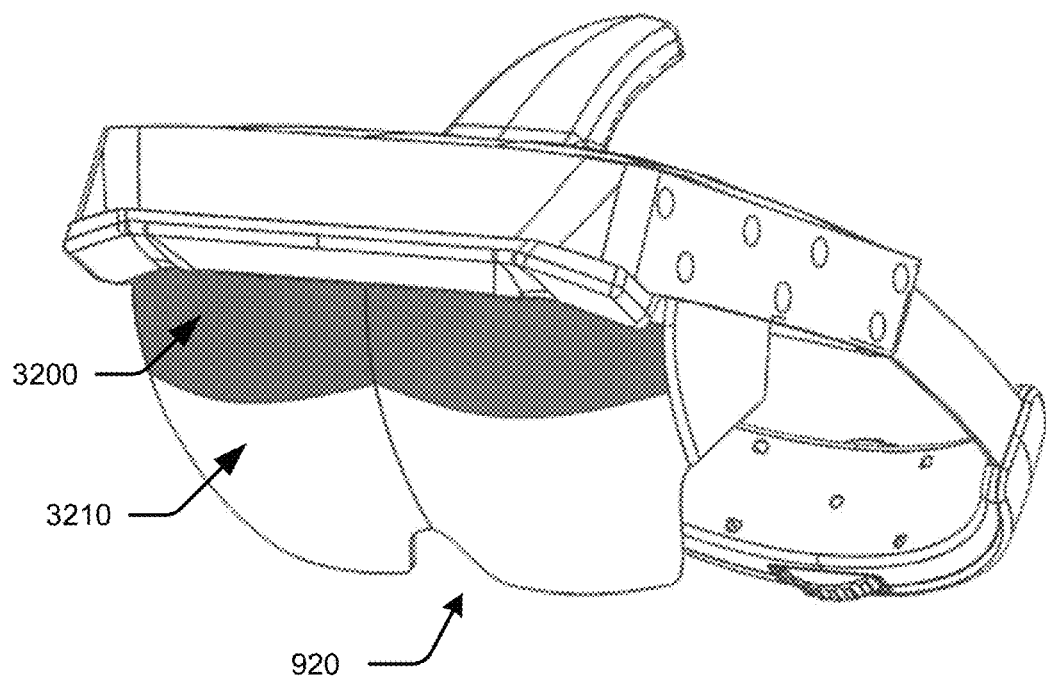
FIG. 32 illustrates an AR headset having a curved lens that operates as a see-through display screen which extends laterally across and downward from a front part of the AR headset, and an opacity filter that is on a surface of the curved lens, in accordance with some embodiments of the present disclosure.

FIG. 32 illustrates an AR headset 920 having a curved lens 3210 that extends laterally across and downward from a front part (e.g., headband) of the AR headset 920. In contrast to the AR headset 920 shown in FIG. 13, the AR headset 920 of FIG. 32 further includes an opacity filter 3200 that is configured as a laterally extending band on a surface of the curved lens 3210 in accordance with some embodiments of the present disclosure.

In the embodiment of FIG. 32, the curved lens 3210 operates as a see-through display screen, also referred to as a combiner, that reflects light from display panels toward the user's eyes. The display panels can be located between the electronic component enclosure and the user's head, and angled to project virtual content toward the curved lens 3210 for reflection toward the user's eyes. The combiner is semi-transparent and semi-reflective allowing the user to see reflected virtual content superimposed on the user's view of a real-world scene. The opacity of the opacity filter 3200 controls how much light from the real-world scene passes through to the user's eyes. A high opacity configuration of the opacity filter 3200 results in high-contrast virtual images overlaid on a dim view of the real-world scene. A low opacity configuration of the opacity filter 3200 can result in more faint virtual images overlaid on a clearer view of the real-world scene. The opacity filter may provide a non-changing opacity, such as by applying an opaque material on a surface of the lens 3210, or may provide an electrically controllable opacity, as will be explain in further detail below.

Figure 34:
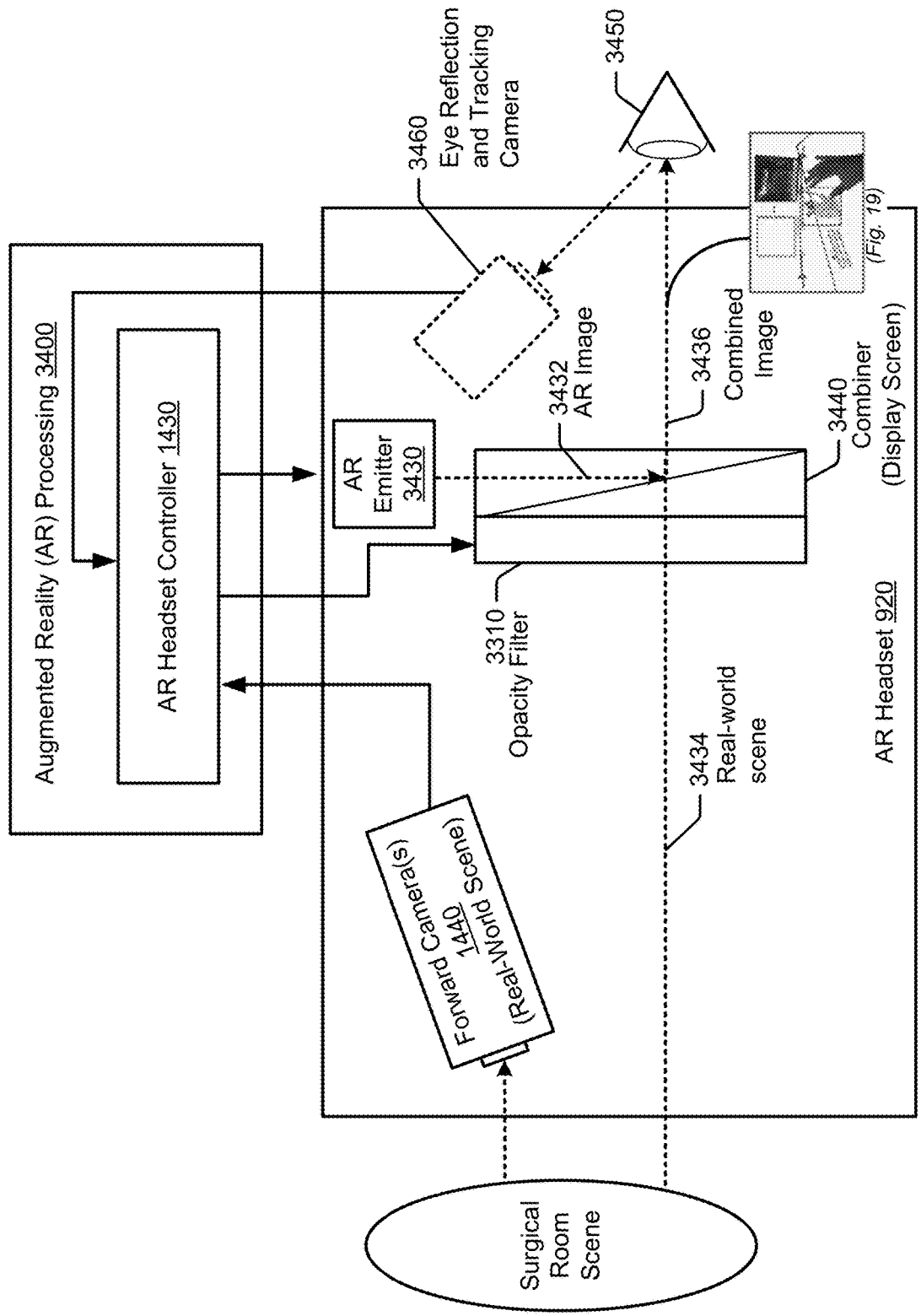
FIG. 34 illustrates a block diagram of components of a surgical system that includes an AR headset connected to AR processing circuitry that includes an AR headset controller configured in accordance with some embodiments of the present disclosure.

According to some embodiments the surgical system includes an AR headset 920 and an AR headset controller, e.g., controller 1430 in FIG. 14 or controller 3410 in FIG. 34. The AR headset 920 is configured to be worn by a user during a surgical procedure and has a see-through display screen 3210 that is configured to display an AR image and to allow at least a portion of a real-world scene to pass therethrough for viewing by the user. The AR headset 920 also includes an opacity filter positioned between at least one of the user's eyes and the real-world scene when the see-through display screen 3210 is viewed by the user. The opacity filter is configured to provide opaqueness to light from the real-world scene. The AR headset controller is configured to communicate with a navigation controller, e.g., controller(s) 828A, 828B, and/or 828C in FIG. 14, to receive navigation information from the navigation controller which provides guidance to the user during the surgical procedure on an anatomical structure, and is further configured to generate the AR image based on the navigation information for display on the see-through display screen 3210.

In a further embodiment, the see-through display screen 3210 includes a curved lens that extends laterally across and downward from a front part of the AR headset 920, and the opacity filter is on a surface of the curved lens. In another embodiment, the opacity filter is configured as at least two laterally extending bands, where an upper one of the at least two laterally extending bands has a lower light transmissivity than a lower one of the at least two laterally extending bands.

In another embodiment, the opacity filter is configured as a gradient having a more continuously changing opacity with distance downward from a top portion of the curved lens 3210 (see-through display screen). The gradient's darkest point can be located at the top portion of the curved lens 3210, and gradually becoming less opaque further down on the see-through curved lens 3210 until the opacity filter is transparent or not present on the curved lens 3210. In an example further embodiment, the gradient can change from about 90% opacity to entirely transparent approximately at the mid-eye level of the curved lens 3210. With the headset properly calibrated and positioned, the mid-eye level can correspond to the point where the user would look straight out, and the end of the gradient would be located at the "horizon" line of the eye. The darker portion of the gradient will allow crisp, clear visuals of the virtual content and help to block the intrusive brightness of the overhead operating room lights.

Using an opacity filter in this manner enables the AR headset 920 to provide virtual reality (VR) capabilities, by substantially or entirely blocking light from the real-world scene, along an upper portion of the curved lens 3210 and to provide AR capabilities along an middle or lower portion of the curved lens 3210. This allows the user to have the semi-translucence of AR where needed and allowing clear optics of the patient anatomy during procedures. Configuring the opacity filter 3200 as a gradient instead of as a more constant opacity band can enable the wearer to experience a more natural transition between a more VR type view to a more AR type view without experiencing abrupt changes in brightness of the real-world scene and depth of view that may otherwise strain the eyes such as during more rapid shifting between upward and downward views.

The display panels and curved lens 3210 can be configured to provide a wide field of view see-through AR display system. In one example configuration they provide an 80° diagonal field-of-view (FOV) with 55° of vertical coverage for a user to view virtual content. Other diagonal FOV angles and vertical coverage angles can be provided through different size display panels, different curvature lens, and/or different distances and angular orientations between the display panels and lens.

As explained above, an opacity filter operates to vary opacity of the real-world scene viewed through the headset. In one embodiment, the opacity filter and lens are configured to provide three different opacity views, such as: (a) a high opacity upper lens region where the real-world scene is significantly darkened and AR images (virtual content) are displayed with high contrast and viewing clarity, e.g., like a VR display; (b) a middle lens region having less opacity than the upper lens region and where more traditional AR is provided; and (c) a lower region before which the lens has ended so the user can look down to obtain a 100% unobstructed view of the real-world scene.

Accordingly, the high opacity, e.g., not less than 80% opaqueness, upper lens region, e.g., above the horizon, provides high contrast for display of AR images and where visual clarity of the real-world is less important. The lower opacity, e.g., no more than 50% opaqueness, middle lens region, e.g., below the horizon, provides less contrast for simultaneous viewing of AR images overlaid one the real-world scene. The lower region where the lens ends, e.g., 30° below the horizon, provides the user with unobstructed view of the real-world scene.

Some further embodiments are directed to the AR headset controller being configured to select among a plurality of different regions of the see-through display screen for displaying different types of AR images based on a characteristic of the type of AR image and levels of opaqueness of regions of the opacity filter aligned with the different regions of the see-through display screen. For example, AR images (virtual content) that is more important can be displayed above the horizon, such as within the high opacity upper lens region, to ensure it can be clearly viewed irrespective of bright operating room lighting, etc. Displaying important AR images within a higher opacity region of the opacity filter can be advantageous because minimal physical world interaction takes place within that viewed area during surgery. Some examples of AR images (virtual content) that can be configured for display or can be selected by the AR headset controller for display in the higher opacity region of the opacity filter, can include, but are not limited to any one or more of:

1) 2D Axial, Sagittal and/or Coronal views of patient anatomy;
2) overlay of planned vs currently tracked tool and surgical implant locations;
3) gallery of preoperative images;
4) video feeds from microscopes and other similar systems or remote video conferencing; and
5) options and configuration settings and buttons.

The middle lens region having less opacity than the upper lens region can provide a more traditional AR region for displaying AR content. Some examples of AR images (virtual content) that can be configured for display or can be selected by the AR headset controller for display in the middle lens region of the opacity filter, can include, but are not limited to any one or more of:

1) floating 3D models of patient anatomy with surgical planning information;
2) real-time tracking of surgical instruments relative to floating patient anatomy;
3) augmented overlay of patient anatomy with instructions and guidance; and
4) augmented overlay of surgical equipment.

The AR headset controller can be configured to determine where different types of AR images are displayed. In one embodiment, a plurality of different types of AR images are displayed sequentially or concurrently on the see-through display screen. For each of the plurality of types of AR images the AR headset controller is configured to select among a plurality of different regions of the see-through display screen for displaying the type of AR image based on a characteristic of the type of AR image and levels of opaqueness of regions of the opacity filter aligned with the different regions of the see-through display screen. For example, the AR headset controller may receive metadata that defines the type of AR image that will be received in a stream, and can responsively determine based on the metadata where it will display AR images in the stream. The metadata may be coded by a person to identify a preference for where the AR images in the stream should be displayed, or may identify characteristics, such as an indication of the type of images (e.g., 2D medical image, 3D graphical model, etc.) from which a ruleset can guide the AR headset controller decision as to where the AR images in the stream should be displayed. A user may input commands that move AR images between different regions of the see-through display screen and within a same region.

As shown in FIG. 32, the opacity filter 3200 can be configured as a laterally extending band. In some embodiments, the AR headset controller is configured to display in a region of the see-through display screen aligned with the laterally extending band of the opacity filter at least one of: 2D Axial, Sagital, and/or Coronal view images of patient anatomy; a planned and/or currently tracked surgical tool pose; graphical model of surgical implant location; video from a medical instrument; and user selectable menu items triggering operations controlling medical equipment. The AR headset controller is further configured to display in another region of the see-through display screen that is not aligned with the laterally extending band of the opacity filter at least one of: a 3D graphical model of the anatomical structure and surgical planning information; 3D graphical model of a surgical instrument; animated 3D graphical model of a surgical instrument displayed with a pose relative to a graphical model of the anatomical structure that is modified to track in real-time measured poses of the surgical instrument relative to the anatomical structure; and a graphical model of the anatomical structure and the navigation information from the navigation controller which provides visual guidance to the user during the surgical procedure on the anatomical structure.

It is noted that while an unobstructed view of a prone patient is easily obtained by looking downwards with both the eyes and head, an augmented view of the patient can also be obtained by pitching the head down a bit further to look through the middle lens region.

In this manner the AR headset can be configured to provide the mixed capabilities and benefits of both VR and AR, straddling the VR-AR continuum in such a way as to maximize the utility for applications such as live interoperative surgery. The AR headset provides options for how much contrast is to be provided between displayed AR images (virtual content such as medical imagery) and the real-world scene, by selectively displaying the AR images within the high opacity upper lens region or in the lower opacity middle lens region. The user can make subtle head pitching movement to adjust the various regions relative to the real-world scene, e.g., to obtain an AR image overlay on an anatomical structure and to alternatively obtain an unobstructed view of the anatomical structure. The AR headset can be configured to identify hand gestures and/or voice commands that control what types of AR content is displayed where on the lens forming the see-through display screen.

Dynamic Control of Opacity Filter and/or Brightness of Display

As explained above, the opacity of the opacity filter controls how much light from the real-world scene passes through to the user's eyes. A high opacity configuration of the opacity filter results in high-contrast virtual images overlaid on a dim view of the real-world scene. A low opacity configuration of the opacity filter can result in more faint virtual images overlaid on a clearer view of the real-world scene. In a surgical setting, neither the real-world view of the operation nor the clarity of the virtually displayed medical imagery should be compromised. Additionally, the operating room commonly contains both very bright lights (i.e., surgical lamps directed at the patient) as well as less well-lit areas resulting in an environment where a fixed opacity is unable to account for the different lighting conditions.

In addition to the overall opacity of the opacity filter, the color of the content in an AR image can dramatically impact visibility in different environments. Since virtual content is overlaid on the real-world scene, any virtual content whose color matches that of the real-world scene will be much more difficult for the user to perceive clearly. For example, a blue virtual menu will be difficult to read in a room with blue walls, but will be easier to read in a room with white walls. In a surgical setting, anything that reduces clarity or legibility is an issue that should be avoided.

Some embodiments of the present disclosure are directed to overcoming one or more of these problems by configuring the AR headset controller to electronically control opaqueness of regions of the opacity filter based on the brightness and/or color of the real-world scene and/or by configuring the AR headset controller to control the brightness and/or color of the AR image displayed on the see-through display screen based on the brightness and/or color of the real-world scene.

Figure 33:
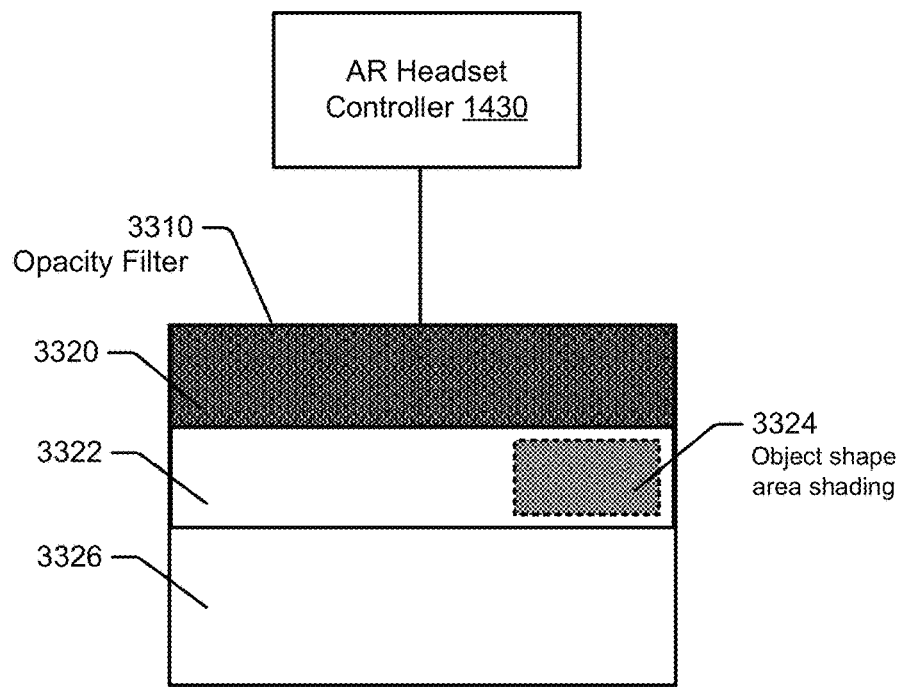
FIG. 33 illustrates a block diagram of another embodiment of an opacity filter configured to have changeable opacity responsive to signalling from an AR headset controller in accordance with some embodiments of the present disclosure.

FIG. 33 illustrates a block diagram of an opacity filter 3310 that is configured to have changeable opacity levels responsive to electrical signalling from the AR headset controller 1430 in accordance with some embodiments of the present disclosure. The opacity filter 3310 may be formed from electro chromatic material that is configured to have light transmission properties that change in response to applied voltage. In another embodiment, the opacity filter 3310 is formed from a liquid crystal device, such as a polymer-dispersed liquid crystal device, or other see-through device that is configured to have light transmission properties that are changeable in response to applied voltage and/or current.

The AR headset controller 1430 can be configured to electronically control the opacity of different regions of the opacity filter 3310. FIG. 33 illustrates that the AR headset controller 1430 can be configured to selectively control the opacity of different regions of the opacity filter 3310, such as by providing three different opacity laterally extending regions 3320, 3322, and 3326. Alternatively or additionally, the AR headset controller 1430 can be compared to control the opacity of smaller defined areas, such as area 3324 which may be positioned to be aligned with a VR object that is displayed on the see-through display screen 3324 to reduce real-world light passing through that object and thereby increase the object's contrast viewability.

FIG. 34 illustrates a block diagram of components of a surgical system that includes an AR headset 920 connected to AR processing circuitry 3400, which may reside in the computer platform 910, that includes an AR headset controller 1430 configured in accordance with some embodiments of the present disclosure. FIG. 35-39 illustrate flowcharts of operations that can be performed by the AR headset controller 3410 to control how information is displayed on the see-through display screen and/or to control opacity of the opacity filter in accordance with some embodiments of the present disclosure.

Referring to FIG. 34, the AR headset 920 includes an AR emitter 3430 that is configured to project light for the AR images responsive to signalling from the AR headset controller 1430. The AR emitter 3430 projects light toward a combiner 3440 which is configured to combine the light of the AR images 3432 projected from the AR light emitter 3430 and light from the real-world scene 3434 into a combined overlay image 3436 that is viewable by the user 3450. The combiner 3440 configured in this manner operates as a see-through display screen. The opacity filter 3310 is aligned with the combiner 3440 so that light from the real-world scene 3434 passes through the opacity filter 3310, where the light can be filtered, before passing through the combiner 3440 along the line of sight of the user 3450. A rear surface of the opacity filter 3310 may be directly on a front surface of the combiner 3440, in the direction of light arrival from the real-world scene.

In some embodiments, an opacity filter is directly on the combiner 3440 and provides a fixed amount of shading. The opacity filter may include shading that is applied directly to a surface of the combiner 3440 to provide a fixed amount of opacity filtering of the real-world scene. For example, one or more laterally extending bands of one or more levels of shading can be formed directly on a surface of the combiner 3440. Alternatively, a shading gradient can be formed directly on a surface of the combiner 3440. The shading may be used instead of an electronically controllable opacity filter 3310 or may be used in combination with an electronically controllable opacity filter 3310 to darken the real-world scene.

The surgical system can include a camera that is configured to output video frames capturing the real-world scene. In the embodiment of FIG. 34, one or more forward cameras 1440 can be configured to view the real-world scene along a line of sight of the user. Alternatively or additionally, a camera 3460 may be positioned and configured to sense reflections from one of the user's eyes 3450 in order to capture the real-world scene viewed by the user. The camera 3460 may additionally be used to track where the user is looking and the AR headset controller 1430 may be configured to adjust opacity of the opacity filter 3310 and/or the brightness and/or color of the AR image that is displayed based on where signalling indicating where the user is looking.

Various further embodiments are directed to the AR headset controller 1430 being configured to electronically control opaqueness of regions of the opacity filter 3310 based on the brightness and/or color of the real-world scene and/or directed to the AR headset controller 1430 being configured to control the brightness and/or color of the AR image displayed on the see-through display screen, i.e. projected by the AR emitter 3430 toward the combiner 3440, based on the brightness and/or color of the real-world scene.

Figure 35:
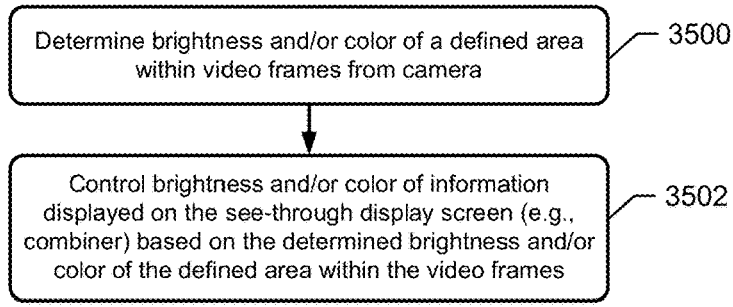
FIG. 35-39 illustrate flowcharts of operations that can be performed by the AR headset controller and the computer platform of the surgical system to control how information is displayed on the see-through display screen and/or to control opacity of the opacity filter in accordance with some embodiments of the present disclosure.

Referring to the operational embodiment of FIG. 35, the AR headset controller 1430 is configured to determine 3500 brightness and/or color of a defined area within the video frames, and to control 3502 brightness and/or color of the AR image displayed on the see-through display screen, i.e. projected by the AR emitter 3430 toward the combiner 3440, based on the determined brightness and/or color of the defined area within the video frames.

The AR headset controller 1430 may be part of AR processing circuitry 3400 that can be within a housing that is configured to be worn on a user's head or elsewhere on the user's body while viewing the display screen 1450 or may be remotely located from the user viewing the display screen while being communicatively connected to the display screen 1450, such as within a networked server.

Figure 36:
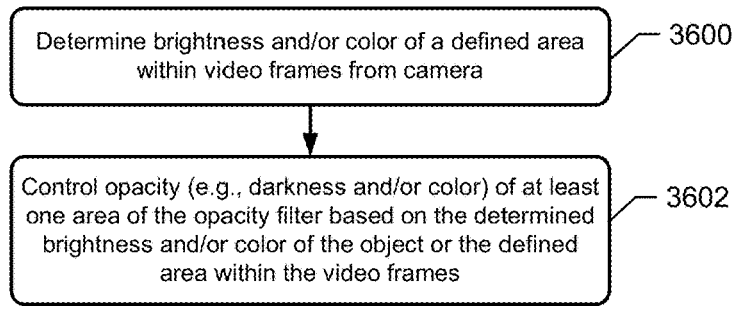

Referring to operational embodiment of FIG. 36, the AR headset controller 1430 is configured to determine 3600 brightness and/or color of a defined area within the video frames, and to control 3602 opacity of at least one area of the opacity filter 3310, e.g., band 3320 in FIG. 33, based on the determined brightness and/or color of the defined area within the video frames.

Figure 37:
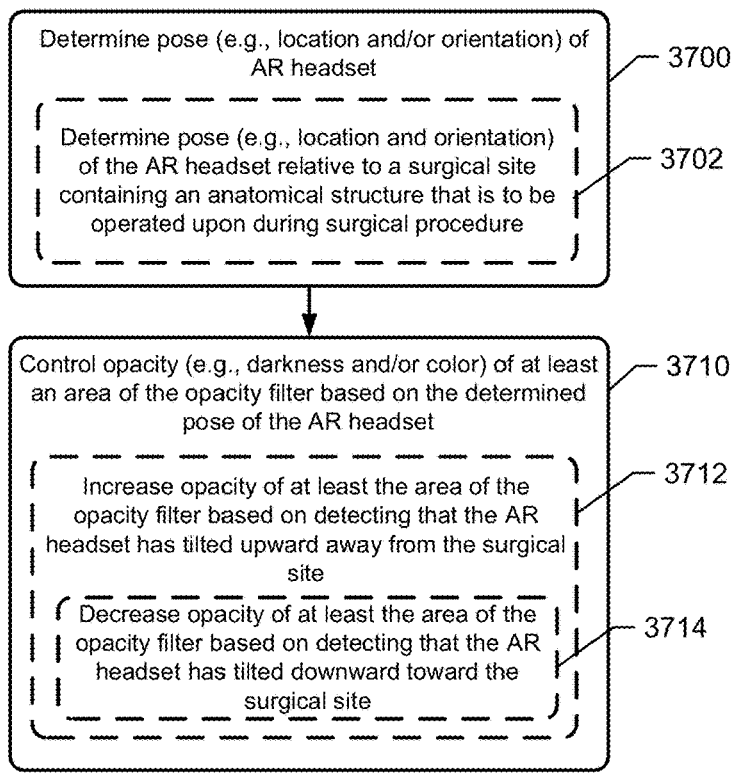
Figure 38:
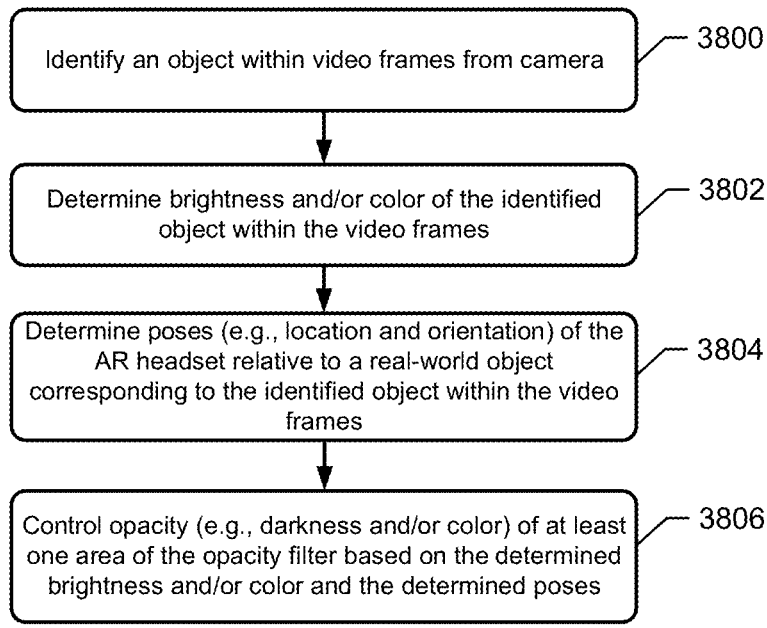
Figure 39:
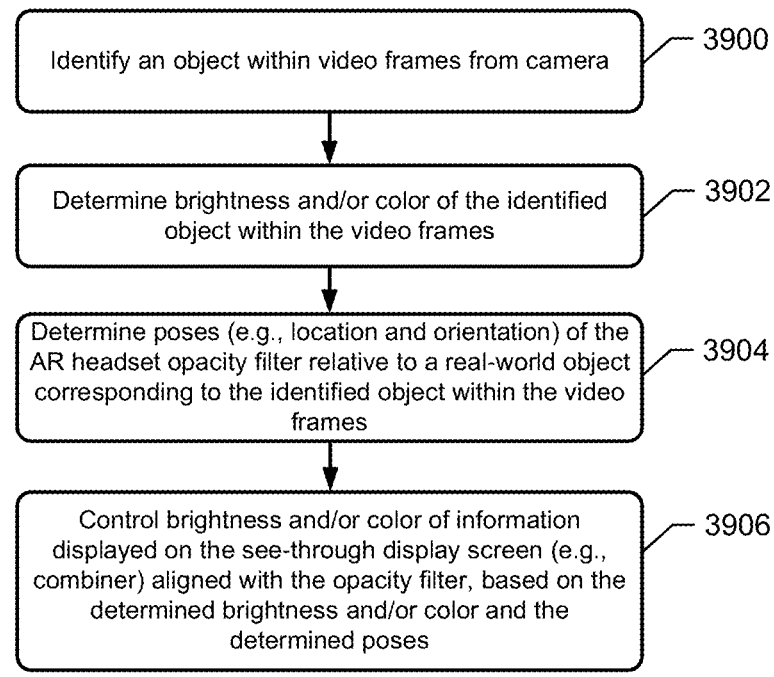

Referring to operational embodiments of FIG. 37, the AR headset controller 1430 is configured to determine 3700 poses, e.g. locations and/or angular orientations along two or more defined axes, of the AR headset 920, and to control 3710 opacity, e.g. darkness and/or color, of at least one area of the opacity filter 3310 based on the determined poses of the AR headset 920. The AR headset controller 1430 can be configured to determine 3702 the poses of the AR headset relative to a surgical site containing an anatomical structure, and to control opacity of at least one area of the opacity filter based on the determined poses of the AR headset relative to the surgical site. For example, in FIG. 33 the AR headset controller 1430 may darken area 3324 based on that area being determined to be a defined offset distance from the anatomical structure along a sightline of the user, so as to increase contrast for viewing an associated AR image.

The AR headset controller 1430 may be configured to darken the opacity filter 3310 to increase the user's view ability of AR images while the user is looking upward away from a surgical site. For example, they are headset controller 1430 may be configured to increase 3712 opacity of at least an area of the opacity filter 3310 based on detecting that the AR headset is tilted upward away from the surgical site, and then decrease 3714 opacity of that area of opacity filter 3310 based on detecting that the AR headset has tilted downward toward the surgical site.

The AR headset controller 1430 may be configured to control opacity of an area of the opacity filter based on brightness and/or color of an object that is identified within video frames from a camera 1440/3460. Referring to operational embodiments of FIG. 38, the AR headset controller 1430 is configured to identify 3800 an object within the video frames, determine 3802 brightness and/or color of the identified object within the video frames, determine 3804 poses of the AR headset 920 relative to a real-world object corresponding to the identified object within the video frames, and to control 3806 opacity (e.g., darkness and/or color) of at least one area of the opacity filter 3310 based on the determined brightness and/or color of the identified object within the video frames and based on the determined poses.

The AR headset controller 1430 may be configured to control brightness and/or color of information displayed on the see-through display screen, i.e. projected by the AR emitter 3430 toward the combiner 3440, based on brightness and/or color of an object that is identified within video frames from a camera 1440/3460. Referring to operational embodiments of FIG. 39, the AR headset controller 1430 is configured to identify an object 3900 within the video frames, determine 3902 brightness and/or color of the identified object within the video frames, determine 3904 poses (e.g., location and/or angular orientation) of the AR headset 920 relative to a real-world object corresponding to the identified object within the video frames, and to control 3906 brightness and/or color of the AR image displayed on the see-through display screen based on the determined brightness and/or color of the identified object within the video frames and based on the determined poses.

The AR headset controller 1430 may be configured to control opacity of individual pixels or groups of pixels of the opacity filter 3310. For example, the opacity filter 3310 can be configured to have a plurality of pixels that are arranged in a grid and which are electrically controllable to adjust pixel opacity to light transmissivity. The AR headset controller 1430 can be configured to electrically control the opacity filter 3310 to provide an increased opacity for at least some pixels that are selected among the grid based on being aligned with or offset a distance from at least a portion of a shape of an AR image displayed on the see-through display screen, i.e. projected by the AR emitter 3430 toward the combiner 3440. For example, the user's view of bright lighting in the operating room can be dimmed by the AR headset controller 1430 providing increased opacity for a group of pixels of the opacity filter 3310 that are aligned with the lighting along a sightline of the user. In a similar manner, an area that is offset a defined distance from an anatomical structure can be dimmed during a surgical procedure to provide increased viewability of AR images overlaid on that area, by the AR headset controller 1430 providing increased opacity for a group of pixels of the opacity filter 3310 that are aligned with that area along a sightline of the user.

In some other embodiments, the area behind content of an AR image can be darkened and the darkened area can be moved to track movement of the AR headset and/or where the AR image is being displayed. For example, the AR headset controller 1430 can be configured to electrically control the opacity filter 3310 to provide an increased opacity for at least some pixels that are selected among the grid to form a shape that is defined based on a perimeter of the shape of AR image displayed on the see-through display screen. The AR headset controller 1430 can be configured to electrically control the opacity filter 3310 to provide a region of pixels selected among the grid with a relatively high opacity based on being aligned with at least a portion of the shape of the AR image displayed on the see-through display screen, and to provide another region of pixels selected among the grid with a gradual transition in opacity based on being peripherally outside the shape of the AR image displayed on the see-through display screen.

Using a visible light camera 1440/3460 to detect environmental lighting conditions on the combiner 3440 and electrically control opacity of the opacity filter 3310 can overcome a variety of visibility and contrast issues that arise during surgeries. This setup allows for dynamic adjustment of both combiner opacity and color based on lighting conditions, virtual content, and even user preference.

There are many use cases where dynamically controlling the combiner opacity in a VR headset will provide better clarity for the user.

In one use case, some content needs to be seen clearly in all cases. For instance, the medical imagery used for live surgical navigation should be shown with the highest possible clarity. Dynamic combiner opacity would allow these images to always be displayed on a dark background.

FIG. 32 shows an example of darkening a specific region (top laterally extending band) of the see-through display screen (combiner) based on the content shown there. In this example, the medical imagery can be display in the upper portion of the combiner. Whenever medical imagery occupies that space, the region would be darkened; when absent, the region would revert to its normal transparency. This dynamic adjustment allows for high contrast opacity exactly where and when it is needed but nowhere else.

In a second use case, dynamic opacity adjustment allows for responsive changes to the environment's lighting conditions which is especially important in the operating room. The surgical site is frequently spot lit with high powered surgical lamps while other parts of the room are lit less intensely. Using visible light cameras attached to the headset 920, or any other way to determine the lighting conditions in the environment, the software can determine which parts of the combiner need to be darkened to account for the room's lighting. For example, the AR headset controller 1430 can respond to sensing a bright light source in the left portion of the user's field of view by responsively darkening the left side of each combiner (when separate combiners are provided for each eye) or providing darkened spaced apart left regions on a single combiner with the regions being aligned with the user's left field of views for the corresponding eyes. The right side of the combiners is kept more transparent since the right portion of the user's field of view is not as intensely lit. If the surgeon were to move elsewhere in the room or turn on additional lighting, the darkened region could be adjusted to respond to the new lighting conditions.

Similarly, the lighting conditions of the room can be used to dynamically adjust the color palette of the virtual content to create better contrast. In the same way that a visible light camera could be used to determine the overall brightness of the environment. The camera output video frames can be used to determine the dominant background color of different parts of the room. This information can be used by the AR headset controller 1430 to select an appropriate contrasting color for the virtual content that is rendered. Between the dynamically controlled combiner opacity and the adjustment of the virtual content's color palette, the headset 920 can maintain good clarity and high contrast imagery regardless of environmental lighting conditions.

In a third use case, dynamic opacity adjustment is performed to cater to surgeons' individual preferences. Since the opacity can be controlled via software executed by the AR headset controller 1430, the user can be given direct control over the appearance of mechanically predefined combiner sections. This style of direct control could be used in conjunction with other automatic adjustment processes (such as for specific content background or for environmental lighting conditions) by using the custom settings as a baseline and adjusting dynamically from that starting point. There are many reasons the user might want to customize the opacity: some surgeons may prefer a more minimally obstructed view of the surgical site and desire only faint virtual objects; some surgeons may want high visibility to enable direct eye contact with assistants, technicians, and other doctors in the room; and others may prefer to navigate primarily with the virtual medical imagery and would therefore want almost complete opacity in some regions. Regardless of the reason, this technology allows the surgeon to customize their experience for the current case, the operating room, and, most importantly, their own preferences.

Further Definitions and Embodiments

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, microcode, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Many variations and modifications can be made to the embodiments without substantially departing from the principles of the present inventive concepts. All such variations and modifications are intended to be included herein within the scope of present inventive concepts. Accordingly, the above disclosed subject matter is to be considered illustrative, and not restrictive, and the appended examples of embodiments are intended to cover all such modifications, enhancements, and other embodiments, which fall within the spirit and scope of present inventive concepts. Thus, to the maximum extent allowed by law, the scope of present inventive concepts are to be determined by the broadest permissible interpretation of the present disclosure including the following examples of embodiments and their equivalents, and shall not be restricted or limited by the foregoing detailed description.

What is claimed is:

1. A surgical system comprising:
    an augmented reality (AR) headset configured to be worn by a user during a surgical procedure and including:
        an AR transmitter configured to project light for an AR image;
        a see-through display screen configured to combine the projected AR image and a real-world scene for viewing by the user, and
        an opacity filter positioned between at least one of the user's eyes and the real-world scene when the see-through display screen is viewed by the user, wherein the opacity filter is configured to provide opaqueness to light from the real-world scene; and
    AR headset controller configured to communicate with a navigation controller to receive navigation information from the navigation controller which provides guidance to the user during the surgical procedure on an anatomical structure, and configured to generate the AR image based on the navigation information for display on the see-through display screen;
    wherein the opacity filter is configured with at least two horizontally extending bands extending over both eyes, each band extending across the entire width of the see-through display screen, wherein an upper one of the at least two horizontally extending bands has a lower light transmissivity than a lower one of the at least two horizontally extending bands;

wherein the augmented reality headset is operationally coupled to a robotic system having a robotic arm that is controllable based on hand gesture commands that is sensed by the augmented reality headset.

2. The surgical system of claim 1, wherein the see-through display screen includes a curved lens that extends laterally across and downward from a front part of the AR headset, and the opacity filter is on a surface of the curved lens.

3. The surgical system of claim 1, wherein:

the opacity filter is configured as a laterally extending band;

the AR headset controller is configured to display in a region of the see-through display screen aligned with the laterally extending band of the opacity filter at least one of: 2D Axial, Sagital, and/or Coronal view images of patient anatomy; a planned and/or currently tracked surgical tool pose; graphical model of surgical implant location; video from a medical instrument; and user selectable menu items triggering operations controlling medical equipment, and to display in another region of the see-through display screen that is not aligned with the laterally extending band of the opacity filter at least one of: a 3D graphical model of the anatomical structure and surgical planning information; 3D graphical model of a surgical instrument; animated 3D graphical model of a surgical instrument displayed with a pose relative to a graphical model of the anatomical structure that is modified to track in real-time measured poses of the surgical instrument relative to the anatomical structure; and a graphical model of the anatomical structure and the navigation information from the navigation controller which provides visual guidance to the user during the surgical procedure on the anatomical structure.

4. The surgical system of claim 1, wherein:

the opacity filter is configured as a laterally extending band, wherein the see-through display screen includes a combiner configured to combine the light of the AR images projected from the AR light emitter and light from the real-world scene into a combined overlay image viewable by the user, and wherein the laterally extending band of the opacity filter is on a surface of the combiner.

5. The surgical system of claim 1, further comprising:

an AR emitter configured to project light of the AR images responsive to signalling from the AR headset controller, wherein the see-through display screen includes a combiner configured to combine light of the AR images projected from the AR emitter and light from the real-world scene into a combined image viewable by the user, and wherein the opacity filter includes an opacity gradient that extends on a surface of the combiner.

6. The surgical system of claim 1, wherein for each of a plurality of types of AR images the AR headset controller is configured to select among a plurality of different regions of the see-through display screen for displaying the type of AR image based on a characteristic of the type of AR image and levels of opaqueness of regions of the opacity filter aligned with the different regions of the see-through display screen.

7. The surgical system of claim 1, further comprising:

a camera configured to output video frames capturing the real-world scene, wherein the AR headset controller is configured to determine brightness and/or color of a defined area within the video frames, and to control opacity of at least one area of the opacity filter based on the determined brightness and/or color of the defined area within the video frames.

8. The surgical system of claim 1, further comprising:

a camera configured to output video frames capturing the real-world scene, wherein the AR headset controller is configured to determine brightness and/or color of a defined area within the video frames, and to control brightness and/or color of the AR image displayed on the see-through display screen based on the determined brightness and/or color of the defined area within the video frames.

9. The surgical system of claim 1, wherein the AR headset controller is configured to determine poses of the AR headset, and to control opacity of at least one area of the opacity filter based on the determined poses of the AR headset.

10. The surgical system of claim 9, wherein the AR headset controller is configured to determine the poses of the AR headset relative to a surgical site containing the anatomical structure, and to control opacity of at least one area of the opacity filter based on the determined poses of the AR headset relative to the surgical site.

11. The surgical system of claim 1, further comprising:

a camera configured to output video frames capturing the real-world scene, wherein the AR headset controller is configured to identify an object within the video frames, determine brightness and/or color of the identified object within the video frames, determine poses of the AR headset relative to a real-world object corresponding to the identified object within the video frames, and to control opacity of at least one area of the opacity filter based on the determined brightness and/or color of the identified object within the video frames and based on the determined poses.

12. The surgical system of claim 1, further comprising:

a camera configured to output video frames capturing the real-world scene, wherein the AR headset controller is configured to identify an object within the video frames, determine brightness and/or color of the identified object within the video frames, determine poses of the AR headset relative to a real-world object corresponding to the identified object within the video frames, and to control brightness and/or color of the AR image displayed on the see-through display screen based on the determined brightness and/or color of the identified object within the video frames and based on the determined poses.

13. The surgical system of claim 1, wherein:

the opacity filter includes a plurality of pixels arranged in a grid and electrically controllable to adjust pixel opacity to light transmissivity; and wherein the AR headset controller is configured to electrically control the opacity filter to provide an increased opacity for at least some pixels that are selected among the grid based on being aligned with or offset a distance from at least a portion of a shape of an AR image displayed on the see-through display screen.

14. The surgical system of claim 13, wherein the AR headset controller is configured to electrically control the opacity filter to provide an increased opacity for at least some pixels that are selected among the grid to form a shape that is defined based on a perimeter of the shape of AR image displayed on the see-through display screen.

15. The surgical system of claim 13, wherein the AR headset controller is configured to electrically control the opacity filter to provide a region of pixels selected among the grid with a relatively high opacity based on being aligned with at least a portion of the shape of the AR image displayed on the see-through display screen, and to provide another region of pixels selected among the grid with a gradual transition in opacity based on being peripherally outside the shape of the AR image displayed on the see-through display screen.

16. An augmented reality (AR) headset comprising:
   an AR transmitter configured to project light for an AR image;
   a see-through display screen configured to combine the projected AR image and a real-world scene for viewing by the user; and
   an opacity filter is configured to be positioned between at least one of the user's eyes and the real-world scene while the user is wearing the AR headset to view the see-through display screen, wherein the opacity filter is configured to provide opaqueness to light from the real-world scene,
   wherein the opacity filter is configured with at least two horizontally extending bands extending over both eyes, each band extending across the entire width of the see-through display screen, wherein an upper one of the at least two horizontally extending bands has a lower light transmissivity than a lower one of the at least two horizontally extending bands;
   wherein the augmented reality headset is operationally coupled to a robotic system having a robotic arm, the robotic system being controllable based on hand gesture commands that is sensed by the augmented reality headset.

17. The AR headset of claim 16, further comprising:
   an AR headset controller configured to communicate with a navigation controller, wherein the AR headset controller is configured to receive navigation information from the navigation controller which provides visual guidance to the user during a surgical procedure, and to generate the AR image based on the navigation information for display on the see-through display screen,
   wherein the see-through display screen includes a curved lens that extends laterally across and downward from a front bar of the AR headset, the opacity filter is configured as a laterally extending band on a surface of the curved lens, and the AR headset controller is configured to display in a region of the see-through display screen aligned with the laterally extending band of the opacity filter AR images that are generated using one set of types of navigation information and to display in another region of the see-through display screen that is not aligned with the laterally extending band of the opacity filter AR images that are generated using a different set of types of navigation information.

18. The AR headset of claim 16, further comprising:
   an AR headset controller configured to communicate with a navigation controller, wherein the AR headset controller is configured to receive navigation information from the navigation controller which provides visual guidance to the user during a surgical procedure, and to generate the AR image based on the navigation information for display on the see-through display screen; and
   an AR emitter configured to project light of the AR images responsive to signalling from the AR headset controller,
   wherein the see-through display screen includes a combiner configured to combine light of the AR images projected from the AR emitter and light from the real-world scene into a combined image viewable by the user, and
   wherein the opacity filter is on a surface of the combiner.

19. The AR headset of claim 16, further comprising:
   a camera configured to output video frames capturing the real-world scene; and
   an AR headset controller configured to
   communicate with a navigation controller to receive navigation information providing guidance to the user during a surgical procedure,
      generate the AR image based on the navigation information for display on the see-through display screen,
      determine brightness and/or color of a defined area within the video frames, and control opacity of at least one area of the opacity filter based on the determined brightness and/or color of the defined area within the video frames.

20. The AR headset of claim 16, further comprising:
   A camera configured to output video frames capturing the real-world scene; and
   an AR headset controller configured to
      communicate with a navigation controller to receive navigation information providing guidance to the user during a surgical procedure,
      generate the AR image based on the navigation information for display on the see-through display screen,
      determine brightness and/or color of a defined area within the video frames, and control brightness and/or color of the AR image displayed on the see-through display screen based on the determined brightness and/or color of the defined area within the video frames.

* * * * *